US008022214B2

(12) United States Patent
Facchetti et al.

(10) Patent No.: US 8,022,214 B2
(45) Date of Patent: Sep. 20, 2011

(54) ORGANIC SEMICONDUCTOR MATERIALS AND PRECURSORS THEREOF

(75) Inventors: Antonio Facchetti, Chicago, IL (US); Tobin J. Marks, Evanston, IL (US); He Yan, Skokie, IL (US)

(73) Assignee: Polyera Corporation, Skokie, IL (US)

( * ) Notice: Subject to any disclaimer, the term of this patent is extended or adjusted under 35 U.S.C. 154(b) by 911 days.

(21) Appl. No.: 12/011,030

(22) Filed: Jan. 23, 2008

(65) Prior Publication Data

US 2008/0249309 A1    Oct. 9, 2008

Related U.S. Application Data

(60) Provisional application No. 60/897,257, filed on Jan. 24, 2007.

(51) Int. Cl.
*C07D 471/08* (2006.01)
*H01L 21/36* (2006.01)
*H01L 51/50* (2006.01)

(52) U.S. Cl. .......... 546/37; 438/483; 313/498; 313/504

(58) Field of Classification Search .................. 546/37; 438/483; 313/498, 504
See application file for complete search history.

(56) References Cited

U.S. PATENT DOCUMENTS

| | | | |
|---|---|---|---|
| 2,087,133 A | 7/1937 | Vollmann | |
| 4,378,302 A | 3/1983 | Aftergut et al. | |
| 4,611,385 A | 9/1986 | Forrest et al. | 29/574 |
| 4,846,892 A | 7/1989 | Henning et al. | |
| 5,405,962 A | 4/1995 | Muellen et al. | |
| 5,472,494 A | 12/1995 | Hetzenegger et al. | |
| 5,539,100 A | 7/1996 | Wasielewski et al. | |
| 5,677,417 A | 10/1997 | Muellen et al. | |
| 5,808,073 A | 9/1998 | Böhm et al. | |
| 5,908,583 A | 6/1999 | Havinga et al. | |
| 5,986,099 A | 11/1999 | Mullen et al. | |
| 6,063,181 A | 5/2000 | Bohm et al. | |
| 6,084,099 A | 7/2000 | Hackmann et al. | |
| 6,099,636 A | 8/2000 | Henning et al. | |
| 6,124,458 A | 9/2000 | Müellen et al. | |
| 6,143,905 A | 11/2000 | Bohm et al. | |
| 6,165,661 A | 12/2000 | Hsiao et al. | |
| 6,184,378 B1 | 2/2001 | Bohm et al. | |
| 6,252,245 B1 | 6/2001 | Katz et al. | |
| 6,287,738 B1 | 9/2001 | Duff et al. | |
| 6,326,494 B1 | 12/2001 | Bohm et al. | |
| 6,348,595 B1 | 2/2002 | Hendi | |
| 6,486,319 B1 | 11/2002 | Böhm et al. | |
| 6,533,857 B1 | 3/2003 | Schmid et al. | |
| 6,551,717 B2 | 4/2003 | Katz et al. | 428/447 |
| 6,585,914 B2 | 7/2003 | Marks et al. | |
| 6,608,323 B2 | 8/2003 | Marks et al. | |
| 6,656,651 B1 | 12/2003 | Bender et al. | |
| 6,727,318 B1 | 4/2004 | Mathauer et al. | |
| 6,784,301 B2 | 8/2004 | Hackmann et al. | |
| 6,806,368 B2 | 10/2004 | Wurthner et al. | |
| 6,878,825 B2 | 4/2005 | Krieger et al. | |
| 6,890,377 B2 | 5/2005 | Böhm et al. | |
| 6,916,928 B2 | 7/2005 | Becker et al. | |
| 6,986,811 B2 | 1/2006 | Könemann et al. | |
| 7,083,675 B2 | 8/2006 | Mizuguchi et al. | |
| 7,105,046 B2 | 9/2006 | Mizuguchi et al. | |
| 7,105,674 B2 | 9/2006 | Hackmann et al. | |
| 7,326,956 B2 | 2/2008 | Shukla et al. | |
| 7,422,777 B2 | 9/2008 | Shukla et al. | |
| 7,893,265 B2 * | 2/2011 | Facchetti et al. | 546/37 |
| 2003/0181721 A1 | 9/2003 | Wurthner et al. | |
| 2003/0219625 A1 | 11/2003 | Wolk et al. | |
| 2004/0013959 A1 | 1/2004 | Bender et al. | |
| 2004/0023061 A1 | 2/2004 | Kathirgamanathan et al. | |
| 2005/0075453 A1 | 4/2005 | Mathauer et al. | |
| 2005/0092982 A1 | 5/2005 | Mullen et al. | |
| 2005/0106415 A1 | 5/2005 | Jarikov et al. | |
| 2005/0131220 A1 | 6/2005 | Dung et al. | |
| 2005/0171252 A1 | 8/2005 | Schambony et al. | |
| 2005/0176970 A1 | 8/2005 | Marks et al. | |
| 2005/0222416 A1 | 10/2005 | Bohm et al. | |
| 2005/0238974 A1 | 10/2005 | Sekiya et al. | |
| 2005/0251930 A1 | 11/2005 | Erk et al. | |
| 2006/0058330 A1 | 3/2006 | Krieger et al. | |
| 2006/0075585 A1 | 4/2006 | Krieger et al. | |
| 2006/0131564 A1 | 6/2006 | Shukla et al. | |
| 2006/0134823 A1 | 6/2006 | Shukla et al. | |
| 2006/0141287 A1 | 6/2006 | Klubek et al. | |
| 2006/0210898 A1 | 9/2006 | Jubran | |
| 2006/0229385 A1 | 10/2006 | Boehm | |

(Continued)

FOREIGN PATENT DOCUMENTS

DE    2951349 A1    7/1981

(Continued)

OTHER PUBLICATIONS

Jones et al., "High-Mobility Air-Stable n-Type Semiconductors with Processing Versatility: Dicyanoperylene-3,4:9,10-bis(dicarboximides)," *Angew., Chem. Int. Ed.*, 43:6363-6366 (2004).
Petit et al., "Synthesis of macromolecular substances comprising dye derivatives as monomeric units. III. Synthesis and study of monomeric dihydroxy dyes," *Bulletin de la Societe Chimique de France*, 7-8:1591-1596 (1974).
Shimizu et al., "Convergent Functional Groups. 15. Synthetic and Structural Studies of Large and Rigid Molecular Clefts," *J. Am. Chem. Soc.*, 116:5145-5149 (1994).
Singh et al., "Soluble derivatives of perylene and naphthalene diimide for n-channel organic field-effect transistors," *Organic Electronics*, 7:480-489 (2006).
Tsoi et al., "Distributed Bilayer Photovoltaics Based on Nematic Liquid Crystal Polymer Networks," *Chem. Mater.*, 19:5475-5484 (2007).
Ahrens et al., "Cyanated Perylene-3,4-dicarboximides and Perylene-3,4:9,10-bis(dicarboximide):Facile Chromophoric Oxidants for Organic Photonics and Electronics," *Chem. Mater.*, 15:2684-2686 (2003).
Baier et al., "Intermolecular energy transfer after vibrational excitation of a perylene dye in solution, in polymer binder, and in a side-chain copolymer," *J. Chem. Phys.*, 114: 6739-6743 (2001).

(Continued)

*Primary Examiner* — Charanjit Aulakh
(74) *Attorney, Agent, or Firm* — K&L Gates LLP

(57) ABSTRACT

The present teachings provide novel organic semiconductor compounds and their soluble precursors, methods for preparing these compounds and precursors, as well as compositions, materials, articles, structures, and devices that incorporate such compounds.

20 Claims, 7 Drawing Sheets

U.S. PATENT DOCUMENTS

| | | |
|---|---|---|
| 2006/0237712 A1 | 10/2006 | Shukla et al. |
| 2007/0026332 A1 | 2/2007 | Ferrar et al. |
| 2007/0096084 A1 | 5/2007 | Shukla et al. |
| 2007/0116895 A1 | 5/2007 | Shukla et al. |
| 2008/0021220 A1 | 1/2008 | Marks et al. |
| 2008/0135833 A1 | 6/2008 | Shukla et al. |
| 2008/0161569 A1 | 7/2008 | Dung et al. |
| 2008/0167435 A1 | 7/2008 | Marks et al. |
| 2008/0177073 A1 | 7/2008 | Facchetti et al. |
| 2008/0185555 A1 | 8/2008 | Facchetti et al. |
| 2008/0185577 A1 | 8/2008 | Facchetti et al. |

FOREIGN PATENT DOCUMENTS

| | | |
|---|---|---|
| DE | 3434059 | 3/1985 |
| DE | 3620332 A1 | 12/1987 |
| DE | 3703131 | 8/1988 |
| DE | 4018830 | 12/1991 |
| DE | 4338784 | 5/1995 |
| DE | 4440242 | 5/1996 |
| DE | 19501737 A1 | 7/1996 |
| DE | 19547210 A1 | 6/1997 |
| DE | 19622673 A1 | 12/1997 |
| DE | 19651712 A1 | 6/1998 |
| DE | 197 09 008 | 9/1998 |
| DE | 10038672 A1 | 5/2002 |
| DE | 10148172 A1 | 4/2003 |
| EP | 0031065 | 10/1983 |
| EP | 0 217 256 | 4/1987 |
| EP | 0 422 535 | 4/1991 |
| EP | 0 826 740 | 3/1998 |
| EP | 0 861 878 | 9/1998 |
| EP | 0 896 964 | 2/1999 |
| EP | 0 990 951 | 4/2000 |
| EP | 1 172 700 | 1/2002 |
| EP | 1 671 674 | 6/2006 |
| FR | 1 526 496 | 5/1968 |
| FR | 2 237 922 | 2/1975 |
| JP | 05-025174 | 2/1993 |
| JP | 05-027459 | 2/1993 |
| JP | 11-119455 | 4/1999 |
| JP | 2002-302674 | 10/2002 |
| JP | 2003-327587 | 11/2003 |
| JP | 2004-093801 | 3/2004 |
| JP | 2004-093802 | 3/2004 |
| JP | 2004-152815 | 5/2004 |
| JP | 2005-154409 | 6/2005 |
| JP | 2005-189765 | 7/2005 |
| JP | 2005-209887 | 8/2005 |
| JP | 2006-028027 | 2/2006 |
| WO | 90/01480 | 2/1990 |
| WO | 96/22332 | 7/1996 |
| WO | 97/22607 | 6/1997 |
| WO | 97/22608 | 6/1997 |
| WO | 97/26301 | 7/1997 |
| WO | 98/32799 | 7/1998 |
| WO | 98/32802 | 7/1998 |
| WO | 98/49164 | 11/1998 |
| WO | 00/69829 | 11/2000 |
| WO | 02/14414 | 2/2002 |
| WO | 03/091345 | 11/2003 |
| WO | 03/104232 | 12/2003 |
| WO | 2004/029028 | 4/2004 |
| WO | 2005/047265 | 5/2005 |
| WO | 2005/070894 | 8/2005 |
| WO | 2005/070895 | 8/2005 |
| WO | 2005/078023 | 8/2005 |
| WO | 2005/092901 | 10/2005 |
| WO | 2006/021307 | 3/2006 |
| WO | 2006/037539 | 4/2006 |
| WO | 2006/050860 | 5/2006 |
| WO | 2006/093965 | 9/2006 |
| WO | 2006/115714 | 11/2006 |
| WO | 2007/074137 | 7/2007 |
| WO | 2007/093643 | 8/2007 |
| WO | 2008/091670 | 7/2008 |

OTHER PUBLICATIONS

Chen et al., "Oligothiophene-Functionalized Perylene Bisimide Sys tem: Synthesis, Characterization, and Electrochemical Polymerization Properties," *Chem. Mater.*, 17:2208-2215 (2005).

Buncel et al., "Synthesis and characterization of [3,3]- and [3,4]-perinophane," *Tetrahedron Letters*, 42:3559-3562 (2001).

Database Caplus [Online] Chemical Abstracts Service, Columbus, Ohio, US; May 12, 1984, XP002493285 retrieved from STN Database accession No. 1984:34294 abstract.

Database WPI Thomson Scientific, London, GB; AN 1983-750663 XP002493286 and JP 58 124790 A (Matsushita Electric Ind. Co. Ltd.) Jul. 25, 1983 abstract.

Facchetti et al., "Building Blocks for n-Type Organic Electronics. Regiochemically Modulated Inversion of Majority Carrier Sign in Perfluoroarene-Modified Polythiophene Conductors," *Angew. Chem. Int. Ed.*, 2003: 42, 3900-3903.

Facchetti et al., "n-Type Building Blocks for Organic Electronics: a Homologous Family of Fluorocarbon-substituted Thiophene Oligomers with High Carrier Mobility," *Adv. Mater.*, 2003: 15, 33-38.

Facchetti et al., "Tuning the Semiconducting Properties of Sexithiophene by $\alpha,\omega$-Substitution—$\alpha,\omega$-Diperfluorohexylsexithiophene: the First n-Type Sexithiophene for Thin-film Transistors," *Angew. Chem. Int. Ed.*, 2000: 39, 4547-4551.

Giaimo et al., "Excited-State Symmetry Breaking in Cofacial and Linear Dimers of a Green Perylenediimide Chlorophyll Analogue Leading to Ultrafast Charge Separation," *J. Am. Chem. Soc.*, 124: 8530-8531 (2002).

Holman et al., "Studying and Switching Electron Transfer: From the Ensemble to the Single Molecule," *J. Am. Chem. Soc.*, 126: 16126-16133 (2004).

Huttner et al., "N-type organic field effect transistors from perylene bisimide block copolymers and homopolymers," *Appl. Phys. Lett.*, 92: 093302 (2008).

Jones et al., "Cyanonaphthalene Diimide Semiconductors for Air-Stable, Flexible, and Optically Transparent n-Channel Field-Effect Transistors," *American Chemical Society*, 2007: 19 (11), 2703-2705.

Jones et al., "Tuning Orbital Energetics in Arylene Diimide Semiconductors. Materials Design for Ambient Stability of n-Type Charge Transport," *J. Am. Chem. Soc.*, 2007: 129, 15259-15278.

Kwan et al., "Electrochemistry of Langmuir-Blodgett and Self-Assembled Films Built from Oligoimides," *Langmuir*, 8:3003-3007 (1992).

Langhals et al., "Tangentially Coupled $\pi$ Systems and their Through-Space Interaction—Trichromophoric Perylene Dyes," *J. Prakt. Chem.*, 338: 654-659 (1996).

Langhals et al., "Chiral Bifluorophoric Perylene Dyes with Unusually High CD Effects—A Simple Model for the Photosynthesis Reaction Center," *Leibigs Ann./Recueil.*, 1151-1153 (1997).

Lindner et al., "Nanostructures of N-type organic semiconductor in a p-type matrix via self-assembly of block copolymers," *Macromolecules*, 37:8832-8835 (2004).

Lindner et al., "Charge Separation at Self-Assembled Nanostructured Bulk Interface in Block Copolymers," *Angew. Chem. Int. Ed.*, 45:3364-3368 (2006).

Lukas et al., "Femtosecond Optical Switching of Electron Transport Direction in Branched Donor-Acceptor Arrays," *J. Phys. Chem. B*, 104: 931-940 (2000).

Lukas et al., "Biomimetic Electron Transfer Using Low Energy Excited States: A Green Perylene-Based Analogue of Chloroophyll a," *J. Phys. Chem. B*, 106: 1299-1306 (2002).

Martyushina et al., "Searches for Nondepolarizing Short-Action Myorelaxants," *Pharm. Chem.*, 1982: 16 (7), 801-806 (English translation).

Morris at al., "Synthesis of Extended Linear Aromatics Using Tandem Diels-Alder Aromatization Reactions," *J. Org. Chem.*, 59:6484-6486 (1994).

Müller et al., "Facile synthetic approach to novel core-extended perylene carboximide dyes," *Chem. Commun.*, (2005) 4045-4046.

Rodriguez-Llorente et al., "Infrared and Raman spectra of thin solid films of 1,2-bis(propylimido perylene) ethane," *Spectrochimica Acta. Part A*, 55: 969-978 (1999).

Rodriguez-Llorente et al., "Vibrational spectra and thin solid films of a bi(propylperylenediimide)," *J. Mater. Chem.*, 8(10): 2175-2179 (1998).

Rodriguez-Llorente et al., "Spectroscopic characterization of thin solid films of a bis(chlorobenzylimidoperyleneimido)octane derivative," *J. Mater. Chem.*, 8(3): 629-632 (1998).

Rohr et al., "Liquid crystalline coronene derivatives," *J. Mater. Chem.*, 11:1789-1799 (2001).

Tauber et al., "Electron Hopping in π-Stacked Covalent and Self-Assembled Perylene Diimides Observed by ENDOR Spectroscopy," *JACS Comm.*, 128: 1782-1783 (2006).

Thalacker et al., "Hydrogen bond directed self-assembly of core-substituted naphthalene bisimides with melamines in solution and at the graphite interface," *Org. Biomol. Chem.*, 3:414-422 (2005).

* cited by examiner (a)

(b)

(a)

(b)

(a)

(b)

//page
ORGANIC SEMICONDUCTOR MATERIALS AND PRECURSORS THEREOF

CROSS REFERENCE TO RELATED APPLICATION

This application claims priority to and the benefit of U.S. Provisional Patent Application Ser. No. 60/897,257, filed on Jan. 24, 2007, the disclosure of which is incorporated by reference in its entirety.

INTRODUCTION

Organic semiconductors have attracted considerable attention in the past two decades. Progress in the fields of organic electronics and photonics has enabled demonstrations and applications of organic semiconductors as field-effect transistors (see e.g., Garnier et al. (1994), Science, 265: 1684; Dodabalapur et al. (1995), Science, 268: 270; Dimitrakopoulos et al. (1999), Science, 283: 822; Sirringhaus et al. (1999), Nature, 401: 685; and Granstroem et al. (1998), Nature, 395: 257), organic light-emitting diodes (see e.g., Tang et al. (1987), Appl. Phys. Lett., 51: 913), and photovoltaic cells (see e.g., Shaheen et al. (2001), Appl. Phys. Lett., 78: 841; Lin et al. (1997), IEEE Trans. Electron Devices, 44: 1325). In particular, organic thin film transistors (OTFTs) based on vacuum- and solution-deposited hole-transporting (p-type) organic semiconductors have exhibited field-effect mobilities similar to those of amorphous silicon thin film transistors (TFTs) (see e.g., Dimitrakopoulos et al. (2002), Adv. Mater., 14: 99; Sherwa et al. (2002), J. West Appl. Phys. Lett., 80: 1088). The attractive performance of organic semiconductors suggests that organic semiconductors could complement or replace silicon-based technologies for existing or emerging TFT applications requiring large-area coverage, structural flexibility, low temperature processing, and low manufacturing costs. Such applications include switching devices for active matrix flat panel displays based on liquid crystal pixels, organic light-emitting diodes (OLEDs), or electrophoretic ink. Other applications of OTFTs include low-end "smart" cards, electronic identification tags, electronic tickets, and sensors.

One of the most investigated p-channel semiconductors is pentacene due to the combination of its commercial availability, device performance, and environmental stability. Various research groups have reported OTFTs that incorporate vacuum-deposited thin films of pentacene, and in some instances, hole field-effect carrier mobilities exceeding 1 $cm^2$ $V^{-1}$ $s^{-1}$ have been reported (see e.g., Sirringhaus et al. (1999), Nature, 401: 685; Sherwa et al. (2002), J. West Appl. Phys. Lett., 80: 1088; and Herwig et al. (1999), Adv. Mater., 11: 480). However, for organic semiconductors to be commercially competitive, the semiconductor material as well as other TFT device material components needs to be processable by inexpensive solution-processing techniques such as spin-coating, dip-coating, solution-casting, and printing. One approach that has been used to achieve solution-processable organic semiconductors is to prepare a soluble precursor of an otherwise insoluble organic semiconductor, deposit the soluble precursor as a film, and convert the soluble precursor to the insoluble semiconductor by a thermally-promoted reaction. For pentacene, this approach was first realized by Muellen and co-workers. Muellen synthesized a soluble pentacene precursor that could be converted to pentacene by heating at 200° C. (see Afzali et al. (2002), J. Am. Chem. Soc., 124: 8812). Recently, an alternative approach for synthesizing soluble pentacene precursors was reported (see Afzali et al. (2003), Adv. Mater., 15: 2006) in which a hetero-Diels-Alder adduct of pentacene with N-sulfinylacetamide was prepared in high yield. Organic thin film transistors (OTFTs) fabricated by solution-processing of the latter afforded high field effect mobility (up to 0.8 $cm^2$ $V^{-1}$ $s^{-1}$). Recently, the same group has reported the use of another N-sulfinylamido reagent that allows solubilization of the pentacene precursor in environmentally friendly solvents such as alcohols (see Afzali et al. (2005), Synth. Metal, 155: 490).

In contrast to pentacene, sexithiophene, and few other hole-channel semiconductors, the "soluble-precursor" approach has been unexplored for n-channel semiconductor materials. Considering their greater sensitivity to chemical impurities (acting as electron traps), the synthesis of such soluble precursors of n-channel semiconductor material requires additional considerations. For instance, while ambient atmosphere usually does not hinder hole transport, the majority of n-channel organic semiconductors are inactive when oxygen and water are present during device operation. Furthermore, many n-channel materials are sensitive to the presence of chemical groups such as carbinols, silanols, and carbonyls, at the semiconductor-insulator interface.

Useful manufacturing processes that enable complementary circuit technologies will require both solution-processable p- and n-channel semiconductors. Accordingly, there is a desire in the art for new air-stable and solution-processable n-type organic semiconductors that can be integrated in various device designs including, but not limited to, complementary circuits, OTFTs, OLEDs, organic photovoltaics, photodetectors, capacitors, and sensors.

SUMMARY

In light of the foregoing, the present teachings provide organic semiconductor materials and associated devices that can address various deficiencies and shortcomings of the prior art, including those outlined above.

More specifically, the present teachings provide new n-type organic semiconductor compounds and their soluble precursors, methods for preparing these compounds and precursors, and methods for converting the soluble precursors to corresponding active semiconductor forms. To this end, claims 1-35 at the end of the description are incorporated by reference into this section.

The present teachings also provide various compositions, articles, structures, and devices that incorporate the compounds disclosed herein.

The foregoing as well as other features and advantages of the present teachings will be more fully understood from the following figures, description, and claims.

BRIEF DESCRIPTION OF THE DRAWINGS

It should be understood that the drawings described below are for illustration purposes only and are not intended to limit the scope of the present teachings in any way.

DETAILED DESCRIPTION

Figure 1:
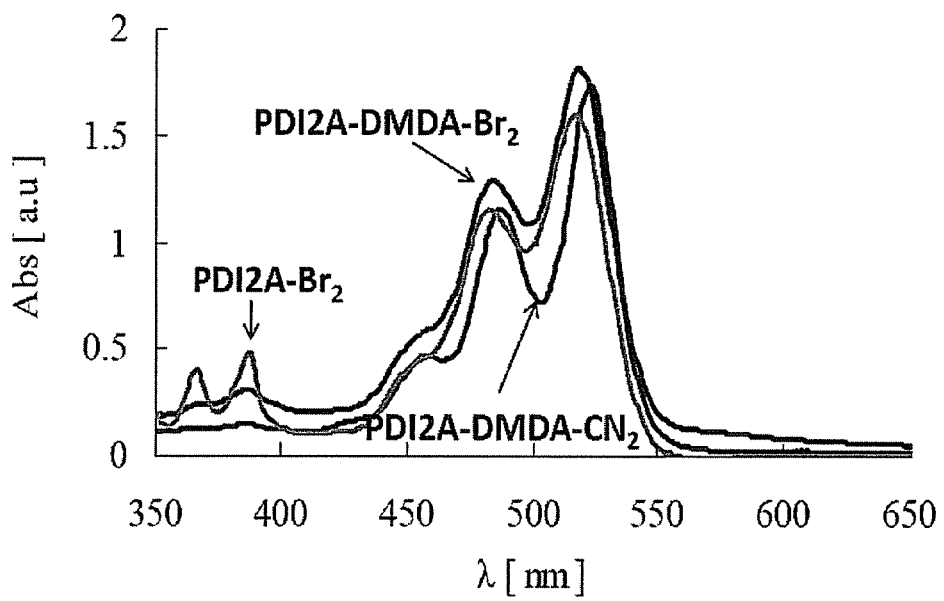
FIG. 1 provides optical absorption spectra of certain embodiments (PDI2A-$Br_2$, PDI2A-DMDA-$Br_2$ and PDI2A-DMDA-$CN_2$, all in THF) of the present teachings.

The present teachings relate to organic semiconductor compounds and their soluble precursors, methods for preparing such compounds and precursors, compositions that include such compounds and precursors, and materials, articles, structures, and devices that incorporate such compounds.

Specifically, the present teachings relate to n-type semiconductor compounds and their soluble precursors, both of which are based upon an optionally substituted rylene core.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

The use of the terms "include," "includes," "including," "have," "has," or "having" should be generally understood as open-ended and non-limiting unless specifically stated otherwise.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a 110% variation from the nominal value.

It should be understood that the order of steps or der for performing certain actions is immaterial so long as the present teachings remain operable. Moreover, two or more steps or actions may be conducted simultaneously.

As used herein, "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. Such fused ring moiety can have from 10 to 22 ring atoms, 0 to 5 of which can be heteroatoms independently selected from O, S, N, P, and Si. Any suitable ring position of the fused ring moiety can be covalently linked to the defined chemical structure. These polycyclic ring systems can be highly π-conjugated and can include, without limitation, rylenes having the formula:

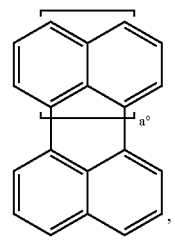

where a° can be an integer in the range of 0-3; and linear acenes having the formula:

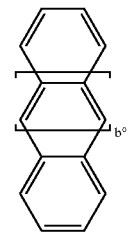

where b° can be an integer in the range of 0-4. The fused ring moiety can be optionally substituted on one or more of its rings and can include one or more bridges as disclosed herein.

As used herein, "dicarboximide" refers to a —C(O)—NH—C(O)— group, where the nitrogen atom can be substituted as disclosed herein.

As used herein, "halo" or "halogen" refers to fluoro, chloro, bromo, and iodo.

As used herein, "amino" or "amine" refers to —NRR', where R and R' independently can be selected from H, an alkyl group, an arylalkyl group, an aryl group, a cycloalkyl group, a heteroaryl group, and a cycloheteroalkyl group, and where each of the alkyl group, the arylalkyl group, the aryl group, the cycloalkyl group, the heteroaryl group, and the cycloheteroalkyl group are as defined herein and can be optionally substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy groups, and the like.

As used herein, "alkylthio" refers to an —S-alkyl group. Examples of alkylthio groups include, but are not limited to, methylthio, ethylthio, propylthio (e.g., n-propylthio and isopropylthio), t-butylthio groups, and the like.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and isopropyl), butyl (e.g., n-butyl, isobutyl, sec-butyl, tert-butyl), pentyl groups (e.g., n-pentyl, isopentyl, neopentyl), and the like. In various embodiments, an alkyl group can have 1 to 20 carbon atoms, i.e., a $C_{1-20}$ alkyl group. In some embodiments, an alkyl group can have 1 to 6 carbon atoms and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In some embodiments, alkyl groups can be substituted as disclosed herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 20 carbon atoms, for example, 1 to 10 carbon atoms (i.e., a $C_{1-10}$ haloalkyl group). Examples of haloalkyl groups include, but are not limited to, $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl." For example, a $C_{1-20}$ haloalkyl group can have the formula —$C_iH_{2i+1-j}X_j$, wherein X, at each occurrence, is F, Cl, Br, or I, i is an integer in the range of 1 to 20, and j is an integer in the range of 0 to 41, provided that j is less than or equal to 2i+1.

As used herein, "arylalkyl" refers to an -alkyl-aryl group, wherein the arylalkyl group is covalently linked to the defined chemical structure via the alkyl group. An arylalkyl group is within the definition of an -L-$C_{6-14}$ aryl group or a —Y—$C_{6-14}$ aryl group, where L and Y independently are divalent $C_{1-20}$ alkyl groups. An example of an arylalkyl group is a benzyl group (—$CH_2$—$C_6H_5$). An arylalkyl group can be optionally substituted, i.e., the aryl group and/or the alkyl group can be substituted as disclosed herein.

As used herein, "alkenyl" refers to a straight-chain or branched alkyl group having one or more carbon-carbon double bonds. Examples of alkenyl groups include, but are not limited to, ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 20 carbon atoms, i.e., a $C_{2-20}$ alkenyl group. In some embodiments, alkenyl groups can be substituted as disclosed herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include, but are not limited to, ethynyl, propynyl, butynyl, pentynyl, and the like. The one or more triple carbon-carbon bonds can be internal (such as in 2-butyne) or terminal (such as in 1-butyne). In various embodiments, an alkynyl group can have 2 to 20 carbon atoms, i.e., a $C_{2-20}$ alkynyl group. In some embodiments, alkynyl groups can be substituted as disclosed herein. An alkynyl group is generally not substituted with another alkynyl group, an alkyl group, or an alkenyl group.

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Examples of cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In various embodiments, a cycloalkyl group can have 3 to 14 carbon atoms, including 3 to 10 carbon atoms (i.e., a $C_{3-10}$ cycloalkyl group). In some embodiments, cycloalkyl groups can be substituted as disclosed herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, N and S, and optionally contains one or more double or triple bonds. In various embodiments, a cycloheteroalkyl group can have 3 to 20 ring atoms, including 3 to 14 ring atoms (i.e., a 3-14 membered cycloheteroalkyl group). One or more N or S atoms in a cycloheteroalkyl ring can be oxidized (e.g., morpholine N-oxide, thiomorpholine S-oxide, thiomorpholine S,S-dioxide). In some embodiments, nitrogen atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as disclosed herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group, as a whole, can have, for example, from 6 to 16 carbon atoms in its ring system (i.e., a $C_{6-16}$ aryl group), which can include multiple fused rings. In some embodiments, a polycyclic aryl group can have from 7 to 16 carbon atoms. The aryl group can be covalently linked to the defined chemical structure at any suitable ring position that results in a stable structure. Examples of aryl groups having only aromatic carbocyclic ring(s) include, but are not limited to, phenyl, 1-naphthyl (bicyclic), 2-naphthyl (bicyclic), anthracenyl (tricyclic), phenanthrenyl (tricyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6- bicyclic cycloheteroalkyl/aromatic ring system). Other examples of aryl groups include, but are not limited to, benzodioxanyl, benzodioxolyl, chromanyl, indolinyl groups, and the like. In some embodiments, aryl groups can be substituted as disclosed herein. In some embodiments, an aryl group can have one or more halogen substituents, and can be referred to as a "haloaryl" group. Perhaloaryl groups, i.e., aryl groups wherein all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least 1 ring heteroatom selected from O, N and S or a polycyclic ring system where at least one of the rings present in the ring system is aromatic and contains at least 1 ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, from 5 to 16 ring atoms and contain 1-5 ring heteroatoms. The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5-membered monocyclic and 5-6 bicyclic ring systems shown below:

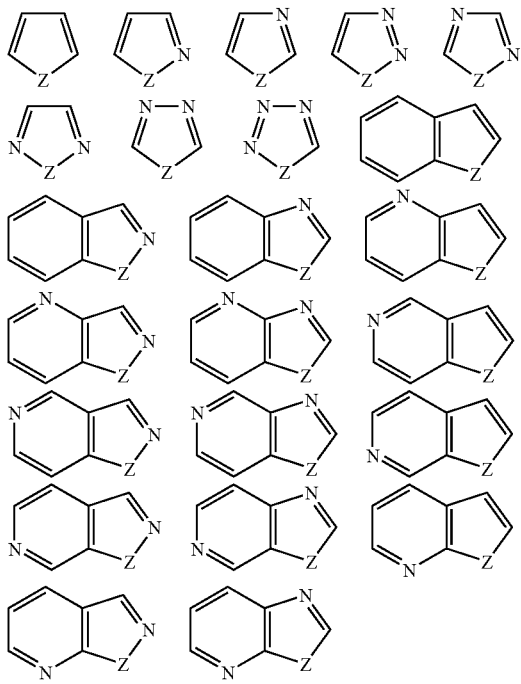

where Z is O, S, NH, N-alkyl, N-aryl, or N-(arylalkyl) (e.g., N-benzyl). Examples of heteroaryl groups include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuryl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl, and the like. Further examples of heteroaryl groups include, but are not limited to, 4,5,6,7-tetrahydroindolyl, tetrahydroquinolyl, benzothienopyridyl, benzofuropyridyl, and the like. In some embodiments, heteroaryl groups can be substituted as disclosed herein.

As used herein, a "divalent group" refers to a linking group capable of forming a covalent bond with two other moieties. For example, compounds of the present teachings can include a divalent $C_{1-20}$ alkyl group, such as, for example, a methylene group.

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein. It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halide (e.g., F, Cl, Br, I), —$NO_2$, —CN, —NC, —OH, —$OR^o$, —SH, —$SR^o$, —$S(R^o)_2^+$, —$NH_2$, —$NHR^o$, —$NR^o_2$, —$N(R^o)_3^+$, —$SO_3H$, —$SO_2R^o$, —$SO_3R^o$, —$SO_2NHR^o$, —$SO_2N(R^o)_2$, —COOH, —$COR^o$, —$COOR^o$, —$CONHR^o$, —$CON(R^o)_2$, $C_{1-10}$ haloalkyl groups, $C_{6-14}$ aryl groups, and 5-14 membered heteroaryl groups; where $R^o$ is a $C_{1-10}$ alkyl group, a $C_{2-10}$ alkenyl group, a $C_{2-10}$ alkynyl group, a $C_{1-10}$ haloalkyl group, a $C_{1-10}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted with 1-5 $R^b$ groups where $R^b$ is as defined herein.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halide (e.g., Cl, Br, I), azide ($N_3$), thiocyanate (SCN), nitro ($NO_2$), cyanate (CN), tosylate (toluenesulfonate, TsO), mesylate (methanesulfonate, MsO), brosylate (p-bromobenzenesulfonate, BsO), nosylate (4-nitrobenzenesulfonate, NsO), water ($H_2O$), ammonia ($NH_3$), and triflate (trifluoromethanesulfonate, OTf).

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

Compounds described herein can contain an asymmetric atom (also referred as a chiral center) and some of the compounds can contain one or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes and imines). It is also understood that the present teachings encompass all possible regioisomers in pure form and mixtures thereof, which can be obtained by using standard separation procedures known to those skilled in the art, including, for examples, column chromatography, thin-layer chromatography, simulated moving-bed chromatography, and high-performance liquid chromatography. For example, perylene compounds of the present teachings can include any perylene derivatives in their respective pure forms or mixtures thereof, where the perylene derivatives can be substituted with 1, 2, 3, 4, 5, 6, 7, or 8 $R^a$ groups where, $R^a$ is as defined herein.

More specifically, the perylene derivatives can include compounds having the moiety:

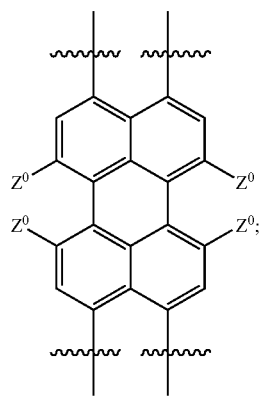

where $Z^0$, at each occurrence, can be H or $R^a$, where $R^a$ is as defined herein. In various embodiments, two of the $Z^0$ groups can be H and the other two $Z^0$ groups independently can be $R^a$, where $R^a$ is as defined herein. Accordingly, in the embodiments where two of the $Z^0$ groups are H and the other two independently are $R^a$, compounds of the present teachings can have regioisomers having the moieties:

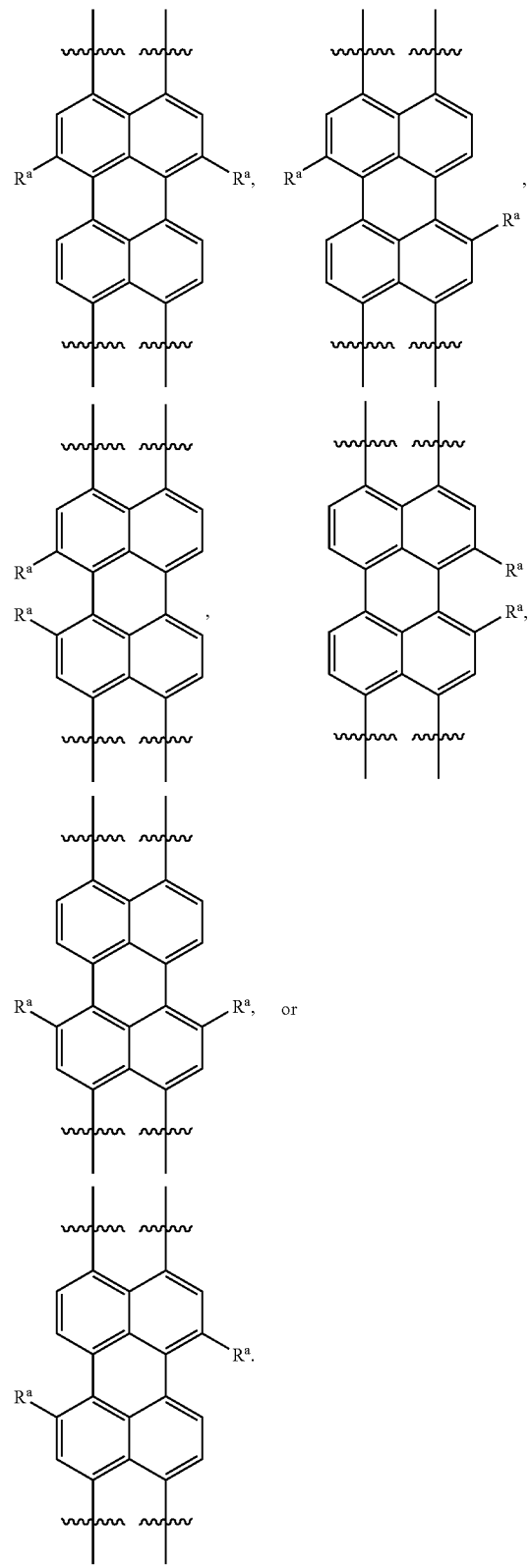

In certain embodiments, compounds of the present teachings can include regioisomers having the moieties:

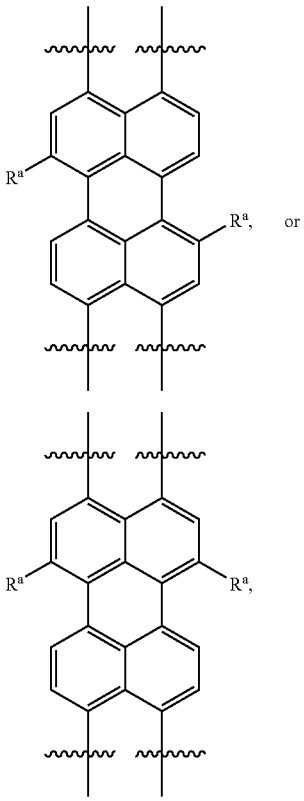

and mixtures thereof, where $R^a$ is as defined herein. Further, it is specifically contemplated that the depiction of one regioisomer includes the other regioisomers and any regioisomeric mixtures unless specifically stated otherwise. Accordingly, in particular embodiments, the use of compounds of formula i include compounds of formula II (and vice versa) and mixtures of compounds of formulae i and ii.

As used herein, a "p-type semiconducting material" or a "p-type semiconductor" refers to a semiconducting material having holes as the majority current carriers. In some embodiments, when a p-type semiconducting material is deposited on a substrate, it can provide a hole mobility in excess of about $10^{-5}$ cm$^2$/Vs. In the case of field-effect devices, a p-type semiconductor can also exhibit a current on/off ratio of greater than about 10.

As used herein, an "n-type semiconducting material" or an "n-type semiconductor" refers to a semiconducting material having electrons as the majority current carriers. In some embodiments, when an n-type semiconducting material is deposited on a substrate, it can provide an electron mobility in excess of about $10^{-5}$ cm$^2$/Vs. In the case of field-effect devices, an n-type semiconductor can also exhibit a current on/off ratio of greater than about 10.

As used herein, "field effect mobility" refers to a measure of the velocity with which charge carriers, for example, holes (or units of positive charge) in the case of a p-type semiconducting material and electrons in the case of an n-type semiconducting material, move through the material under the influence of an electric field.

At various places in the present application temperatures are disclosed in ranges. It is specifically intended that the description includes narrower ranges of temperatures within such ranges, as well as the maximum and minimum temperatures embracing such range of temperatures.

Throughout the specification, structures may or may not be presented with chemical names. Where any question arises as to nomenclature, the structure prevails.

In one aspect, the present teachings provide compounds of formula I:

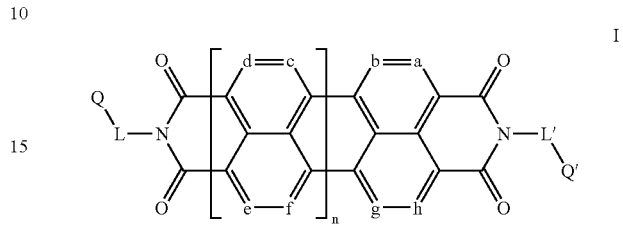

wherein:
a, b, g, and h independently are CH, CR$^a$, SiR$^b$, N, or P;
c, d, e, and f, at each occurrence, independently are CH, CR$^a$, SiR$^b$, N, or P;
L and L' independently are —Y—[SiR$^b$R$^{b'}$]—Y—, —Y—O—Y—, —[(CH$_2$)$_p$—O]$_q$—, —[O—(CH$_2$)$_p$]$_q$—, —Y—S(O)$_m$—Y—, —Y—C(O)—Y—, —Y—O—C(O)—Y—, —Y—C(O)—O—Y—, —Y—NR$^c$C(O)—Y—, —Y—C(O)NR$^c$—Y—, —Y—NR$^c$—Y—, a divalent C$_{1-20}$ alkyl group, a divalent C$_{2-20}$ alkenyl group, a divalent C$_{1-20}$ haloalkyl group, or a covalent bond;
Q and Q' independently are a fused ring moiety optionally substituted with 1-10 R$^{a'}$ groups;
R$^a$ and R$^{a'}$, at each occurrence, independently are a) halogen, b) —CN, c) —NO$_2$, d) —O—Y—R$^d$, e) —NR$^e$—Y—R$^f$, f) —N(O)R$^e$—Y—R$^f$, g) —S(O)$_m$R$^e$, h) —S(O)$_m$—O—Y—R$^d$, i) —S(O)$_m$NR$^e$—Y—R$^f$, j) —C(O)R$^e$, k) —C(O)O—Y—R$^d$, l) —C(O)NR$^e$—Y—R$^f$, m) —C(S)NR$^e$—Y—R$^f$, n) —Si(C$_{1-20}$ alkyl)$_3$, o) a C$_{1-20}$ alkyl group, p) a C$_{2-20}$ alkenyl group, q) a C$_{2-20}$ alkynyl group, r) a —Y—C$_{3-10}$ cycloalkyl group, s) a —Y—C$_{6-14}$ aryl group, t) a —Y-3-12 membered cycloheteroalkyl group, or u) a —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-4 R$^g$ groups;
R$^b$ and R$^{b'}$, at each occurrence, independently are a) H, b) a C$_{1-20}$ alkyl group, c) a —Y—C$_{6-14}$ aryl group, d) an —O—C$_{1-20}$ alkyl group, or e) an —O—Y—C$_{6-14}$ aryl group, wherein each of the C$_{1-20}$ alkyl groups and the C$_{6-14}$ aryl groups optionally is substituted with 1-4 R$^g$ groups;
R$^c$, at each occurrence, is a) H, b) a C$_{1-20}$ alkyl group, or c) a —Y—C$_{6-14}$ aryl group, wherein each of the C$_{1-20}$ alkyl group and the C$_{6-14}$ aryl group optionally is substituted with 1-4 R$^g$ groups;
R$^d$, at each occurrence, is a) H, b) —C(O)R$^e$, c) —C(O)NR$^e$R$^f$, d) —C(S)R$^e$, e) —C(S)NR$^e$R$^f$, f) a C$_{1-20}$ alkyl group, g) a C$_{2-20}$ alkenyl group, h) a C$_{2-20}$ alkynyl group, i) —Y—C$_{3-10}$ cycloalkyl group, j) —Y—C$_{6-14}$ aryl group, k) —Y-3-12 membered cycloheteroalkyl group, or l) —Y-5-14 membered heteroaryl group, wherein each of the C$_{1-20}$ alkyl group, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-4 $R^g$ groups;

$R^e$ and $R^f$, at each occurrence, independently are a) H, b) —OH, c) —SH, d) —S(O)$_2$OH, e) —C(O)OH, f) —C(O)NH$_2$, g) —C(S)NH$_2$, h) —OC$_{1-20}$ alkyl, i) —O—Y—C$_{6-14}$ aryl, j) —C(O)—C$_{1-20}$ alkyl, k) —C(O)—OC$_{1-20}$ alkyl, l) —C(S)N(C$_{1-20}$ alkyl)$_2$, m) —C(S)NH—C$_{1-20}$ alkyl, n) —C(O)NH—C$_{1-20}$ alkyl, o) —C(O)N(C$_{1-20}$ alkyl)$_2$, p) —S(O)$_m$—C$_{1-20}$ alkyl, q) —S(O)$_m$—OC$_{1-20}$ alkyl, r) —C(O)—Y—C$_{6-14}$ aryl, s) —C(O)—O—Y—C$_{6-14}$ aryl, t) —C(S)N(—Y—C$_{6-14}$ aryl)$_2$, u) —C(S)N(C$_{1-20}$ alkyl) —Y—C$_{6-14}$ aryl, v) —C(S)NH—Y—C$_{6-14}$ aryl, w) —C(O)NH—Y—C$_{6-14}$ aryl, x) —C(O)N(C$_{1-20}$ alkyl) —Y—C$_{6-14}$ aryl, y) —C(O)N(Y—C$_{6-14}$ aryl)$_2$, z) —S(O)$_m$—Y—C$_{6-14}$ aryl, aa) —S(O)$_m$—O—Y—C$_{6-14}$ aryl, ab) a C$_{1-20}$ alkyl group, ac) a C$_{2-20}$ alkenyl group, ad) a C$_{2-20}$ alkynyl group, ae) —Y—C$_{3-10}$ cycloalkyl group, af) —Y—C$_{6-14}$ aryl group, ag) —Y-3-12 membered cycloheteroalkyl group, or ah) —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl groups, the 3-12 membered cycloheteroalkyl group, and the 5-14 membered heteroaryl group optionally is substituted with 1-4 $R^g$ groups;

$R^g$, at each occurrence, is a) halogen, b) —CN, c) —NO$_2$, d) oxo, e) —OH, f) —NH$_2$, g) —NH(C$_{1-20}$ alkyl), h) —N(C$_{1-20}$ alkyl)$_2$, i) —NH(C$_{1-6}$ alkyl-C$_{6-14}$ aryl), j) —N(C$_{1-20}$ alkyl)(C$_{1-6}$ alkyl-C$_{6-14}$ aryl), k) —N(C$_{1-6}$ alkyl-C$_{6-14}$ aryl)$_2$, l) —S(O)$_m$H, m) —S(O)$_m$—C$_{1-20}$ alkyl, n) —S(O)$_2$OH, o) —S(O)$_m$—OC$_{1-20}$ alkyl, p) —CHO, q) —C(O)—C$_{1-20}$ alkyl, r) —C(O)OH, s) —C(O)—OC$_{1-20}$ alkyl, t) —C(O)NH$_2$, u) —C(O)NH—C$_{1-20}$ alkyl, v) —C(O)N(C$_{1-20}$ alkyl)$_2$, w) —C(O)NH(C$_{1-6}$ alkyl-C$_{6-14}$ aryl), x) —C(O)N(C$_{1-20}$ alkyl)(C$_{1-6}$ alkyl-C$_{6-14}$ aryl), y) —C(O)N(C$_{1-6}$ alkyl-C$_{6-14}$ aryl)$_2$, z) —C(S)NH$_2$, aa) —C(S)NH—C$_{1-20}$ alkyl, ab) —C(S)N(C$_{1-20}$ alkyl)$_2$, ac) —C(S)NH(C$_{1-6}$ alkyl-C$_{6-14}$ aryl), ad) —C(S)N(C$_{1-20}$ alkyl)(C$_{1-6}$ alkyl-C$_{6-14}$ aryl), ae) —C(S)N(C$_{1-6}$ alkyl-C$_{6-14}$ aryl)$_2$, af) —S(O)$_m$NH$_2$, ag) —S(O)$_m$ NH(C$_{1-20}$ alkyl), ah) —S(O)$_m$N(C$_{1-20}$ alkyl)$_2$, ai) —S(O)$_m$NH(C$_{1-6}$ alkyl-C$_{6-14}$ aryl), aj) —S(O)$_m$N(C$_{1-20}$ alkyl)(C$_{1-6}$ alkyl-C$_{6-14}$ aryl), ak) —S(O)$_m$N(C$_{1-6}$ alkyl-C$_{6-14}$ aryl)$_2$, al) —Si(C$_{1-20}$ alkyl)$_3$, am) a C$_{1-20}$ alkyl group, an) a C$_{2-20}$ alkenyl group, ao) a C$_{2-10}$ alkynyl group, ap) a C$_{1-20}$ alkoxy group, aq) a C$_{1-20}$ alkylthio group, ar) a C$_{1-20}$ haloalkyl group, as) a C$_{3-10}$ cycloalkyl group, at) a C$_{6-14}$ aryl group, au) a 3-12 membered cycloheteroalkyl group, or av) a 5-14 membered heteroaryl group;

Y, at each occurrence, is a) a divalent C$_{1-20}$ alkyl group, b) a divalent C$_{1-20}$ haloalkyl group, or c) a covalent bond;

m, at each occurrence, is 0, 1 or 2;

p, at each occurrence, is 1, 2, 3, 4, 5, 6, 7, 8, 9 or 10;

q, at each occurrence, is 1, 2, 3, 4, 5, 6, 7, 8, 9 or 10; and n is 0, 1 or 2.

In various embodiments, a, b, g, and h independently can be selected from CH, CR$^a$ and N, and c, d, e, and f, at each occurrence, independently can be selected from CH, CR$^a$ and N, where R$^a$ is as defined herein.

In various embodiments, compounds of formula I can be represented by formula I':

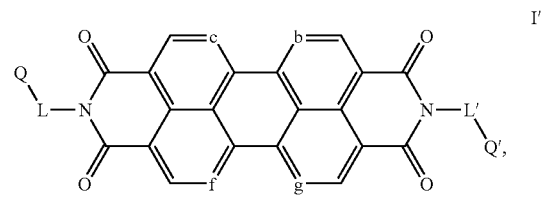

where L, L', Q, Q', b, c, f, and g are as defined herein. In some embodiments, b, c, f and g independently can be selected from CH and CR$^a$, where R$^a$ is as defined herein. For example, R$^a$ can be selected from Br, Cl, F, and CN. In certain embodiments, each of b, c, f, and g can be CH. In certain embodiments, b, c, f, and g independently can be C(Br) or C(CN). In certain embodiments, two of b, c, f, and g can be CH and the other two of b, c, f, and g independently can be selected from C(Br) and C(CN). In particular embodiments, each of c and g can be CH, and b and f independently can be C(Br) or C(CN). In particular embodiments, each of b and f can be CH, and c and g independently can be C(Br) or C(CN). In particular embodiments, each of c and f can be CH, and b and g independently can be C(Br) or C(CN). In particular embodiments, each of b and g can be CH, and c and f independently can be C(Br) or C(CN).

In various embodiments, L and L' independently can be selected from —(CH$_2$)$_p$—O—(CH$_2$)$_p$—, —[(CH$_2$)$_p$—O]$_q$—, —(CH$_2$)$_q$—, —C$_q$X$_{2q}$—, and a covalent bond, where X can be a halogen (e.g., F), p can be 1, 2, or 3, and q is as defined herein. In some embodiments, L and L' independently can be a covalent bond, —CH$_2$—, —CH$_2$CH$_2$—, or —CH$_2$CH$_2$CH$_2$—.

In various embodiments, Q and Q' independently can be a fused ring moiety having at least three fused rings, where at least one of the three fused rings is aromatic. For example, Q and Q' independently can be selected from:

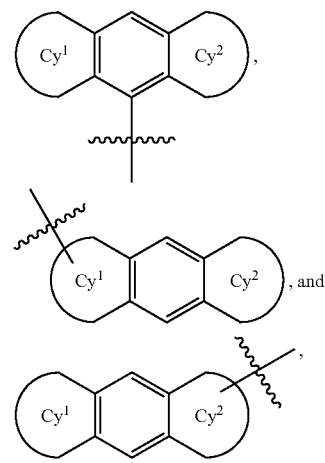

where Cy$^1$ and Cy$^2$, at each occurrence, independently can be an aromatic cyclic group or a non-aromatic cyclic group, each of the aromatic cyclic group and the non-aromatic cyclic group having 5 or 6 ring atoms, 0 to 4 of which can be heteroatoms independently selected from O, S, N, P, and Si. Such fused ring moiety (on one or more of its rings) can optionally be substituted with 1-10 R$^{a'}$ groups, where R$^{a'}$ is as defined herein.

In some embodiments, each of Q and Q' can be an anthracenyl group optionally substituted with 1-10 $R^{a'}$ groups. In certain embodiments, Q and Q' independently can be selected from:

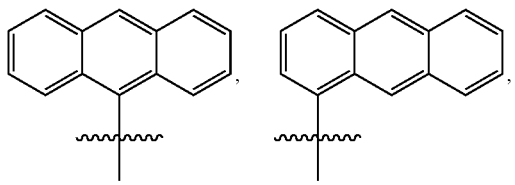

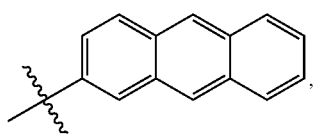

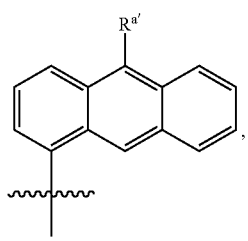

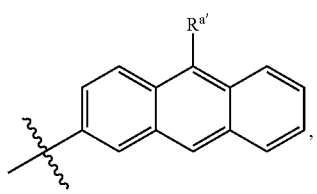

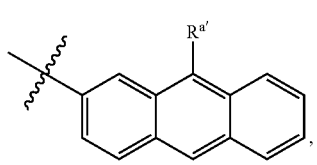

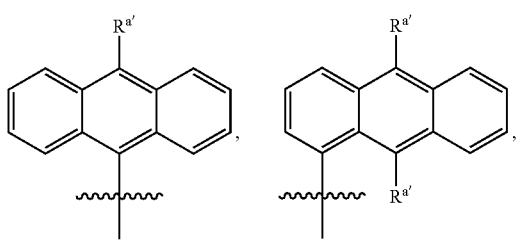

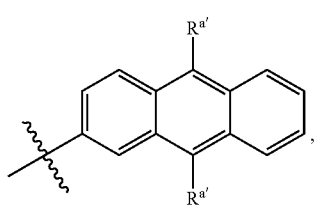

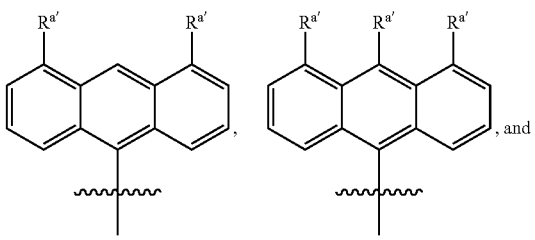

, and

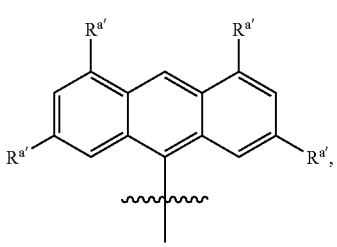

where $R^{a'}$ is as defined herein. For example, $R^{a'}$, at each occurrence, can be a halogen (e.g., F), —CN, —NH$_2$, —NH(C$_{1-20}$ alkyl), —N(C$_{1-20}$ alkyl)$_2$, —NH(C$_{1-6}$ alkyl-C$_{6-14}$ aryl), —N(C$_{1-20}$ alkyl)(C$_{1-6}$ alkyl-C$_{6-14}$ aryl), —N(C$_{1-6}$ alkyl-C$_{6-14}$ aryl)$_2$, —CHO, —C(O)—C$_{1-20}$ alkyl, —C(O)OH, —C(O)—OC$_{1-20}$ alkyl, or a straight chain or branched C$_{1-10}$ alkyl group.

In various embodiments, the -L-Q group and the -L'-Q' group can be different. In various embodiments, the -L-Q group and the -L'-Q' group can be the same.

Compounds of the present teachings can be prepared in accordance with the procedures outlined in Scheme 1 below, from commercially available starting materials, compounds known in the literature or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Scheme 1

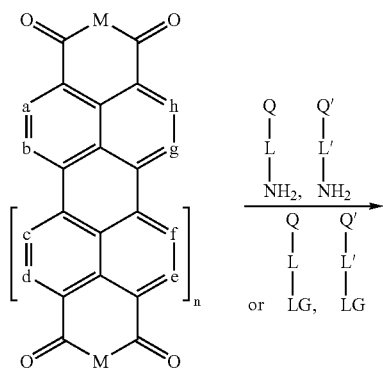

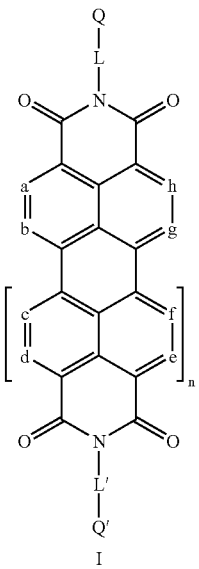

M = O, S, NH where LG is a leaving group; and L, L', Q, Q', a, b, c, d, e, f, g, h, and n are as defined herein.

As shown in Scheme 1, an optionally core-substituted rylene anhydride (or thioanhydride) can be reacted with an appropriate amine to provide compounds of formula I. Alternatively, an unfunctionalized, optionally core-substituted, rylene bis(dicarboximide), i.e., M being NH, can be reacted with a compound having the formula Q-L-LG (or Q'-L'-LG), where LG can be a leaving group, including, for example, Br, Cl, TsO, MsO, BsO, NsO, and OTf, to provide compounds of formula I.

Examples of compounds of formula I include, but are not limited to, the compounds presented in Table 1 below.

TABLE 1

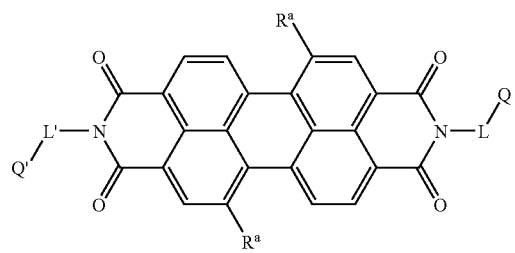

| No. | Name | -L-Q/-L'-Q' | $R^a$ |
|---|---|---|---|
| 1 | N,N'-bis(9-anthracenyl)-1,7-dibromoperylene-3,4:9,10-bis(dicarboximide) (PDI0A-Br$_2$) | 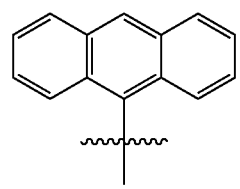 | Br |

TABLE 1-continued

| No. | Name | -L-Q/-L'-Q' | R$^a$ |
|---|---|---|---|
| 2 | N,N'-bis(9-anthracenyl)-1,7-dicyanoperylene-3,4:9,10-bis(dicarboximide) (PDI0A-CN$_2$) | (9-anthracenyl) | CN |
| 3 | N,N'-bis(anthracen-9-ylmethyl)-1,7-dibromoperylene-3,4:9,10-bis(dicarboximide) (PDI1A-Br$_2$) | (anthracen-9-ylmethyl) | Br |
| 4 | N,N'-bis(anthracen-9-ylmethyl)-1,7-dicyanoperylene-3,4:9,10-bis(dicarboximide) (PDI1A-CN$_2$) | (anthracen-9-ylmethyl) | CN |
| 5 | N,N'-bis(2-(anthracen-9-yl)-ethyl)-1,7-dibromoperylene-3,4:9,10-bis(dicarboximide) (PDI2A-Br$_2$) | 2-(anthracen-9-yl)ethyl | Br |
| 6 | N,N'-bis(2-(anthracen-9-yl)-ethyl)-1,7-dicyanoperylene-3,4:9,10-bis(dicarboximide) (PDI2A-CN$_2$) | 2-(anthracen-9-yl)ethyl | CN |

TABLE 1-continued

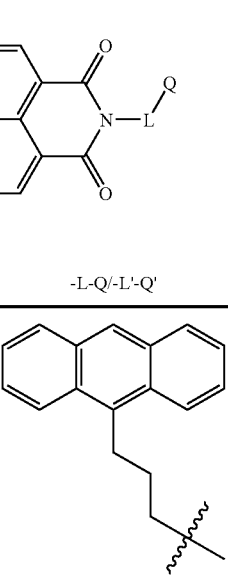

| No. | Name | -L-Q/-L'-Q' | $R^a$ |
|-----|------|-------------|-------|
| 7 | N,N'-bis(3-(anthracen-9-yl)-propyl)-1,7-dibromoperylene-3,4:9,10-bis(dicarboximide) (PDI3A-Br$_2$) | 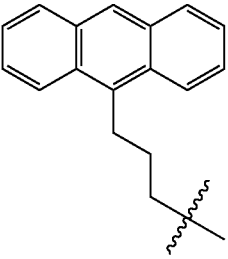 | Br |
| 8 | N,N'-bis(3-(anthracen-9-yl)-propyl)-1,7-dicyanoperylene-3,4:9,10-bis(dicarboximide) (PDI3A-CN$_2$) | 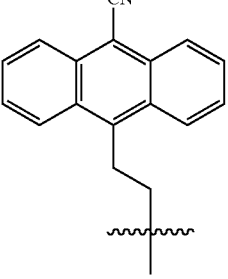 | CN |
| 9 | N,N'-bis(2-(10-cyano-anthracen-9-yl)-ethyl)-1,7-dicyanoperylene-3,4:9,10-bis(dicarboximide) | 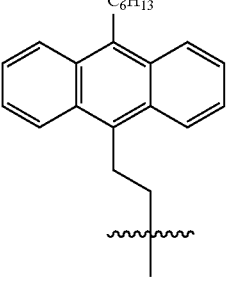 | CN |
| 10 | N,N'-bis(2-(10-hexyl-anthracen-9-yl)-ethyl)-1,7-dicyanoperylene-3,4:9,10-bis(dicarboximide) | 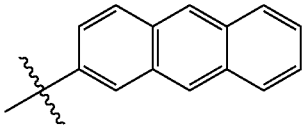 | CN |
| 11 | N,N'-bis(2-anthracenyl)-1,7-dicyanoperylene-3,4:9,10-bis(dicarboximide) |  | CN |

TABLE 1-continued

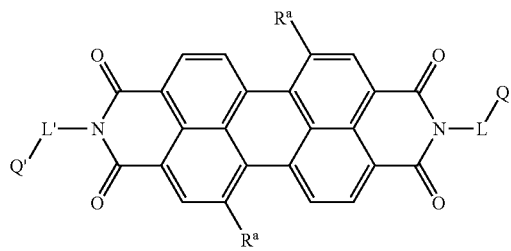

| No. | Name | -L-Q/-L'-Q' | $R^a$ |
|---|---|---|---|
| 12 | N,N'-bis(3-(anthracen-2-yl)-propyl)-1,7-dicyanoperylene-3,4:9,10-bis(dicarboximide) | 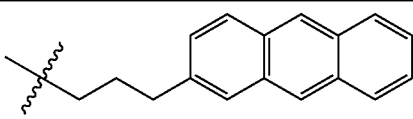 | CN |

Compounds of formula I, including but not limited to those of formula I', can be used to prepare semiconductor materials (e.g., compositions and composites), which in turn can be used to fabricate various organic electronic articles, structures, and devices. In some embodiments, semiconductor materials incorporating one or more compounds of the present teachings can exhibit n-type semiconducting activity.

Another aspect of the present teachings relates to soluble precursors of compounds of formula I. In various embodiments, the soluble precursors can be represented by formula II:

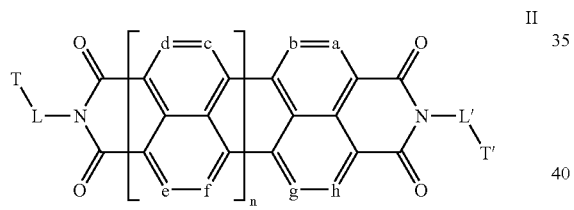

where T and T' independently are a fused ring moiety optionally substituted with 1-10 $R^{a'}$ groups and the fused ring moiety includes at least one bridged moiety having the formula:

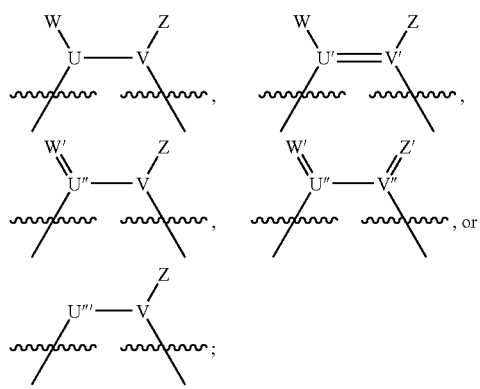

where U and V, at each occurrence, independently are CH, $CR^h$, $SiR^i$, N or P,
U', U'', V' and V'' independently are C or Si,
U''' is O, $S(O)_m$, or Se,
W and Z, at each occurrence, independently are H or $R^{h'}$, or
W and Z, together with U and V, form a $C_{3-10}$ cycloalkyl group or a 3-12 membered cycloheteroalkyl group, wherein each of the $C_{3-10}$ cycloalkyl group and the 3-12 membered cycloheteroalkyl group optionally is substituted with 1-4 $R^n$ groups,
W' and Z', at each occurrence, independently are O, $CR^jR^{j'}$, or $NR^m$,
$R^h$ and $R^{h'}$, at each occurrence, independently are a) halogen, b) —CN, c) —$NO_2$, d) —O—Y—$R^k$, e) —$NR^l$—Y—$R^m$, f) —N(O)$R^l$—Y—$R^m$, g) —$S(O)_mR^i$, h) —$S(O)_m$O—Y—$R^k$, i) —$S(O)_mNR^l$—Y—$R^m$, j) —$C(O)R^i$, k) —C(O)O—Y—$R^k$, l) —$C(O)NR^l$—Y—$R^m$, m) —$C(S)NR^l$—Y—$R^m$, n) —$Si(C_{1-20}$ alkyl$)_3$, o) a $C_{1-20}$ alkyl group, p) a $C_{2-20}$ alkenyl group, q) a $C_{2-20}$ alkynyl group, r) a —Y—$C_{3-10}$ cycloalkyl group, s) a —Y—$C_{6-14}$ aryl group, t) a —Y-3-12 membered cycloheteroalkyl group, or u) a —Y-5-14 membered heteroaryl group, wherein each of the $C_{1-20}$ alkyl groups, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group optionally is substituted with 1-4 $R^n$ groups,
$R^i$, at each occurrence, is a) H, b) a $C_{1-20}$ alkyl group, c) a —Y—$C_{6-14}$ aryl group, d) an —O—$C_{1-20}$ alkyl group, or e) an —O—Y—$C_{6-14}$ aryl group, wherein each of the $C_{1-20}$ alkyl groups and the $C_{6-14}$ aryl groups optionally is substituted with 1-4 $R^n$ groups,
$R^j$ and $R^{j'}$, at each occurrence, independently are a) H, b) halogen, c) —CN, d) —CHO, e) —C(O)—O$C_{1-20}$ alkyl, f) a $C_{1-20}$ alkyl group, or g) a —Y—$C_{6-14}$ aryl group, wherein each of the $C_{1-20}$ alkyl groups and the $C_{6-14}$ aryl group optionally is substituted with 1-4 $R^n$ groups,
$R^k$, at each occurrence, is a) H, b) —C(O)$R^e$, c) —C(O)$NR^eR^f$, d) —C(S)$R^e$, e) —C(S)$NR^eR^f$, f) a $C_{1-20}$ alkyl group, g) a $C_{2-20}$ alkenyl group, h) a $C_{2-20}$ alkynyl group, i) —Y—$C_{3-10}$ cycloalkyl group, j) —Y—$C_{6-14}$ aryl group, k) —Y-3-12 membered cycloheteroalkyl group, or l) —Y-5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group optionally is substituted with 1-4 $R^n$ groups, $R^l$ and $R^m$, at each occurrence, independently are a) H, b) —OH, c) —SH, d) —S(O)$_2$OH, e) —C(O)OH, f) —C(O)NH$_2$, g) —C(S)NH$_2$, h) —OC$_{1-20}$ alkyl, i) —O—Y—C$_{6-14}$ aryl, j) —C(O)—C$_{1-20}$ alkyl, k) —C(O)—OC$_{1-20}$ alkyl, l) —C(S)N(C$_{1-20}$ alkyl)$_2$, m) —C(S)NH—C$_{1-20}$ alkyl, n) —C(O)NH—C$_{1-20}$ alkyl, o) —C(O)N(C$_{1-20}$ alkyl)$_2$, p) —S(O)$_m$—C$_{1-20}$ alkyl, q) —S(O)$_m$—OC$_{1-20}$ alkyl, r) —C(O)—Y—C$_{6-14}$ aryl, s) —C(O)—O—Y—C$_{6-14}$ aryl, t) —C(S)N(—Y—C$_{6-14}$ aryl)$_2$, u) —C(S)N(C$_{1-20}$ alkyl) —Y—C$_{6-14}$ aryl, v) —C(S)NH—Y—C$_{6-14}$ aryl, w) —C(O)NH—Y—C$_{6-14}$ aryl, x) —C(O)N(C$_{1-20}$ alkyl) —Y—C$_{6-14}$ aryl, y) —C(O)N(Y—C$_{6-14}$ aryl)$_2$, z) —S(O)$_m$—Y—C$_{6-14}$ aryl, aa) —S(O)$_m$—O—Y—C$_{6-14}$ aryl, ab) a C$_{1-20}$ alkyl group, ac) a C$_{2-20}$ alkenyl group, ad) a C$_{2-20}$ alkynyl group, ae) —Y—C$_{3-10}$ cycloalkyl group, af) —Y—C$_{6-14}$ aryl group, ag) —Y-3-12 membered cycloheteroalkyl group, or ah) —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl groups, the 3-12 membered cycloheteroalkyl group, and the 5-14 membered heteroaryl group optionally is substituted with 1-4 $R''$ groups;

$R''$, at each occurrence, is a) halogen, b) —CN, c) —NO$_2$, d) oxo, e) —OH, f) —NH$_2$, g) —NH(C$_{1-20}$ alkyl), h) —N(C$_{1-20}$ alkyl)$_2$, i) —NH(C$_{1-6}$ alkyl-C$_{6-14}$ aryl), j) —N(C$_{1-20}$ alkyl)(C$_{1-6}$ alkyl-C$_{6-14}$ aryl), k) —N(C$_{1-6}$ alkyl-C$_{6-14}$ aryl)$_2$, l) —S(O)$_m$H, m) —S(O)$_m$—C$_{1-20}$ alkyl, n) —S(O)$_2$OH, o) —S(O)$_m$—OC$_{1-20}$ alkyl, p) —CHO, q) —C(O)—C$_{1-20}$ alkyl, r) —C(O)OH, s) —C(O)—OC$_{1-20}$ alkyl, t) —C(O)NH$_2$, u) —C(O)NH—C$_{1-20}$ alkyl, v) —C(O)N(C$_{1-20}$ alkyl)$_2$, w) —C(O)NH(C$_{1-6}$ alkyl-C$_{6-14}$ aryl), x) —C(O)N(C$_{1-20}$ alkyl)(C$_{1-6}$ alkyl-C$_{6-14}$ aryl), y) —C(O)N(C$_{1-6}$ alkyl-C$_{6-14}$ aryl)$_2$, z) —C(S)NH$_2$, aa) —C(S)NH—C$_{1-20}$ alkyl, ab) —C(S)N(C$_{1-20}$ alkyl)$_2$, ac) —C(S)NH(C$_{1-6}$ alkyl-C$_{6-14}$ aryl), ad) —C(S)N(C$_{1-20}$ alkyl)(C$_{1-6}$ alkyl-C$_{6-14}$ aryl), ae) —C(S)N(C$_{1-6}$ alkyl-C$_{6-14}$ aryl)$_2$, af) —S(O)$_m$NH$_2$, ag) —S(O)$_m$NH(C$_{1-20}$ alkyl), ah) —S(O)$_m$N(C$_{1-20}$ alkyl)$_2$, ai) —S(O)$_m$NH(C$_{1-6}$ alkyl-C$_{6-14}$ aryl), aj) —S(O)$_m$N(C$_{1-20}$ alkyl)(C$_{1-6}$ alkyl-C$_{6-14}$ aryl), ak) —S(O)$_m$N(C$_{1-6}$ alkyl-C$_{6-14}$ aryl)$_2$, al) —Si(C$_{1-20}$ alkyl)$_3$, am) a C$_{1-20}$ alkyl group, an) a C$_{2-20}$ alkenyl group, ao) a C$_{2-10}$ alkynyl group, ap) a C$_{1-20}$ alkoxy group, aq) a C$_{1-20}$ alkylthio group, ar) a C$_{1-20}$ haloalkyl group, as) a C$_{3-10}$ cycloalkyl group, at) a C$_{6-14}$ aryl group, au) a 3-12 membered cycloheteroalkyl group, or av) a 5-14 membered heteroaryl group; and L, L', $R^a$, Y, a, b, c, d, e, f, g, h, m and n are as defined herein.

In some embodiments, a, b, g, and h independently can be selected from CH, CR$^a$ and N, and c, d, e, and f, at each occurrence, independently can be selected from CH, CR$^a$ and N, where $R^a$ is as defined herein. In certain embodiments, compounds of formula II can be represented by formula II':

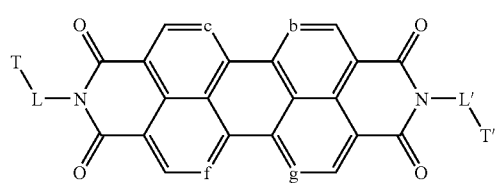

II' where L, L', T, T', b, c, f, and g are as defined herein. In particular embodiments, b, c, f and g independently can be selected from CH and CR$^a$, where $R^a$ is as defined herein. For example, $R^a$ can be selected from Br, Cl, F, and CN. In certain embodiments, each of b, c, f, and g can be CH. In certain embodiments, b, c, f, and g independently can be C(Br) or C(CN). In certain embodiments, two of b, c, f, and g can be CH and the other two of b, c, f, and g independently can be selected from C(Br) and C(CN). In particular embodiments, each of c and g can be CH, and b and f independently can be C(Br) or C(CN). In particular embodiments, each of b and f can be CH, and c and g independently can be C(Br) or C(CN). In particular embodiments, each of c and f can be CH, and b and g independently can be C(Br) or C(CN). In particular embodiments, each of b and g can be CH, and c and f independently can be C(Br) or C(CN).

In some embodiments, L and L' independently can be selected from —(CH$_2$)$_p$—O—(CH$_2$)$_p$—, —[(CH$_2$)$_p$—O]$_q$—, —(CH$_2$)$_q$—, —C$_q$X$_{2q}$—, and a covalent bond, where X can be a halogen (e.g., F), p can be 1, 2, or 3, and q is as defined herein. In certain embodiments, L and L', independently can be a covalent bond, —CH$_2$—, —CH$_2$CH$_2$—, or —CH$_2$CH$_2$CH$_2$—.

In some embodiments, T and T' independently can be a fused ring moiety having at least four fused rings. For example, T and T' independently can be selected from:

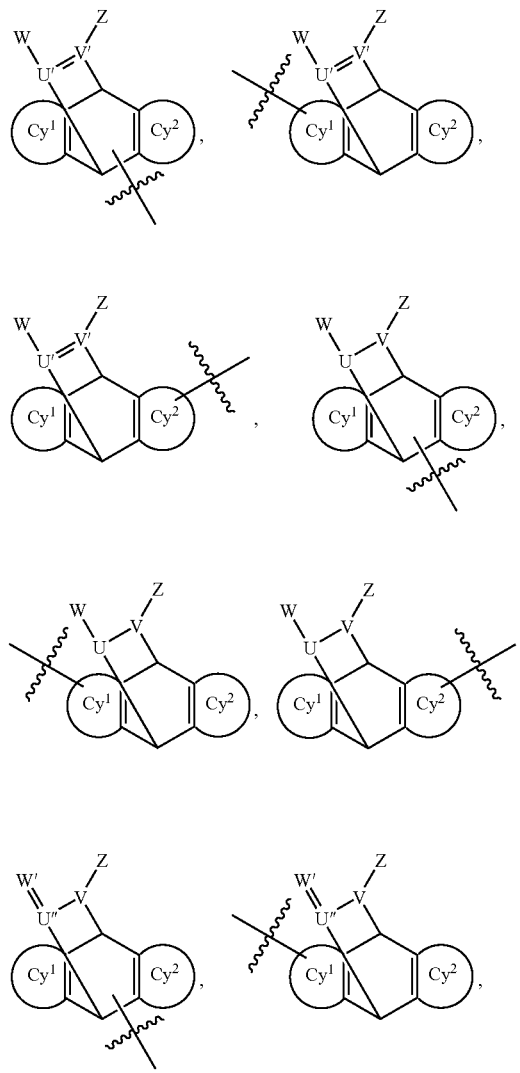

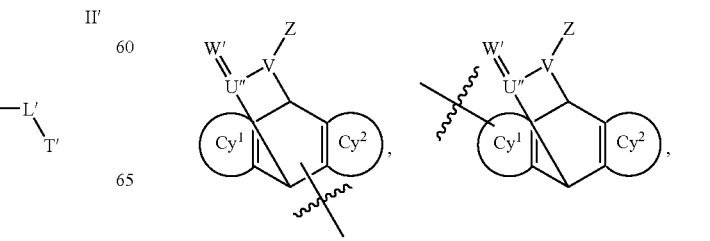

-continued

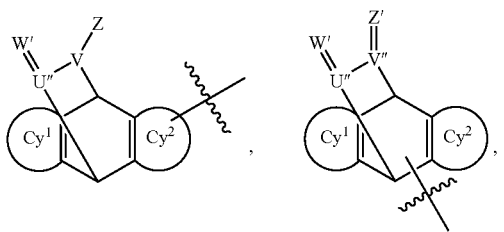

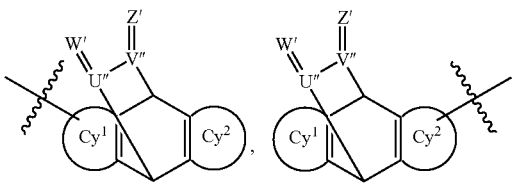

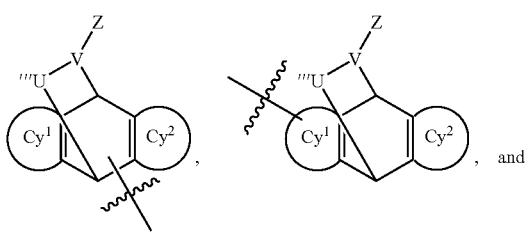

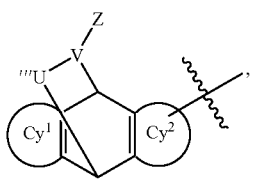

where Cy$^1$ and Cy$^2$, at each occurrence, independently can be an aromatic cyclic group or a non-aromatic cyclic group, and each of the aromatic cyclic group and the non-aromatic cyclic group can include 5 or 6 ring atoms, 0 to 4 of which can be heteroatoms independently selected from O, S, N, P, and Si; and U, U', U'', U''', V, V', V'', W, W', Z and Z' are as defined herein. Such fused ring moiety (on one or more of its rings) can be optionally substituted with 1-10 R$^{a'}$ groups, where R$^{a'}$ is as defined herein.

In certain embodiments, T and T' independently can be selected from:

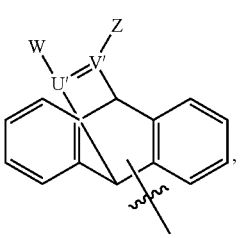

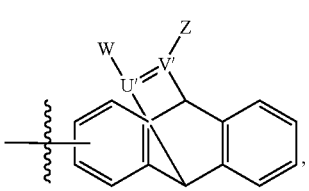

-continued

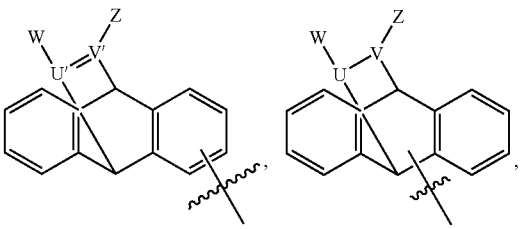

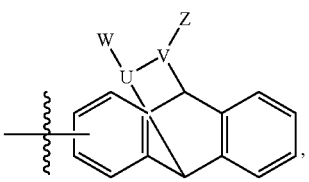

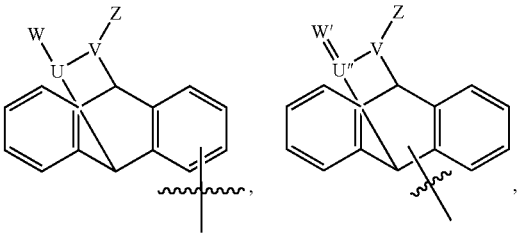

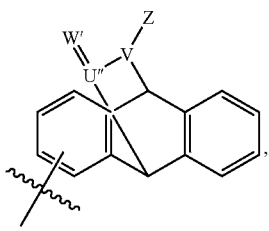

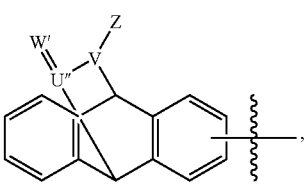

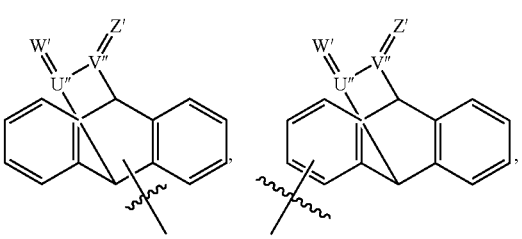

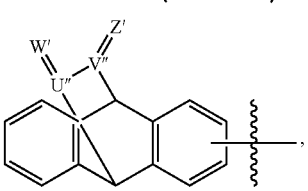

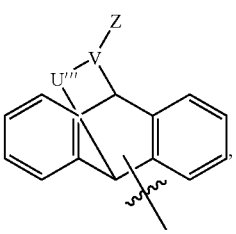

-continued

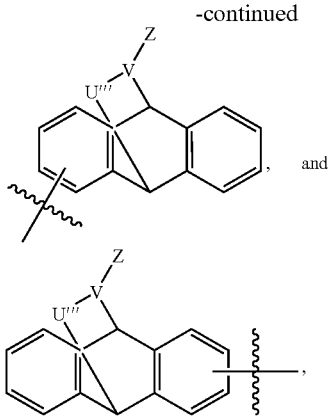

where each of these groups can be optionally substituted with 1-10 $R^{a'}$ groups, and $R^{a'}$, U, U', U", U''', V, V', V", W, W', Z and Z' are as defined herein. For example, these groups can be the product of a Diels-Alder reaction, where an optionally substituted anthracenyl group can be reacted with an appropriate dienophile to produce the bridged moiety:

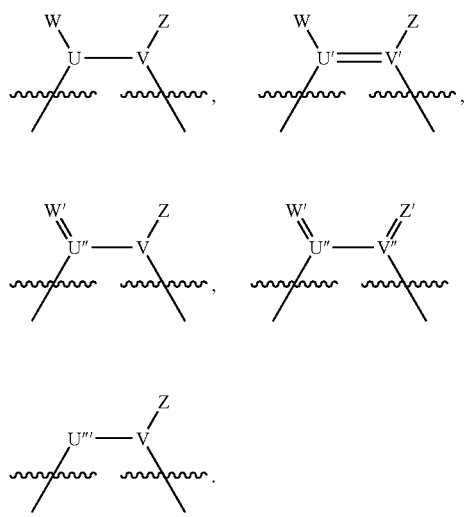

In some embodiments, U', U", V' and V" can be C; U''' can be O, S, or S(O); U and V independently can be CH, $CR^h$, or N; and $R^h$, at each occurrence, independently can be selected from —CN, —CHO, —C(O)—$C_{1-10}$ alkyl, —S(O)$_2$—$OC_{1-10}$ alkyl, a $C_{1-10}$ alkyl group, $C_{1-10}$ haloalkyl group, and a $C_{6-14}$ aryl group. In some embodiments, W and Z independently can be selected from H, —CN, —CHO, —C(O)—$OC_{1-10}$ alkyl, —S(O)$_2$—$OC_{1-10}$ alkyl, a $C_{1-10}$ alkyl group, a $C_{1-10}$ haloalkyl group, and a $C_{6-14}$ aryl group. For example, W and Z independently can be selected from H, —CN, —CHO, —C(O)OCH$_3$, —S(O)$_2$OCH$_3$, a methyl group, CF$_3$, and a phenyl group. In some embodiments, W' and Z' independently can be selected from O, CH$_2$, CHF, CF$_2$, C(CN)$_2$, CH(CN), and C(CF$_3$)$_2$.

In some embodiments, U and V, together with W and Z, can form an optionally substituted $C_{3-10}$ cycloalkyl group or an optionally substituted 3-12 membered cycloheteroalkyl group. In certain embodiments, the $C_{3-10}$ cycloalkyl group and the 3-12 membered cycloheteroalkyl group can be selected from a cyclohexenyl group, a tetrahydrofuranyl group, a 1,3-dioxolanyl group, a pyrrolidinyl group, a pyrazolidinyl group, a triazolidinyl group, and a bicyclo[2.2.1]heptanyl group, and each of these groups can be optionally substituted with 1-4 R" groups, where R" is as defined herein. For example, R" can be an oxo group, a methyl group, or a phenyl group.

In various embodiments, the -L-T group and the -L'-T' group can be different. In various embodiments, the -L-T group and the -L'-T' group can be the same.

Compounds of formula II can be prepared following the general synthetic route illustrated in Scheme 2 below.

Scheme 2

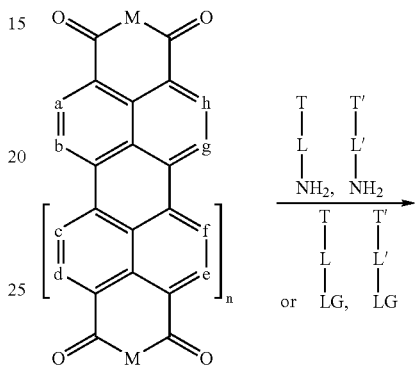

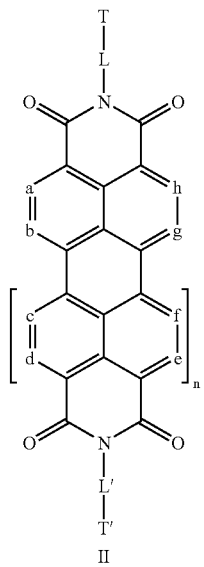

M = O, S, NH

II where LG is a leaving group; and L, L', T, T', a, b, c, d, e, f, g, h, and n are as defined herein.

As shown in Scheme 2, an optionally core-substituted rylene anhydride (or thioanhydride) can be reacted with an appropriate amine to provide compounds of formula II. Alternatively, an unfunctionalized, optionally core-substituted, rylene bis(dicarboximide) can be reacted with a compound having the formula T-L-LG (or T'-L'-LG), where LG is a leaving group such as, but not limited to, Br, Cl, TsO, MsO, BsO, NsO, and OTf, to provide compounds of formula II.

Examples of compounds of formula II include, but are not limited to, the compounds presented in Table 2 below.

TABLE 2

| No. | Name | -L-T/-L'-T' | R^a |
|---|---|---|---|
| 13 | N,N'-bis[9',10'-dihydro-9',10'-(1",2"-dicarbomethoxy)-etheno-anthracene-9'-yl]-1,7-dibromoperylene-3,4:9,10-bis(dicarboximide) PDI0A-DMDA-Br$_2$ | | Br |
| 14 | N,N'-bis[9',10'-dihydro-9',10'-(1",2"-dicarbomethoxy)-etheno-anthracene-9'-yl]-1,7-dicyanoperylene-3,4:9,10-bis(dicarboximide) PDI0A-DMDA-CN$_2$ | | CN |
| 15 | N,N'-bis[9',10'-dihydro-9',10'-(1",2"-dicarbomethoxy)-etheno-anthracene-9'-yl-methyl]-1,7-dibromoperylene-3,4:9,10-bis(dicarboximide) PDI1A-DMDA-Br$_2$ | | Br |
| 16 | N,N'-bis[9',10'-dihydro-9',10'-(1",2"-dicarbomethoxy)-etheno-anthracene-9'-yl-methyl]-1,7-dicyanoperylene-3,4:9,10-bis(dicarboximide) PDI1A-DMDA-CN$_2$ | | CN |

TABLE 2-continued

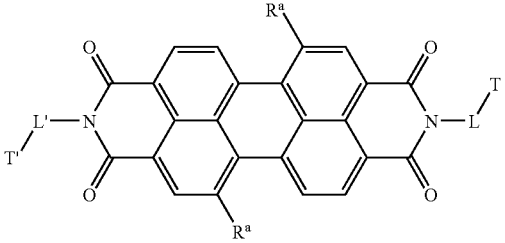

| No. | Name | -L-T/-L'-T' | $R^a$ |
|---|---|---|---|
| 17 | N,N'-bis{2-[9',10'-dihydro-9',10'-(1",2"-dicarbomethoxy)-etheno-anthracene-9'-yl]-ethyl}-1,7-dibromoperylene-3,4:9,10-bis(dicarboximide) PDI2A-DMDA-Br$_2$ | 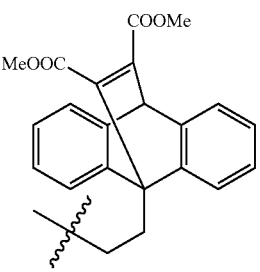 | Br |
| 18 | N,N'-bis{2-[9',10'-dihydro-9',10'-(1",2"-dicarbomethoxy)-etheno-anthracene-9'-yl]-ethyl}-1,7-dicyanoperylene-3,4:9,10-bis(dicarboximide) PDI2A-DMDA-CN$_2$ | | CN |
| 19 | N,N'-bis{3-[9',10'-dihydro-9',10'-(1",2"-dicarbomethoxy)-etheno-anthracene-9'-yl]-propyl}-1,7-dibromoperylene-3,4:9,10-bis(dicarboximide) PDI3A-DMDA-Br$_2$ | 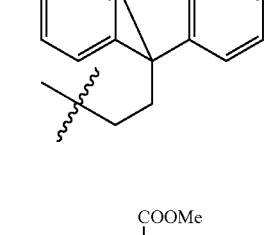 | Br |
| 20 | N,N'-bis{3-[9',10'-dihydro-9',10'-(1",2"-dicarbomethoxy)-etheno-anthracene-9'-yl]-propyl}-1,7-dicyanoperylene-3,4:9,10-bis(dicarboximide) PDI3A-DMDA-CN$_2$ | 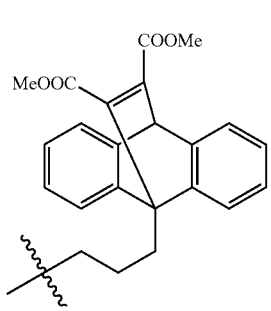 | CN |

TABLE 2-continued

| No. | Name | -L-T/-L'-T' | $R^a$ |
|---|---|---|---|
| 21 | N,N'-bis{3-[9',10'-dihydro-9',10'-(1",2"-dicarbomethoxy)-ethano-anthracene-9'-yl]-propyl}-1,7-dibromoperylene-3,4:9,10-bis(dicarboximide) PDI3A-DMF-Br$_2$ | 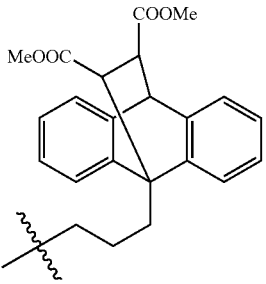 | Br |
| 22 | N,N'-bis{3-[9',10'-dihydro-9',10'-(1",2"-dicarbomethoxy)-ethano-anthracene-9'-yl]-propyl}-1,7-dicyanoperylene-3,4:9,10-bis(dicarboximide) PDI3A-DMF-CN$_2$ | 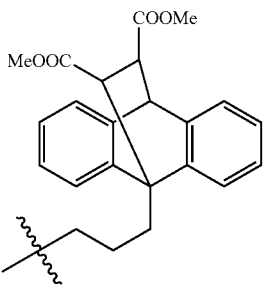 | CN |
| 23 | N,N'-bis{3-[9',10'-dihydro-9',10'-(1",2"-ditrifluoromethyl)-etheno-anthracene-9'-yl]-propyl}-1,7-dibromoperylene-3,4:9,10-bis(dicarboximide) PDI3A-DFMA-Br$_2$ | 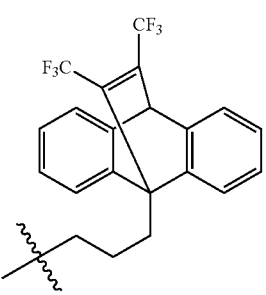 | Br |
| 24 | N,N'-bis{3-[9',10'-dihydro-9',10'-(1",2"-ditrifluoromethyl)-etheno-anthracene-9'-yl]-propyl}-1,7-dicyanoperylene-3,4:9,10-bis(dicarboximide) PDI3A-DFMA-CN$_2$ | 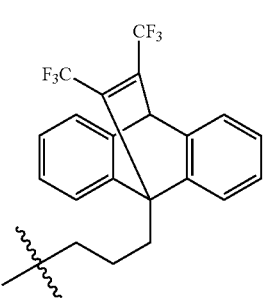 | CN |

TABLE 2-continued

| No. | Name | -L-T/-L'-T' | $R^a$ |
|-----|------|-------------|-------|
| 25 | N,N'-bis{3-[9',10'-dihydro-9',10'-(2",5"-dioxo-tetrahydrofura-3",4"-no)-anthracene-9'-yl]-propyl}-1,7-dibromoperylene-3,4:9,10-bis(dicarboximide) | | Br |
| 26 | N,N'-bis{3-[9',10'-dihydro-9',10'-(2",5"-dioxo-tetrahydrofura-3",4"-no)-anthracene-9'-yl]-propyl}-1,7-dicyanoperylene-3,4:9,10-bis(dicarboximide) | | CN |
| 27 | N,N'-bis{3-[9',10'-dihydro-9',10'-(1",3"-dioxolan-2"-one-4",5"-no)-anthracene-9'-yl]-propyl}-1,7-dibromoperylene-3,4:9,10-bis(dicarboximide) PDI3A-VC-Br$_2$ | | Br |
| 28 | N,N'-bis{3-[9',10'dihydro-9',10'-(1",3"-dioxolan-2"-one-4",5"-no)-anthracene-9'-yl]-propyl}-1,7-dicyanoperylene-3,4:9,10-bis(dicarboximide) PDI3A-VC-CN$_2$ | | CN |

TABLE 2-continued

| No. | Name | -L-T/-L'-T' | $R^a$ |
|-----|------|-------------|-------|
| 29 | N,N'-bis{3-[9',10'-dihydro-9',10'-(4''-phenyl-1'',2'',4''-triazolidine-3,5-dione -1'',2''-no)-anthracene-9'-yl]-propyl}-1,7-dibromoperylene-3,4:9,10-bis(dicarboximide) | | Br |
| 30 | N,N'-bis{3-[9',10'-dihydro-9',10'-(4''-phenyl-1'',2'',4''-triazolidine-3,5-dione-1'',2''-no)-anthracene-9'-yl]-propyl}-1,7-dicyanoperylene-3,4:9,10-bis(dicarboximide) | | CN |
| 31 | N,N'-bis[(methylurazolyl)anthracene-9'-yl-propyl]-1,7-dibromoperylene-3,4:9,10-bis(dicarboximide)<br>PDI3A-MU-Br$_2$ | | Br |

TABLE 2-continued

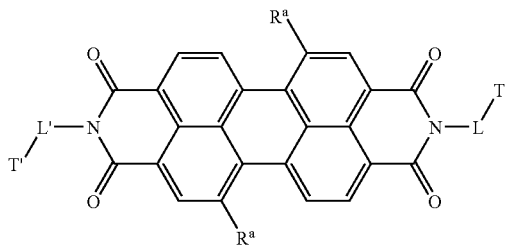

| No. | Name | -L-T/-L'-T' | $R^a$ |
|---|---|---|---|
| 32 | N,N'-bis[(methylurazolyl)anthracene-9'-yl-propyl]-1,7-dicyanoperylene-3,4:9,10-bis(dicarboximide) PDI3A-MU-CN$_2$ | | CN |

Another aspect of the present teachings relates to methods of solubilizing compounds of formula I as well as methods of converting compounds of formula II to their active semiconductor form. Accordingly, in various embodiments, compounds of formula I can be converted to their corresponding soluble precursors, for example, compounds of formula II, using Diels-Alder reactions. In various embodiments, the soluble precursors then can be converted back to the semiconductor compounds, in particular, compounds of formula I, upon treatment including application of heat and/or irradiation (e.g., light). For example, the Diels-Alder reaction of an n-[acene]-functionalized rylenes with a dienophile can be employed to synthesize the soluble precursor, which can then be converted to the active semiconductor form via a retro Diels-Alder process.

Diels-Alder reactions involving activated double and triple bond(s)-containing dienophiles have been well investigated in organic synthesis and materials chemistry (see e.g., Weinreb (1988), *Acc. Chem. Res.*, 21: 313; Boger et al. (1987), *Hetero Diels-Alder Methodology in Organic Synthesis*, Academic: San Diego; Bussas et al. (1983), *Sulfur Rep.* 2: 215; and Zhang et al. (1941), *J. Am. Chem. Soc.*, 63: 1372). Scheme 3 below illustrates an exemplary Diels-Alder reaction where a diene, for example, 2,3,4,5-tetramethylhexa-2,4-diene, is reacted with a double bond-containing or triple bond-containing dienophile.

Scheme 3

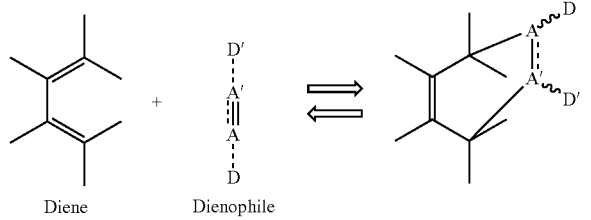

wherein A and A' independently are C, $CR^l$, N, O, P, $S(O)_m$, and Se, and A and A' optionally are independently substituted with D and D';

$R^l$ is H, oxo, a $C_{1-10}$ alkyl group, a divalent alkyl group, or an electron-withdrawing group;

D and D' independently are H, a $C_{1-10}$ alkyl group, a $C_{6-14}$ aryl group, or an electron-withdrawing group, or D and D', together with the atoms to which they are attached, form a $C_{3-14}$ cycloalkyl group or a 3-14 membered cycloheteroalkyl group, each of which optionally can be substituted with 1-4 $R^g$ groups; and $R^g$ and m are as defined herein.

Examples of dienophiles include, but are not limited to, those shown below:

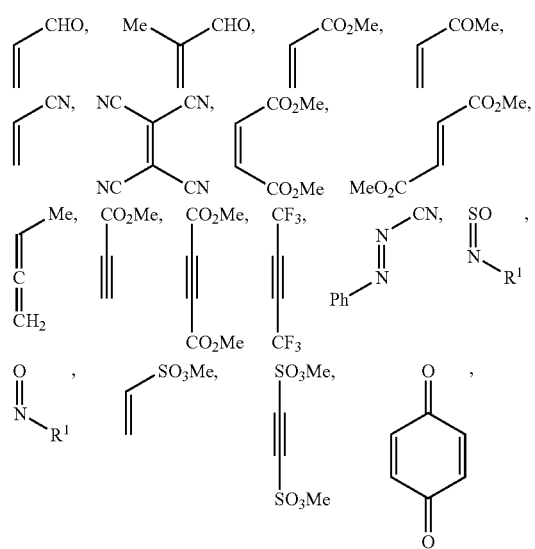

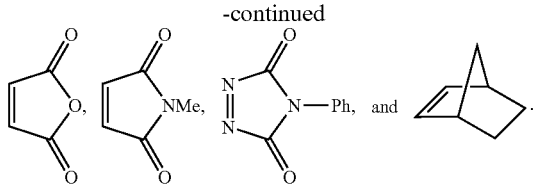

While benzene and naphthalene, as dienes, are generally quite unreactive, acenes with at least three linearly fused rings (e.g., anthracene) can give Diels-Alder reactions readily. Examples of dienes include, but are not limited to, those shown below:

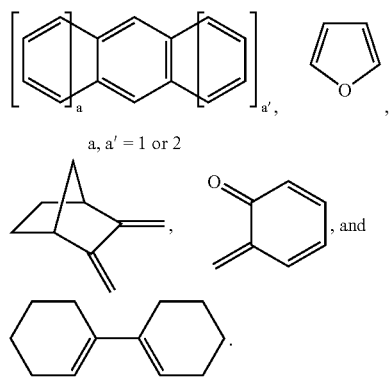

Accordingly, compounds of formula I can be converted to compounds of formula II via a Diels-Alder reaction, and compounds of formula II can be converted to compounds of formula I via a retro Diels-Alder reaction as shown in Scheme 4 below:

Scheme 4

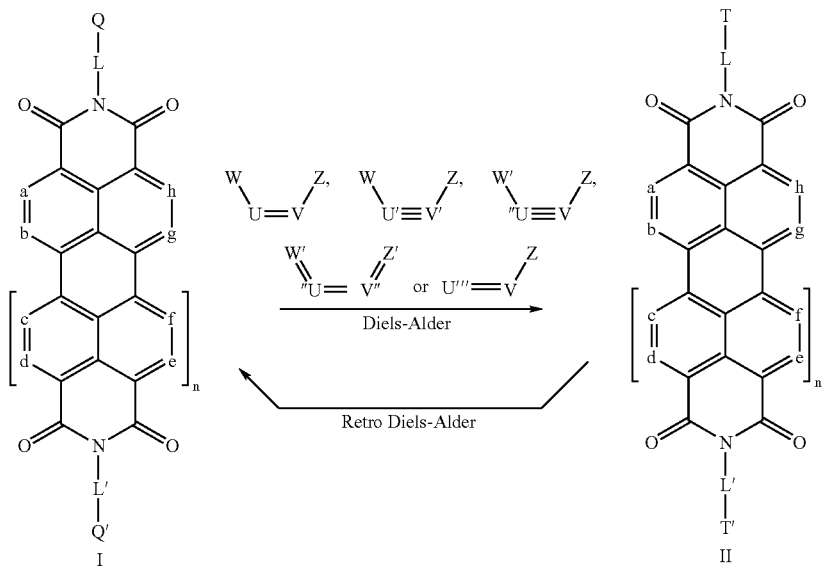

where L, L', Q, Q', T, T', U, U', U'', U''', V, V', V'', W, W', Z, Z', a, b, c, d, e, f g, h, and n are as defined herein.

Certain embodiments of the compounds disclosed herein can be soluble in common solvents. As used herein, a compound can be considered soluble in a solvent when at least 1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone, and methyl ethyl ketone; ethers such as tetrahydrofuran, dioxane, bis(2-methoxyethyl)ether, diethyl ether, di-isopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. Examples of common inorganic solvents include water and ionic liquids.

Accordingly, the present teachings further provide compositions that can include one or more compounds disclosed herein dissolved or dispersed in a liquid medium, for example, an organic solvent, an inorganic solvent, or combinations thereof (e.g., a mixture of organic solvents, inorganic solvents, or ganic and inorganic solvents). In some embodiments, the composition can further include one or more additives independently selected from detergents, dispersants, binding agents, compatibilizing agents, curing agents, initiators, humectants, antifoaming agents, wetting agents, pH modifiers, biocides, and bacteriostats. For example, surfactants and/or other polymers (e.g., polystyrene, polyethylene, poly-alpha-methylstyrene, polyisobutene, polypropylene, polymethylmethacrylate, and the like) can be included as a dispersant, a binding agent, a compatibilizing agent, and/or an antifoaming agent. In some embodiments, such compositions can include one or more compounds disclosed herein, for example, two or more different compounds of the present teachings can be dissolved in an organic solvent to prepare a composition for deposition. In certain embodiments, the composition can include two or more regioisomers, for example, compounds having moieties of formulae i and ii.

Various deposition techniques, including various solution-processing techniques, have been used in organic electronics. For example, much of the printed electronics technology has focused on inkjet printing. Inkjet printing is a noncontact process, which offers the benefits of greater control over feature position, multilayer registration, and not requiring a preformed master (compared to contact printing techniques), as well as digital control of ink ejection, thereby providing drop-on-demand printing. However, contact printing techniques have the key advantage of being well-suited for very fast roll-to-roll processing. Exemplary contact printing techniques include, but are not limited to, screen-printing, gravure printing, offset printing, flexographic printing, lithographic printing, pad printing, and microcontact printing. As used herein, "printing" includes noncontact printing process, such as inkjet printing and the like, and contact printing process, such as screen printing, gravure printing, offset printing, flexographic printing, lithographic printing, pad printing, micro-contact printing, and the like. Other solution processing techniques include, for example, spin coating, drop-casting, zone casting, dip coating, blade coating, or spraying. In addition, the deposition step can be carried out by vacuum vapor deposition.

Another aspect of the present teachings provides methods of preparing a thin film semiconductor material that can include one or more compounds of formula I. The methods can include preparing a precursor composition that can include one or more compounds of formula II in one or more organic solvents, depositing the precursor composition on a substrate to provide a thin film semiconductor precursor, and heating and/or irradiating the thin film semiconductor precursor to provide a thin film semiconductor material that includes one or more compounds of formula I. In some embodiments, the depositing step can be carried out by printing, including inkjet printing and various contact printing techniques (e.g., screen-printing, gravure printing, offset printing, pad printing, and microcontact printing). In other embodiments, the depositing step can be carried out by spin coating, drop-casting, zone coating, dip coating, blade coating, or spraying. The precursor composition can undergo a retro-Diels-Alder reaction in solid phase to give the desired n-type semiconductor material. In certain embodiments, the thin film semiconductor precursor can be converted to the thin film semiconductor material by thermal treatment only. In certain embodiments, the thin film semiconductor precursor can be converted to the thin film semiconductor material by irradiation only (e.g., exposure to one or more of infrared light, ultraviolet light, ionizing radiation). In certain embodiments, the thin film semiconductor precursor can be converted to the thin film semiconductor material by a combination of treatment techniques, for example, by two or more of heating, irradiation, and exposure to various reactive chemical reagents (gases or liquids).

As the semiconductor compounds disclosed herein can be rendered soluble (e.g., via conversion to a soluble precursor) in common solvents, the present teachings can offer processing advantages in fabricating electrical devices such as field effect transistors (e.g., thin film transistors), photovoltaics, organic light emitting diodes (OLEDs), organic analogs to, and hybrids with, complementary metal oxide semiconductors (CMOS) circuitry, complementary inverters, D flip-flops, rectifiers, and ring oscillators, that make use of the compounds disclosed herein. Such electronic devices as well as methods of making the same also are within the scope of the present teachings. Further, it should be understood that the devices described herein also can comprise two or more compounds of the present teachings, for example, two or more regioisomers as described herein. In particular embodiments, the devices can include two or more regioisomers having moieties of formulae i and ii.

In another aspect, the present teachings further provide articles of manufacture that can include composites having a semiconductor material of the present teachings and a substrate component and/or a dielectric component. The substrate component can be selected from materials including doped silicon, an indium tin oxide (ITO), ITO-coated glass, ITO-coated polyimide, or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and a self-assembled superlattice/self-assembled nanodielectric (SAS/SAND) material (e.g., described in Yoon, M-H. et al., PNAS, 102 (13): 4678-4682 (2005), the entire disclosure of which is incorporated by reference herein), as well as a hybrid organic/inorganic dielectric material (e.g., described in U.S. patent application Ser. No. 11/642,504, the entire disclosure of which is incorporated by reference herein). The self-assembled superlattice/self-assembled nanodielectric materials mentioned above can include periodically alternating layers, wherein these alternating layers can include two or more of: (i) layers including a silyl or siloxane moiety, (ii) layers including a π-polarizing moiety (e.g., a stilbazolium group), and (iii) coupling layers including a siloxane matrix. In certain embodiments, the self-assembled superlattice/self-assembled nanodielectric materials can be prepared by layer-by-layer solution phase deposition of molecular silicon precursors, for example, silicon-containing aliphatic and aromatic compounds. With regard to the hybrid organic/inorganic dielectric materials, these materials can have periodically alternating layers that include one or more inorganic layers having an inorganic moiety selected from one or more main group metals and transition metals, and two or more organic layers selected from: (i) layers including a silyl or siloxane moiety, (ii) layers including a 7-polarizing moiety (e.g., a stilbazolium group), and (iii) coupling layers including a siloxane matrix. The dielectric component also can be prepared from one of the crosslinked polymer blends described in U.S. patent application Ser. Nos. 11/315,076, 60/816,952, and 60/861,308, the entire disclosure of each of which is incorporated by reference herein. In some embodiments, the crosslinked polymer blends can include a polymeric component (e.g., a polyalkylene) and a crosslinker (e.g., a siloxane moiety). In certain embodiments, the polymeric component and the crosslinker can be the same molecule, e.g., the crosslinker can be a pendant group on the polymeric backbone.

The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene)poly(styrenesulfonate) (PEDOT:PSS), polyaniline (PANI), polypyrrole (PPy)). One or more of the composites described herein can be incorporated within various organic electronic, optical, and optoelectronic devices such as organic thin film transistors (OTFTs), specifically, organic field effect transistors (OFETs), as well as sensors, photovoltaics such as solar cells, capacitors, complementary circuits (e.g., inverter circuits), and the like.

Other articles of manufacture in which compounds of the present teachings specifically can be useful include photovoltaics or solar cells. Compounds of the present teachings can exhibit broad optical absorption and/or a very positively shifted reduction potential, making them desirable for such applications. Accordingly, the compounds described herein can be used as a n-type semiconductor in a photovoltaic design, which includes an adjacent p-type semiconducting material that forms a p-n junction. The compounds can be in the form of a thin film semiconductor, which can be a composite of the thin film semiconductor deposited on a substrate. Exploitation of compounds of the present teachings in such devices is within the knowledge of the skilled artisan.

Accordingly, another aspect of the present teachings relates to methods of fabricating an organic field effect transistor that can incorporate a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

In various embodiments, OTFT devices can be fabricated with the present compounds on doped silicon substrates, using $SiO_2$ as the dielectric, in top-contact geometries. In particular embodiments, the active semiconducting layer which incorporates at least a compound of the present teachings can be deposited by vacuum vapor deposition at room temperature or at an elevated temperature. In other embodiments, the active semiconducting layer which incorporates at least a compound of formula I can be applied by spin-coating or jet printing of a composition including at least a compound of formula II to provide a semiconductor precursor, and subjecting the semiconductor precursor to thermal treatment, irradiation, various reactive chemical reagents, or a combination thereof. For top-contact devices, metallic contacts can be patterned on top of the active semiconductor layers using shadow masks.

The following examples are provided to illustrate further and to facilitate the understanding of the present teachings and are not in any way intended to limit the invention.

Example 1

Preparation of Anthracene-Based Amines

Step a. Preparation of anthracen-9-yl-amine/9-aminoanthracene

To a solution of tin chloride (25.4 g, 134 mmol) in concentrated hydrochloric acid (HCl, 210 mL) was added dropwise a solution of 9-nitroanthracene (10.0 g, 44.8 mmol) in acetic acid (420 mL), and the mixture was heated to reflux for 1 hour. The mixture was cooled to room temperature and filtered. The residue was treated with an aqueous solution of sodium hydroxide (NaOH, 1 N, 300 mL) and extracted with dichloromethane ($CH_2Cl_2$). The organic layer was dried over magnesium sulfate ($MgSO_4$) and concentrated to give anthracen-9-yl-amine as brown crystals (6.41 g, 74% yield). $^1$H NMR ($CDCl_3$) δ 8.00-7.95 (4H, m), 7.91 (1H, s), 7.47-7.42 (4H, m), 4.89 (2H, br-s).

Step b. Preparation of anthracen-9-yl-methylamine/9-aminomethylanthracene

A solution of triphenylphosphine (16.44 g, 100.8 mmol) in acetonitrile (120 mL) was flushed with nitrogen for 20 minutes. Bromine (3.3 mL) was added and a solution of anthracen-9-yl-methanol (15.0 g, 72.0 mmol) in acetonitrile (100 mL) was added dropwise. The mixture was stirred for 2 hours at room temperature and refrigerated at 5° C. overnight. The solution was cooled to 0° C. for 30 minutes and filtered. The residue was washed with cold acetonitrile and purified by recrystallization from chloroform to give 9-bromomethyl-anthracene as yellow crystals (13.47 g, 69% yield). $^1$H NMR ($CDCl_3$) δ 8.51 (1H, s), 8.32 (2H, d), 8.05 (2H, d), 7.66 (2H, dd), 7.52 (2H, dd), 5.56 (2H, s).

A solution of 9-bromomethyl-anthracene (7.85 g, 29.0 mmol) and sodium azide (7.79 g, 120 mmol) in dimethylformamide (DMF, 190 mL) was heated at 50° C. for 30 minutes. The mixture was cooled to room temperature, and extracted with ether, and the ether layers were washed with water, dried over $MgSO_4$ and concentrated to give 9-azidomethyl-anthracene as yellow crystals (5.92 g, 87% yield). $^1$H NMR ($CDCl_3$) δ 8.53 (1H, s), 8.31 (2H, d), 8.07 (2H, d), 7.61 (2H, dd), 7.53 (2H, dd), 5.35 (2H, s).

To a solution of 9-azidomethyl-anthracene (8.47 g, 36.3 mmol) in tetrahydrofuran (THF, 60 mL) was added triphenylphosphine (10.48 g, 39.94 mmol) under a nitrogen atmosphere at 0° C. and the mixture was stirred at room temperature for 2 hours. Water (1.2 mL) was added and the resulting mixture was stirred for 12 hours. Ether (400 mL) was added and the solution cooled to 0° C. HCl (10%, 100 mL) was added slowly and the amine salt was collected by filtration and suspended in ethyl acetate (EtOAc, 600 mL). After cooling to 0° C., the solution was made basic by slow addition of concentrated ammonium hydroxide ($NH_4OH$) and the layers were separated. The aqueous layer was extracted with EtOAc and the combined organic layers were washed with water, dried over $MgSO_4$ and concentrated to give the product as yellow crystals (6.64 g, 88% yield). $^1$H NMR ($CDCl_3$) δ 8.41 (1H, s), 8.36 (2H, d), 8.04 (2H, d), 7.56 (2H, dd), 7.49 (2H, dd), 4.84 (2H, s), 1.64 (1H, br-s).

Step c. Preparation of 2-anthracen-9-yl-ethylamine/
9-(2-aminoethyl)anthracene

A solution of 9-chloromethyl-anthracene (10.0 g, 44.11 mmol) and potassium cyanide (28.72 g, 441.1 mmol) in acetonitrile (1.6 L) was heated to reflux for 2 hours. The mixture was cooled to room temperature, filtered and concentrated. The residue was dissolved in $CH_2Cl_2$, washed with water, dried over $MgSO_4$ and concentrated to give anthracen-9-yl-acetonitrile as yellow crystals (9.40 g, 98% yield). $^1$H NMR ($CDCl_3$) δ 8.53 (1H, s), 8.18 (2H, d), 8.07 (2H, d), 7.65 (2H, dd), 7.54 (2H, dd), 4.60 (2H, s).

To a solution of anthracen-9-yl-acetonitrile (3.0 g, 13.82 mmol) in ethanol (150 mL) was added concentrated $NH_4OH$ (15 mL) and Raney nickel (15 g), and ammonia gas was bubbled through the mixture at 0° C. for 10 minutes. The suspension was hydrogenated for 48 hours at room temperature. Air was bubbled through the solution and Raney nickel was removed by filtration. The filtrate was concentrated and the oily residue was dissolved in $CH_2Cl_2$, washed with an aqueous solution of sodium carbonate ($Na_2CO_3$, 10%), dried over $MgSO_4$ and concentrated. The resulting solid was purified by recrystallization from a mixture of hexane and $CH_2Cl_2$ (7:3) to give 2-anthracen-9-yl-ethylamine as yellow crystals (2.60 g, 85%). $^1$H NMR ($CDCl_3$) δ 8.37 (1H, s), 8.33 (2H, d), 8.02 (2H, d), 7.54-7.47 (4H, m), 3.86 (2H, t), 3.19 (2H, t), 1.34 (2H, br-s).

Step d. Preparation of 3-anthracen-9-yl-propylamine/
9-(3-aminopropyl)anthracene To a solution of anthracen-9-yl-methanol (6.58 g, 31.6 mmol) and (cyanomethyl)trimethylphosphonium iodide (19.19 g, 78.96 mmol) in propionitrile (77 mL) was added diisopropylethylamine (DIPEA, 49.4 mL, 94.74 mmol) and the mixture was stirred at 97° C. for 20 hours. Water (3.82 mL) was added, nitrogen was bubbled though the mixture, and the mixture was stirred for 20 hours. Water (480 mL) and concentrated HCl (19 mL) were added and the mixture was extracted with EtOAc. The organic layer was washed with brine, dried over $MgSO_4$ and concentrated. The resulting solid was purified by silica gel column chromatography (hexane:$CHCl_3$=1:1) to give 3-anthracen-9-yl-propionitrile as brown crystals (6.93 g, 95% yield). $^1$H NMR ($CDCl_3$) δ 8.43 (1H, s), 8.19 (2H, d), 8.05 (2H, d), 7.60 (2H, dd), 7.51 (2H, dd), 4.02 (2H, t), 2.79 (2H, t).

To a solution of 3-anthracen-9-yl-propionitrile (3.0 g, 13 mmol) in EtOH (140 mL) was added concentrated $NH_4OH$ (14 mL) and Raney nickel (14 g), and ammonia gas was bubbled through the mixture at 0° C. for 10 minutes. The suspension was hydrogenated at room temperature for 24 hours. Air was bubbled through the solution and Raney nickel was removed by filtration. The filtrate was concentrated, and the oily residue was dissolved in $CH_2Cl_2$, washed with an aqueous solution of $Na_2CO_3$ (10%), dried over $MgSO_4$ and concentrated to give 3-anthracen-9-yl-propylamine as a brown oil (2.60 g, 85% yield). $^1$H NMR ($CDCl_3$) δ 8.35 (1H, s), 8.30 (2H, d), 8.02 (2H, d), 7.54-7.46 (4H, m), 3.68 (2H, t), 2.95 (2H, t), 2.01-1.95 (2H, m) 1.32 (2H, br-s).

Example 2

Preparation of N,N'-bis(9-anthracenyl)-1,7-dibromoperylene-3,4:9,10-bis(dicarboximide) 1 (PDI0A-$Br_2$)

A mixture of 9-aminoanthracene (4.20 g, 21.8 mmol, Example 1a) and 1,7-dibromoperylene-3,4:9,10-dianhydride (3.00 g, 5.45 mmol) in propionic acid (60 mL) was heated to reflux for 6 hours. After the mixture was cooled to room temperature, the resulting solid was collected by filtration, washed with propionic acid and methanol (MeOH), and dried overnight. The crude product (4.40 g) was purified by silica gel column chromatography ($CH_2Cl_2$) to afford N,N'-bis(9-anthracenyl)-1,7-dibromoperylene-3,4:9,10-bis(dicarboximide) as a red solid (0.66 g, 0.73 mmol, 13.4% yield). M.p.>250° C. (DMF); $^1$H NMR ($CDCl_3$, 500 MHz): δ 9.70 (m, 2H), 9.09 (s, 2H), 8.91 (m, 2H), 8.73 (s, 2H), 8.10 (m, 4H), 7.82 (m, 4H), 6.60-7.40 (t, 8H); MS-MALDI (Calcd: 900.01): 898.0.

Example 3

Preparation of N,N'-bis(9-anthracenyl)-1,7-dicyanoperylene-3,4:9,10-bis(dicarboximide) 2 (PDI0A-$CN_2$)

A mixture of N,N'-bis{9-anthracenyl}-1,7-dibromoperylene-3,4:9,10-bis(dicarboximide) (0.50 g, 0.55 mmol, Example 2) and copper cyanide (CuCN, 0.90 g, 10 mmol) in DMF (35 mL) was deaerated and placed under nitrogen. The reaction mixture was heated at 150° C. for 7 hours. After the mixture was cooled to room temperature, the precipitate was collected by filtration, washed several times with MeOH, and dried overnight. The crude solid (0.34 g) was recrystallized from DMF-xylene to afford N,N'-bis(9-anthracenyl)-1,7-dicyanoperylene-3,4:9,10-bis(dicarboximide) as a red powder (0.17 g, 0.21 mmol, 38.2% yield). M.p.>250° C. (DMF); $^1$H NMR ($CDCl_3$, 300 MHz): δ 10.02-9.85 (m, 2H), 9.10-8.95 (m, 4H), 8.78-8.70 (m, 2H), 8.20 (m, 4H), 7.90-7.70 (m, 4H), 2.60-7.45 (t, 8H); MS-MALDI (Calcd: 792.3): 791.5.

Example 4

Preparation of N,N'-bis(anthracen-9-ylmethyl)-1,7-dibromoperylene-3,4:9,10-bis(dicarboximide) 3 (PDI1A-$Br_2$)

A mixture of 9-aminomethylanthracene (1.00 g, 4.82 mmol, Example 1b) and 1,7-dibromoperylene-3,4:9,10-dianhydride (1.00 g, 1.82 mmol) in xylene (13.4 mL) and propionic acid (42.13 mmol, 3.05 mL) was heated to reflux for 30 minutes. After the mixture was cooled to room temperature, MeOH (20 mL) was added and the precipitate was collected by filtration, washed with MeOH, and dried overnight. The crude product (1.45 g) was further washed with boiling dimethyl sulfoxide (DMSO, 53 mL) to afford N,N'-bis(anthracen-9-ylmethyl)-1,7-dibromoperylene-3,4:9,10-bis(dicarboximide) as a red solid (0.93 g, 1.00 mmol, 55.0% yield). M.p.>250° C. (DMF); $^1$H NMR ($C_2D_2Cl_4$, 500 MHz): δ 9.66 (d, 2H, J=8.8 Hz), 9.07 (s, 2H), 8.87 (m, 2H, J=8.8 Hz), 8.66 (m, 4H), 8.60 (s, 2H), 8.15 (m, 4H), 7.70 (m, 4H), 7.60 (m, 4H), 6.49 (s, 4H); MS-MALDI (Calcd. 928.6): 930.5.

Example 5

Preparation of N,N'-bis(anthracen-9-ylmethyl)-1,7-dicyanoperylene-3,4:9,10-bis(dicarboximide) 4 (PDI1A-$CN_2$)

A mixture of N,N'-bis(anthracen-9-ylmethyl)-1,7-dibromoperylene-3,4:9,10-bis(dicarboximide) (0.28 g, 0.30 mmol, Example 4) and CuCN (0.48 g, 5.36 mmol) in DMF (12 mL) was deaerated and placed under nitrogen. The reaction mixture was heated at 150° C. for 7 hours. After cooling to room temperature, the precipitate was collected by filtration, washed with MeOH, and dried overnight. The crude solid (0.22 g) was recrystallized from DMF-xylene to afford N,N'-bis(9-anthracenyl)-1,7-dicyanoperylene-3,4:9,10-bis(dicarboximide) as a red powder (0.17 g, 0.21 mmol, 38.2% yield). M.p.>250° C. (DMF); $^1$H NMR ($CDCl_3$, 300 MHz) δ 10.02-9.85 (m, 2H), 9.10-8.95 (m, 4H), 8.78-8.70 (m, 2H), 8.20 (m, 4H), 7.90-7.70 (m, 4H), 2.60-7.45 (t, 8H); MS-MALDI: 820.0.

Example 6

Preparation of N,N'-bis[2-(anthracen-9-yl)ethyl]-1,7-dibromoperylene-3,4:9,10-bis(dicarboximide) 5 (PDI2A-$Br_2$)

A mixture of 9-(2-aminoethyl)anthracene (1.80 g, 8.13 mmol, Example 1c) and 1,7-dibromoperylene-3,4:9,10-dianhydride (2.00 g, 3.64 mmol) in xylene (26.8 mL) and propionic acid (82.34 mmol, 6.10 mL) was heated to reflux for 30 minutes. After the mixture was cooled to room temperature, MeOH (60 mL) was added and the precipitate was collected by filtration, washed with MeOH, and dried overnight. The crude product (2.75 g) was further washed with boiling DMSO (99 mL) to afford N,N'-bis[2-(anthracen-9-yl)ethyl]-1,7-dibromoperylene-3,4:9,10-bis(dicarboximide) as a red solid (2.20 g, 2.30 mmol, 63.2% yield). M.p.>250° C. (DMF); $^1$H NMR ($C_2D_2Cl_4$, 500 MHz): δ 9.66 (m, 2H), 9.12 (s, 2H), 8.86 (d, 2H, J=8.6 Hz), 8.82 (d, 2H, J=8.4 Hz), 8.56

(s, 2H), 7.17 (d, 4H, J=8.4 Hz), 7.71 (m, 4H), 7.66 (m, 4H), 4.69 (m, 4H), 4.13 (m, 4H); MS-MALDI (Calcd 956.7): 956.4.

FIG. 1, in part, shows an optical absorption spectrum of PDI2A-Br$_2$ in THF.

Example 7

Preparation of N,N'-bis[2-(anthracen-9-yl)ethyl]-1,7-dicyanoperylene-3,4:9,10-bis(dicarboximide) 6 (PDI2A-CN$_2$)

A mixture of N,N'-bis[2-(anthracen-9-yl)ethyl]-1,7-dibromoperylene-3,4:9,10-bis(dicarboximide) (0.57 g, 0.60 mmol, Example 6) and CuCN (0.97 g, 10.8 mmol) in DMF (25 mL) was deaerated and placed under nitrogen. The reaction mixture was heated at 150° C. for 7 hours. After cooling to room temperature, the precipitate was collected by filtration, washed with MeOH, and dried overnight. The crude solid (0.70 g) was recrystallized from DMF-xylene to afford N,N'-bis(9-anthracenyl)-1,7-dicyanoperylene-3,4:9,10-bis(dicarboximide) as a red powder (0.17 g, 0.21 mmol, 38.2% yield). M.p.>250° C. (DMF); $^1$H NMR (CDCl$_3$, 300 MHz) δ 10.02-9.85 (m, 2H), 9.10-8.95 (m, 4H), 8.78-8.70 (m, 2H), 8.20 (m, 4H), 7.90-7.70 (m, 4H), 2.60-7.45 (t, 8H); MS-MALDI: 848.3.

Example 8

Preparation of N,N'-bis[3-(anthracen-9-yl)propyl]-1,7-dibromoperylene-3,4:9,10-bis(dicarboximide) 7 (PDI3A-Br$_2$)

A mixture of 9-(3-aminopropyl)anthracene (3.12 g, 13.3 mmol) and 1,7-dibromoperylene-3,4:9,10-dianhydride (2.43 g, 4.41 mmol) in xylene (32.6 mL) and propionic acid (100.0 mmol, 7.4 mL) was heated to reflux for 30 minutes. After the mixture was cooled to room temperature, MeOH (80 mL) was added and the precipitate was collected by filtration, washed with MeOH, and dried overnight. The crude product (3.70 g) was further washed with boiling DMSO (152 mL) to afford N,N'-bis[3-(anthracen-9-yl)propyl]-1,7-dibromoperylene-3,4:9,10-bis(dicarboximide) as a red solid (2.72 g, 2.76 mmol, 62.3% yield). M.p.>250° C. (DMF); $^1$H NMR (C$_2$D$_2$Cl$_4$, 500 MHz): δ 9.56 (d, 2H, J=8.7 Hz), 8.98 (s, 2H), 8.77 (d, 2H, J=8.7 Hz), 8.43 (s, 2H), 8.41 (d, 2H, J=8.5 Hz), 7.10 (d, 4H, J=8.6 Hz), 7.66 (t, 4H, J=8.5 Hz), 7.58 (t, 4H, J=8.5 Hz), 4.92 (m, 4H), 3.67 (m, 4H), 2.38 (m, 4H); MS-MALDI (Calcd 984.1): 985.2.

Figure 2:
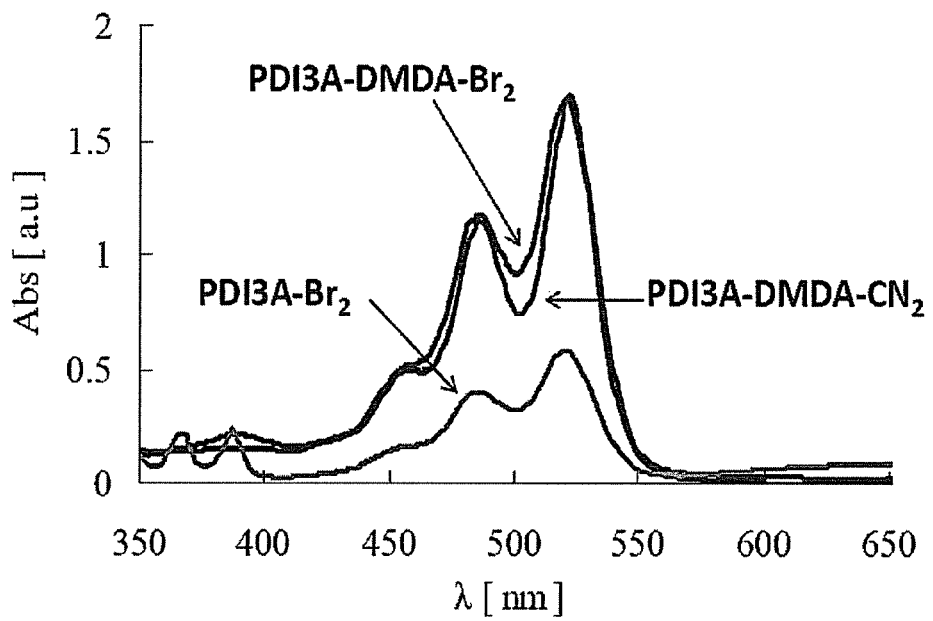
FIG. 2 provides optical absorption spectra of certain embodiments (PDI3A-$Br_2$, PDI3A-DMDA-$Br_2$ and PDI3A-DMDA-$CN_2$, all in THF) of the present teachings.

FIG. 2, in part, shows an optical absorption spectrum of PDI3A-Br$_2$ in THF.

Example 9

Preparation of N,N'-bis[3-(anthracen-9-yl)propyl]-1,7-dicyanoperylene-3,4:9,10-bis(dicarboximide) 8 (PDI3A-CN$_2$)

A mixture of N,N'-bis[3-(anthracen-9-yl)propyl]-1,7-dibromoperylene-3,4:9,10-bis(dicarboximide) (0.59 g, 0.60 mmol, Example 9) and CuCN (0.97 g, 10.8 mmol) in DMF (25 mL) was deaerated and placed under nitrogen. The reaction mixture was heated at 150° C. for 12 hours. After the mixture was cooled to room temperature, the precipitate was collected by filtration, washed with MeOH, and dried overnight. The crude solid (0.58 g) was recrystallized from DMF-xylene to afford N,N'-bis(9-anthracenyl)-1,7-dicyanoperylene-3,4:9,10-bis(dicarboximide) as a red powder (0.17 g, 0.21 mmol, 38.2% yield). M.p.>250° C. (DMF); $^1$H NMR (CDCl$_3$, 300 MHz): δ 10.02-9.85 (m, 2H), 9.10-8.95 (m, 4H), 8.78-8.70 (m, 2H), 8.20 (m, 4H), 7.90-7.70 (m, 4H), 2.60-7.45 (t, 8H); MS-MALDI: 876.5.

Example 10

Preparation of N,N'-bis{2-[9',10'-dihydro-9',10'-(1",2"-dicarbomethoxy)-etheno-anthracene-9'-yl]-ethyl}-1,7-dibromoperylene-3,4:9,10-bis(dicarboximide) 17 (PDI2A-DMDA-Br$_2$)

To a solution of N,N'-bis(2-(anthracen-9-yl)-ethyl)-1,7-dibromoperylene-3,4:9,10-bis(dicarboximide) (0.50 g, 0.52 mmol, Example 6) in o-xylene (20 mL), dimethylacetylene-dicarboxylate (3.71 g, 26.1 mmol) was added at room temperature, and the mixture was stirred at 140° C. for 48 hours. The solution was cooled to room temperature and poured into MeOH (200 mL). The resulting solid was filtered, washed with MeOH, and dried in a vacuum oven to give N,N'-bis{2-[9',10'-dihydro-9',10'-(1",2"-dicarbomethoxy)-etheno-anthracene-9'-yl]-ethyl}-1,7-dibromoperylene-3,4:9,10-bis(dicarboximide) as red crystals (0.52 g, 80% yield). $^1$H NMR (CDCl$_3$) δ 9.61-9.57 (2H, m), 9.09 and 8.99 (2H, s), 8.86-8.84, and 8.77-8.74 (2H, m), 8.00 (4H, br-s), 7.44 (4H, d, J=7.0 Hz), 7.18 (4H, dd, J=7.0 and 5.0 Hz), 7.08 (4H, dd, J=7.5 Hz), 5.66 (2H, s) 4.90-4.85 (4H, m), 4.01 and 4.00 (6H, s), 3.79 (6H, s), 3.19-3.14 (4H, m); MS-MALDI (calcd. 1238.13): 1237.09.

Figure 3:
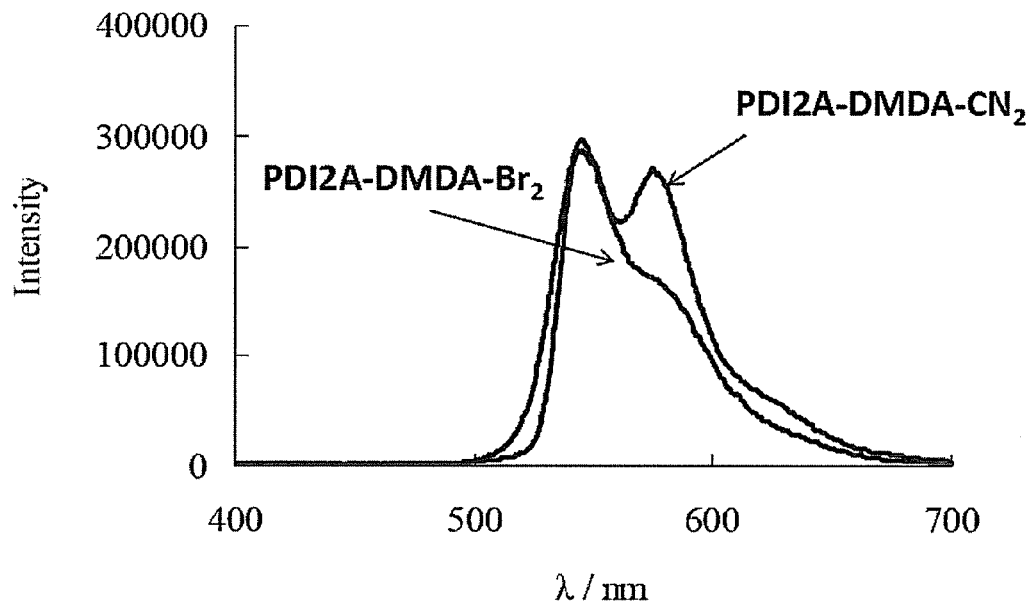
FIG. 3 provides optical emission spectra of certain embodiments (PDI2A-DMDA-$Br_2$ and PDI2A-DMDA-$CN_2$, both in THF) of the present teachings.

FIG. 1, in part, shows an optical absorption spectrum of PDI2A-DMDA-Br$_2$ in THF. FIG. 3, in part, shows an optical emission spectrum of PDI2A-DMDA-Br$_2$ in THF. FIG. 5(a) shows a cyclic voltammogram of PDI2A-DMDA-Br$_2$ (conditions: 0.1 M (n-Bu)$_4$NPF$_6$ in THF; working electrode, carbon disk (1 mm diameter); counter electrode, Pt wire; and reference electrode, Ag).

Example 11

Preparation of N,N'-bis{2-[9',10'-dihydro-9',10'-(1",2"-dicarbomethoxy)-etheno-anthracene-9'-yl]-ethyl}-1,7-dicyanoperylene-3,4:9,10-bis(dicarboximide) 18 (PDI2A-DMDA-CN$_2$)

To a solution of N,N'-bis{2-[9',10'-dihydro-9',10'-(1",2"-dicarbomethoxy)-etheno-anthracene-9'-yl]-ethyl}-1,7-dibromoperylene-3,4:9,10-bis(dicarboximide) (0.30 g, 0.24 mmol, Example 10) in DMF (20 mL), CuCN (0.39 g, 4.36 mmol) was added at room temperature, and the mixture was stirred at 160° C. for 12 hours. The solution was cooled to room temperature and poured into MeOH (300 mL). The resulting solid was filtered, washed with MeOH/H$_2$O, and dried in a vacuum oven to give a mixture of N,N'-bis{2-[9',10'-dihydro-9',10'-(1",2"-dicarbomethoxy)-etheno-anthracene-9'-yl]-ethyl}-1,7-dicyanoperylene-3,4:9,10-bis(dicarboximide) and N,N'-bis{2-[9',10'-dihydro-9',10'-(1",2"-dicarbomethoxy)-etheno-anthracene-9'-yl]-ethyl}-1,6-dicyanoperylene-3,4:9,10-bis(dicarboximide) as purple crystals (0.22 g, 92% yield). The product was further purified by precipitation from CHCl$_3$, H$_2$O, and MeOH. $^1$H NMR (CDCl$_3$) δ 9.78 (2H, d, J=8.0 Hz), 9.15 and 9.11 (2H, s), 9.02 and 8.97 (2H, d, J=7.5 and 8.0 Hz), 7.95 (4H, br-s), 7.43 (4H, d, J=7.0 Hz), 7.18 (4H), 7.08 (4H, dd, J=7.0 and 6.5 Hz), 5.66 (2H, s), 4.86 (4H), 4.02 (6H, s), 3.80 (6H, s), 3.18 (4H); MS-MALDI (calcd. 1132.30): 1132.28.

Figure 5:
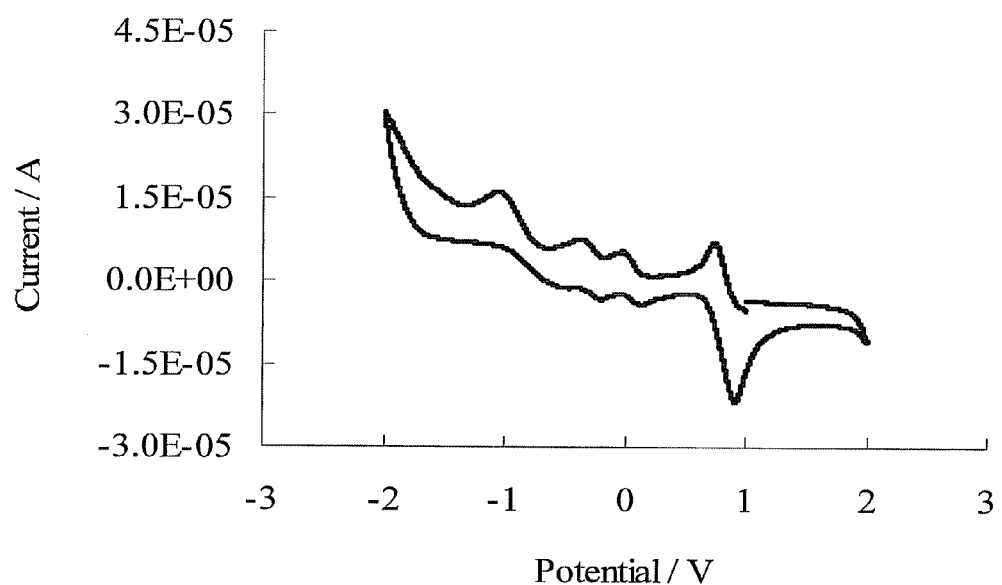
FIGS. 5(a) and 5(b) provide cyclic voltammograms of certain embodiments (PDI2A-DMDA-Br$_2$ (a) and PDI2A-DMDA-CN$_2$ (b)) of the present teachings using the following conditions: 0.1 M (n-Bu)$_4$NPF$_6$ in THF, carbon disk (1 mm diameter) working electrode, Pt wire counter electrode, and silver reference electrode.
Figure 5:
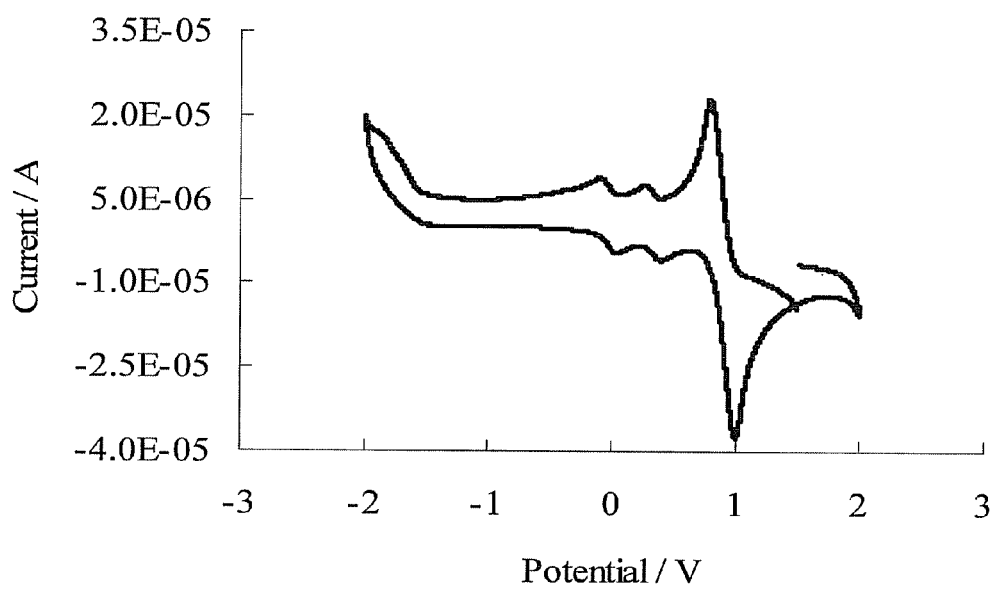

FIG. 1, in part, shows an optical absorption spectrum of PDI2A-DMDA-CN$_2$ in THF. FIG. 3, in part, shows an optical emission spectrum of PDI2A-DMDA-CN$_2$ in THF. FIG. 5(*b*) shows a cyclic voltammogram of PDI2A-DMDA-CN$_2$ (conditions: 0.1 M (n-Bu)$_4$NPF$_6$ in THF; working electrode, carbon disk (1 mm diameter); counter electrode, Pt wire; and reference electrode, Ag).

Example 12

Preparation of N,N'-bis{3-[9',10'-dihydro-9',10'-(1",2"-dicarbomethoxy)-etheno-anthracene-9'-yl]-propyl}-1,7-dibromoperylene-3,4:9,10-bis(dicarboximide) 19 (PDI3A-DMDA-Br$_2$)

To a solution of N,N'-bis(3-(anthracen-9-yl)-propyl)-1,7-dibromoperylene-3,4:9,10-bis(dicarboximide) (0.50 g, 0.52 mmol, Example 8) in o-xylene (20 mL), dimethylacetylenedicarboxylate (3.66 g, 25.7 mmol) was added at room temperature, and the mixture was stirred for at 140° C. for 48 hours. The solution was cooled to room temperature and poured into MeOH (200 mL). The resulting solid was filtered, washed with MeOH, and dried in vacuum oven to give N,N'-bis{3-[9',10'-dihydro-9',10'-(1",2"-dicarbomethoxy)-etheno-anthracene-9'-yl]-propyl}-1,7-dibromoperylene-3,4:9,10-bis(dicarboximide) as red crystals (0.65 g, 99% yield). $^1$H NMR (CDCl$_3$) δ9.51 (2H, d, J=8.5 Hz), 8.97 (2H, s) 8.75 (2H, d, J=8.0 Hz), 7.47 (4H, d, J=7.5 Hz), 7.37 (4H, d, J=7.0 Hz), 7.09 (4H, dd, J=7.0 Hz), 7.02 (4H, dd, J=7.0 Hz), 5.57 (2H, s), 4.53 (4H, t, J=7.5 Hz), 3.86 (6H, s), 3.75 (6H, s), 2.95 (4H, t, J=6.5, 9.0 Hz), 2.31 (4H, m); MS-MALDI (calcd. 1266.16): 1267.26.

Figure 4:
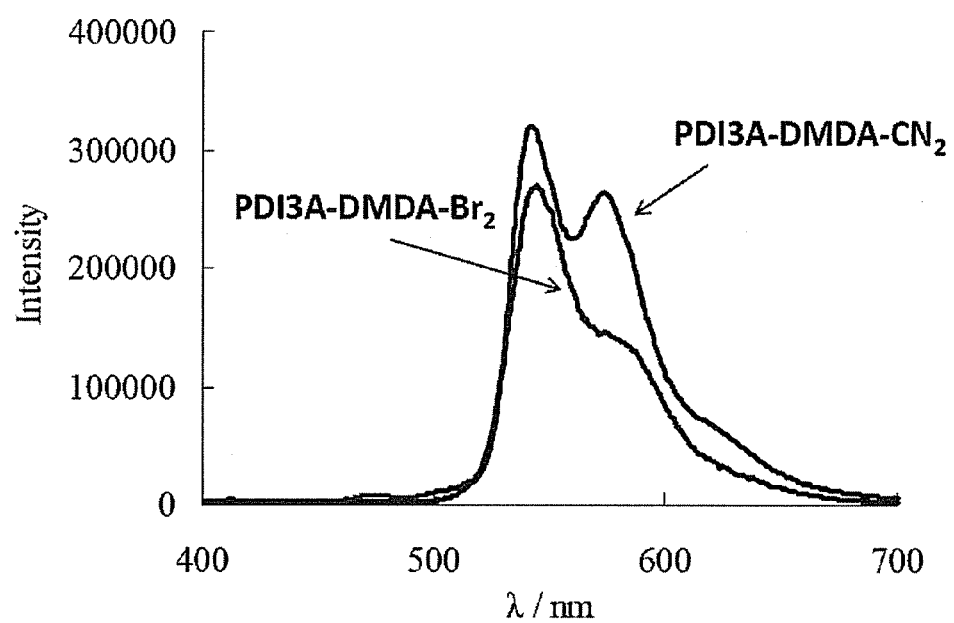
FIG. 4 provides optical emission spectra of certain embodiments (PDI3A-DMDA-Br$_2$ and PDI3A-DMDA-CN$_2$, both in THF) of the present teachings.
Figure 6:
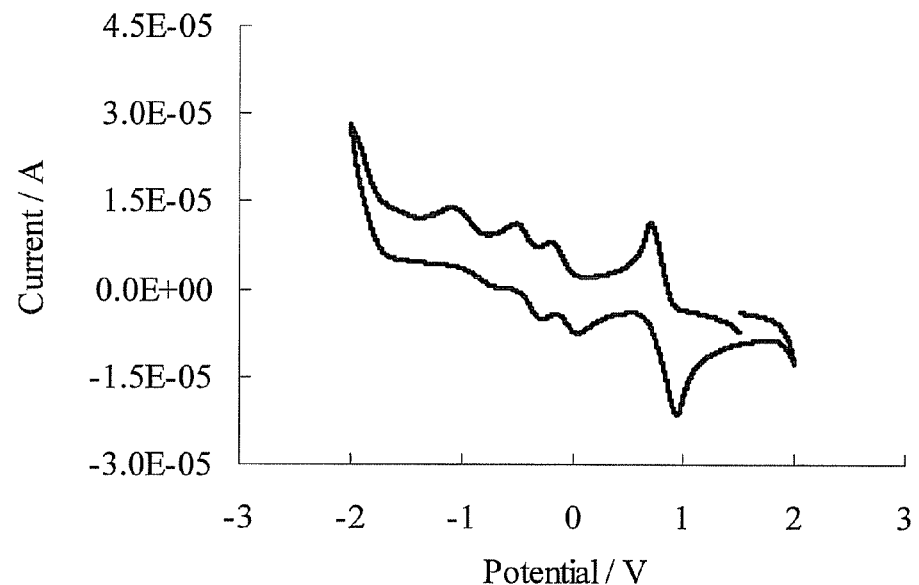
FIGS. 6(a) and 6(b) provide cyclic voltammograms of certain embodiments (PDI3A-DMDA-Br$_2$ (a) and PDI3A-DMDA-CN$_2$ (b)) of the present teachings using the following conditions: 0.1 M (n-Bu)$_4$NPF$_6$ in THF, carbon disk (1 mm diameter) working electrode, Pt wire counter electrode, and silver reference electrode.
Figure 6:
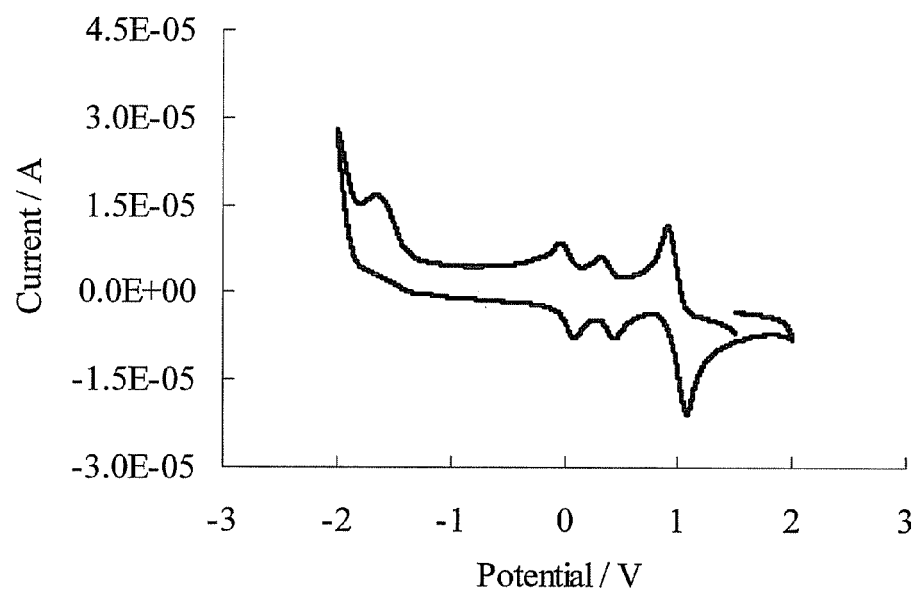

FIG. 2, in part, shows an optical absorption spectrum of PDI3A-DMDA-Br$_2$ in THF. FIG. 4, in part, shows an optical emission spectrum of PDI3A-DMDA-Br$_2$ in THF. FIG. 6(*a*) shows a cyclic voltammogram of PDI3A-DMDA-Br$_2$ (conditions: 0.1 M (n-Bu)$_4$NPF$_6$ in THF; working electrode, carbon disk (1 mm diameter); counter electrode, Pt wire; and reference electrode, Ag).

Example 13

Preparation of N,N'-bis{3-[9',10'-dihydro-9',10'-(1",2"-dicarbomethoxy)-etheno-anthracene-9'-yl]-propyl}-1,7-dicyanoperylene-3,4:9,10-bis(dicarboximide) 20 (PDI3A-DMDA-CN$_2$)

To a solution of N,N'-bis{3-[9',10'-dihydro-9',10'-(1",2"-dicarbomethoxy)-etheno-anthracene-9'-yl]-propyl}-1,7-dibromoperylene-3,4:9,10-bis(dicarboximide) (0.30 g, 0.23 mmol, Example 12) in DMF (60 mL), CuCN (0.38 g, 4.26 mmol) was added at room temperature, and the mixture was stirred at 160° C. for 12 hours. The solution was cooled to room temperature and poured into MeOH (300 mL). The resulting solid was filtered, washed with MeOH/H$_2$O, and dried in a vacuum oven to give a mixture of N,N'-bis{3-[9',10'-dihydro-9',10'-(1",2"-dicarbomethoxy)-etheno-anthracene-9'-yl]-propyl}-1,7-dicyanoperylene-3,4:9,10-bis(dicarboximide) and N,N'-bis{3-[9',10'-dihydro-9',10'-(1",2"-dicarbomethoxy)-etheno-anthracene-9'-yl]-propyl}-1,6-dicyanoperylene-3,4:9,10-bis(dicarboximide) as purple crystals (0.25 g, 91% yield). The product was further purified by reprecipitation from CHCl$_3$, H$_2$O, and MeOH. $^1$H NMR (CDCl$_3$) δ9.73 (2H, d, J=8.5 Hz), 9.08 and 9.03 (2H, s), 8.98 and 8.95 (2H, d, J=8.5 and 8.0 Hz), 7.45 (4H, d, J=7.5 Hz), 7.37 (4H, d, J=7.0 Hz), 7.09 (4H, dd, J=7.5 and 7.0 Hz), 7.02 (4H, dd, J=7.5 Hz), 5.57 (2H, s), 4.54 (4H, t, J=7.0, 7.5 Hz), 3.86 (6H, s), 3.75 (6H, s), 2.95 (4H, t, J=7.0, 8.5 Hz), 2.31 (4H, m); MS-MALDI (calcd. 1160.33): 1159.94.

Figure 7:
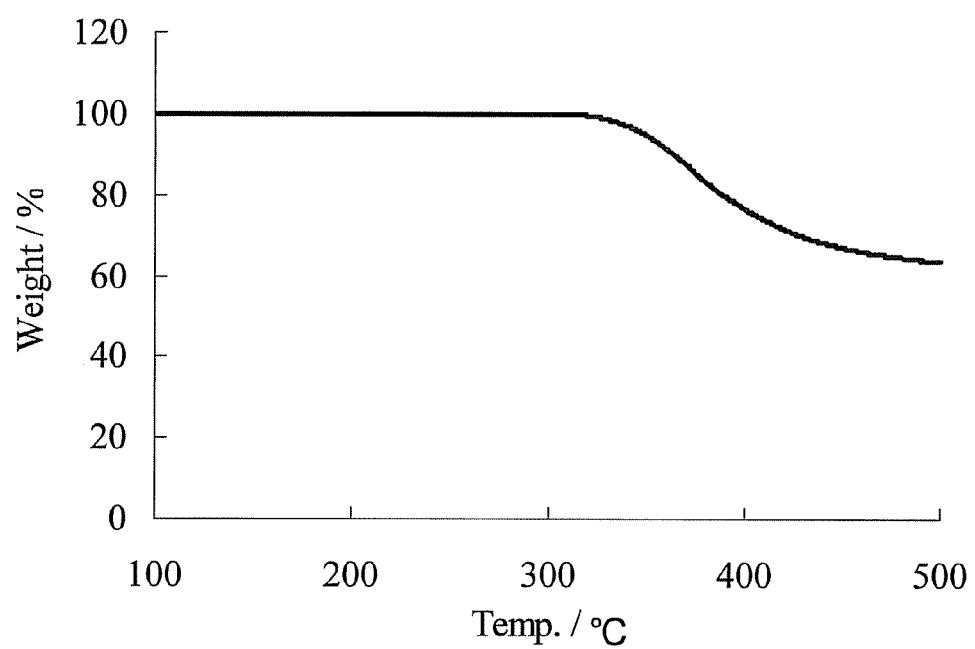
FIG. 7 provides a thermogravimetric analysis plot of a certain embodiment (PDI3A-DMDA-CN$_2$) of the present teachings with the analysis conducted at a heating rate of 2.5° C./min under nitrogen atmosphere.

FIG. 2, in part, shows an optical absorption spectrum of PDI3A-DMDA-CN$_2$ in THF. FIG. 4, in part, shows an optical emission spectrum of PDI3A-DMDA-CN$_2$ in THF. FIG. 6(*b*) shows a cyclic voltammogram of PDI3A-DMDA-CN$_2$ (conditions: 0.1 M (n-Bu)$_4$NPF$_6$ in THF; working electrode, carbon disk (1 mm diameter); counter electrode, Pt wire; and reference electrode, Ag). FIG. 7 shows a thermogravimetric analysis plot of PDI3A-DMDA-CN$_2$ (heating rate: 2.5° C./min under N$_2$).

Example 14

Preparation of N,N'-bis{3-[9',10'-dihydro-9',10'-(1",2"-dicarbomethoxy)-ethano-anthracene-9'-yl]-propyl}-1,7-dibromoperylene-3,4:9,10-bis(dicarboximide) 21 (PDI3A-DMF—Br$_2$)

To a solution of N,N'-bis(3-(anthracen-9-yl)-propyl)-1,7-dibromoperylene-3,4:9,10-bis(dicarboximide) (1.00 g, 1.02 mmol, Example 8) in o-xylene (40 mL), dimethylmaleate (7.35 g, 51.0 mmol) was added at room temperature, and the mixture was heated to reflux for 3 days. The solution was cooled to room temperature and filtered. The filtrate was poured into MeOH (600 mL), the resulting solid was filtered, washed with MeOH, and dried in a vacuum oven to give N,N'-bis{3-[9',10'-dihydro-9',10'-(1",2"-dicarbomethoxy)-ethano-anthracene-9'-yl]-propyl}-1,7-dibromoperylene-3,4:9,10-bis(dicarboximide) as red crystals (0.46 g, 35% yield). $^1$H NMR (CDCl$_3$, 500 MHz) δ 9.50 (2H, d, J=8.0 Hz), 8.97 (2H, s), 8.75 (2H, d, J=8.5 Hz), 7.47-7.43 (4H, m), 7.30-7.10 (12H, m), 4.62 (2H, s), 4.54-4.50 (4H, m), 3.51 (12H, s), 3.34 (2H, d, J=11.5 Hz), 3.20 (2H, d, J=11.0 Hz), 2.67-2.57 (4H, m), 2.42-2.40 (4H, m); MS-MALDI (calcd. 1270.19): 1271.22.

Example 15

Preparation of N,N'-bis{3-[9',10'-dihydro-9',10'-(1",2"-dicarbomethoxy)-ethano-anthracene-9'-yl]-propyl}-1,7-dicyanoperylene-3,4:9,10-bis(dicarboximide) 22 (PDI3A-DMF-CN$_2$)

To a solution of N,N'-bis{3-[9',10'-dihydro-9',10'-(1",2"-dicarbomethoxy)-ethano-anthracene-9'-yl]-propyl}-1,7-dibromoperylene-3,4:9,10-bis(dicarboximide) (0.226 g, 0.178 mmol, Example 14) in dry-DMF (45 mL), CuCN (0.286 g, 3.20 mmol) was added at room temperature, and the mixture was heated to reflux for 12 hours. The solution was cooled to room temperature and poured into MeOH (300 mL). The resulting solid was filtered, washed with MeOH and dried in a vacuum oven. The product was purified by precipitation from hot CHCl$_3$, H$_2$O, and MeOH to give a mixture of N,N'-bis{3-[9',10'-dihydro-9',10'-(1",2"-dicarbomethoxy)-ethano-anthracene-9'-yl]-propyl}-1,7-dicyanoperylene-3,4:9,10-bis(dicarboximide) and N,N'-bis{3-[9',10'-dihydro-9',10'-(1",2"-dicarbomethoxy)-ethano-anthracene-9'-yl]-propyl}-1,6-dicyanoperylene-3,4:9,10-bis(dicarboximide) as purple crystals (0.072 g, 35% yield). $^1$H NMR (CDCl$_3$, 500 MHz) δ 9.72 (2H, d, J=8.0 Hz), 9.08 and 9.03 (2H, s), 8.98 and 8.93 (2H, d, J=8.0 and 8.5 Hz), 7.46-7.43 (4H, m), 7.31-7.12 (12H, m), 4.63 (2H, s), 4.54-4.52 (4H, m), 3.51 (12H, s), 3.33 (2H, d, J=11.0 Hz), 3.21 (2H, d, J=11.0 Hz), 2.68-2.59 (4H, m), 2.42-2.41 (4H, m); MS-MALDI (calcd. 1164.36): 1164.15.

Figure 8:
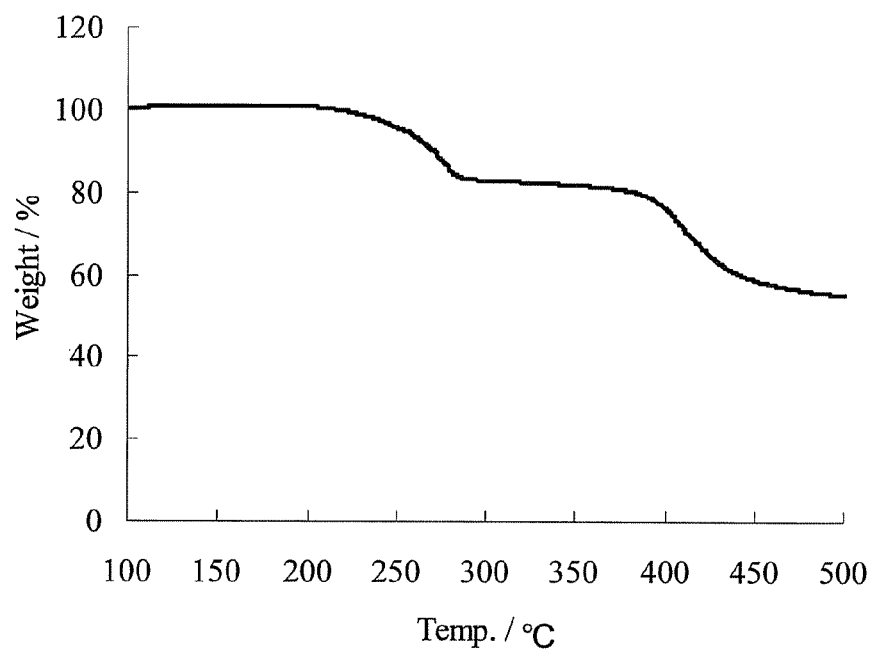
FIGS. 8(a) and 8(b) provide a thermogravimetric analysis plot and a Differential Scanning Calorimetry (DSC) trace, respectively, of a certain embodiment (PDI3A-DMF-CN$_2$) of the present teachings with the calorimetry conducted at a heating rate of 10° C./min under nitrogen atmosphere.
Figure 8:
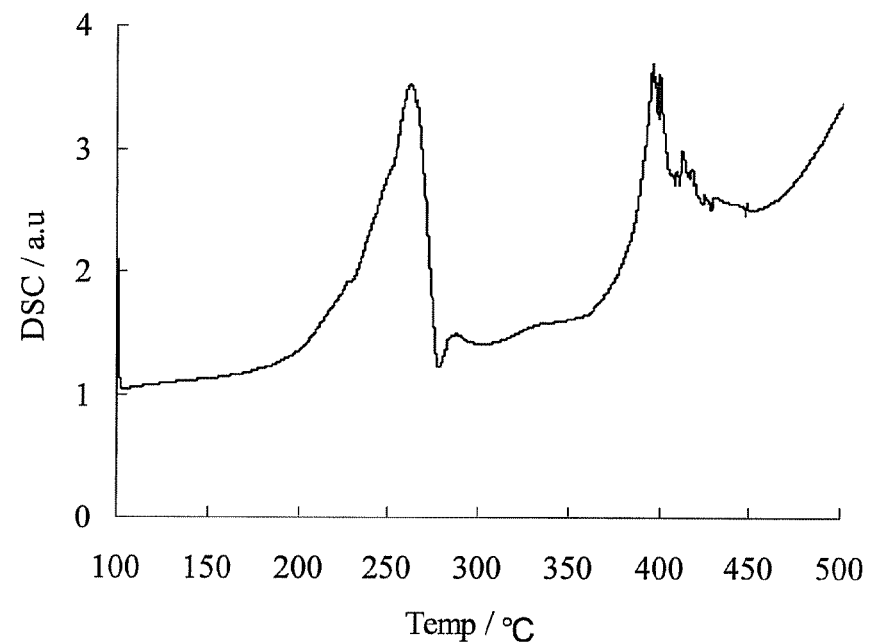
Figure 9:
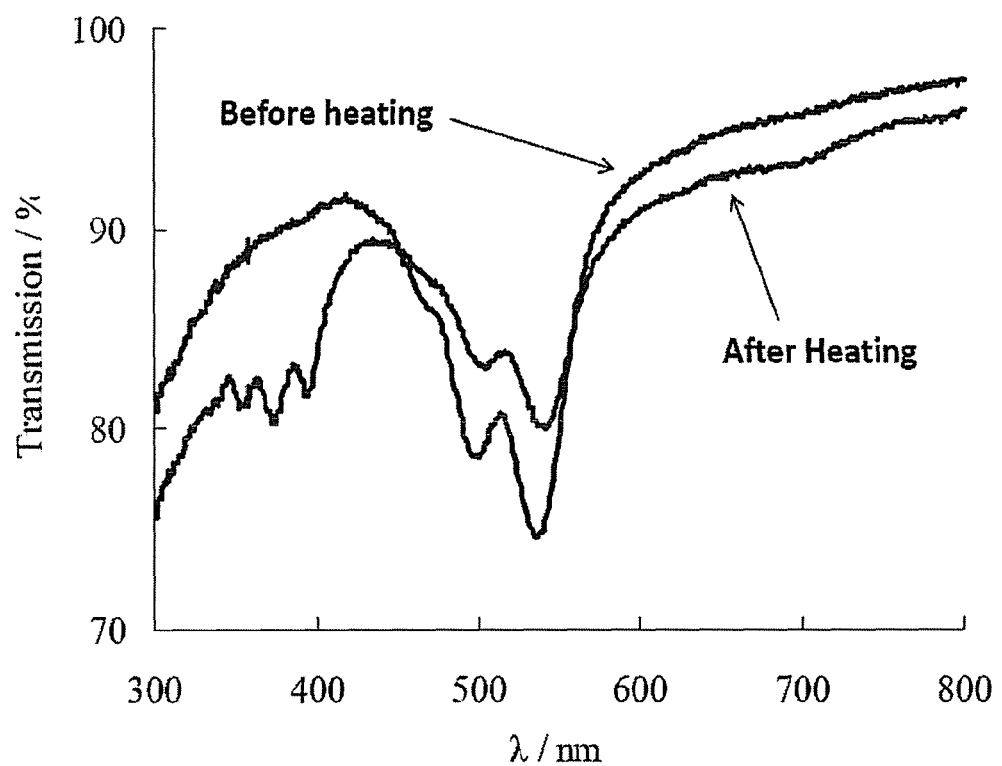
FIG. 9 provides transmission spectra of certain embodiments (a spin-coated film of PDI3A-DMF-CN$_2$ on a glass plate) of the present teaching before heating and after heating at 300° C. under nitrogen atmosphere for 1 hour.

FIGS. 8(a) and 8(b) show a thermogravimetric curve and a DSC trace of PDI3A-DMF-CN$_2$, respectively (heating rate: 10° C./min under N$_2$). FIG. 9 shows transmission spectra of a spin-coated film of PDI3A-DMF-CN$_2$ on a glass plate before heating and after heating at 300° C. under N$_2$ for 1 hour, respectively.

Example 16

Preparation of N,N'-bis{3-[9',10'-dihydro-9',10'-(1",2"-ditrifluoromethyl)-etheno-anthracene-9'-yl]-propyl}-1,7-dibromoperylene-3,4:9,10-bis(dicarboximide) 23 (PDI3A-DFMA-Br$_2$)

To a solution of N,N'-bis(3-(anthracen-9-yl)-propyl)-1,7-dibromoperylene-3,4:9,10-bis(dicarboximide) (1.00 g, 1.02 mmol, Example 8) in o-xylene (40 mL), dimethylmaleate (7.35 g, 51.0 mmol) was added at room temperature, and the mixture was heated to reflux for 3 days. The solution was cooled to room temperature and filtered. The filtrate was concentrated and MeOH (200 mL) was added. The resulting solid was collected by filtration, washed with MeOH and dried in a vacuum oven. The crude product was further purified by precipitation from hot CHCl$_3$ and MeOH to give N,N'-bis{3-[9',10'-dihydro-9',10'-(1",2"-ditrifluoromethyl)-etheno-anthracene-9'-yl]-propyl}-1,7-dibromoperylene-3,4:9,10-bis(dicarboximide) as red crystals (0.46 g, 35% yield). $^1$H NMR (CDCl$_3$, 500 MHz) δ 9.50 (2H, d, J=8.0 Hz), 8.97 (2H, s), 8.75 (2H, d, J=8.5 Hz), 7.47-7.43 (4H, m), 7.30-7.10 (12H, m), 4.62 (2H, s), 4.54-4.50 (4H, m), 3.51 (12H, s), 3.34 (2H, d, J=11.5 Hz), 3.20 (2H, d, J=11.0 Hz), 2.67-2.57 (4H, m), 2.42-2.40 (4H, m); MS-MALDI (calcd. 1270.19): 1271.22; Elemental Analysis (calcd C, 66.05; H, 4.12, N: 2.20): C, 65.45; H, 4.59; N: 1.80.

Example 17

Preparation of N,N'-bis{3-[9',10'-dihydro-9',10'-(1",2"-ditrifluoromethyl)-etheno-anthracene-9'-yl]-propyl}-1,7-dicyanoperylene-3,4:9,10-bis(dicarboximide) 24 (PDI3A-DFMA-CN$_2$)

To a solution of N,N'-bis{3-[9',10'-dihydro-9',10'-(1",2"-ditrifluoromethyl)-etheno-anthracene-9'-yl]-propyl}-1,7-dibromoperylene-3,4:9,10-bis(dicarboximide) (0.226 g, 0.178 mmol, Example 16) in dry DMF (45 mL), CuCN (0.286 g, 3.20 mmol) was added at room temperature, and the mixture was heated to reflux for 12 hours. The solution was cooled to room temperature and poured into MeOH (300 mL). The resulting solid was collected by filtration, washed with MeOH and dried in a vacuum oven. The crude product was further purified by reprecipitation from hot CHCl$_3$, H$_2$O, and MeOH to give a mixture of N,N'-bis{3-[9',10'-dihydro-9',10'-(1",2"-ditrifluoromethyl)-etheno-anthracene-9'-yl]-propyl}-1,7-dicyanoperylene-3,4:9,10-bis(dicarboximide) and N,N'-bis{3-[9',10'-dihydro-9',10'-(1",2"-ditrifluoromethyl)-etheno-anthracene-9'-yl]-propyl}-1,6-dicyanoperylene-3,4:9,10-bis(dicarboximide) as purple crystals (0.072 g, 35% yield). $^1$H NMR (CDCl$_3$, 500 MHz) δ 9.72 (2H, d, J=8.0 Hz), 9.08 and 9.03 (2H, s), 8.98 and 8.93 (2H, d, J=8.0 and 8.5 Hz), 7.46-7.43 (4H, m), 7.31-7.12 (12H, m), 4.63 (2H, s), 4.54-4.52 (4H, m), 3.51 (12H, s), 3.33 (2H, d, J=11.0 Hz), 3.21 (2H, d, J=11.0 Hz), 2.68-2.59 (4H, m), 2.42-2.41 (4H, m); MS-MALDI (calcd. 1164.36): 1164.15; Elemental Analysis (calcd C, 74.22; H, 4.50; N, 4.81): C, 73.84; H, 4.84; N, 4.60.

Example 18

Preparation of N,N'-bis[(methylurazolyl)anthracene-9'-yl-propyl]-1,7-dibromoperylene-3,4:9,10-bis(dicarboximide) 31 (PDI3A-MU—Br$_2$)

To a solution of N,N'-bis(3-(anthracen-9-yl)-propyl)-1,7-dibromoperylene-3,4:9,10-bis(dicarboximide) (0.30 g, 0.30 mmol, Example 8) in o-xylene (12 mL), 4-methylurazole (0.21 g, 1.82 mmol) and triphenylbismuth (1.01 g, 2.01 mmol) were added at room temperature, and the mixture was heated at 110° C. for 14 hours. The solution was cooled to room temperature and filtered. The filtrate was poured into MeOH (200 mL), and the resulting solid was filtered, washed with MeOH, and dried in a vacuum oven. The product was further purified by reprecipitation from hot CHCl$_3$ and MeOH to give N,N'-bis[(methylurazolyl)anthracene-9'-yl-propyl]-1,7-dibromoperylene-3,4:9,10-bis(dicarboximide) as red crystals (0.33 g, 88% yield). $^1$H NMR (CDCl$_3$, 500 MHz) δ 9.50 (2H, d, J=8.0 Hz), 8.98 (2H, s), 8.75 (2H, d, J=8.5 Hz), 7.46 (4H, dd, J=6.0 Hz), 7.39 (4H, dd, J=7.0 Hz), 7.29 (4H, t, J=7.5 Hz), 7.23 (4H, t, J=7.5 Hz), 6.14 (1H, s), 4.62 (4H, m), 3.21-3.17 (4H, m), 2.76 (6H, s), 2.73-2.61 (4H, m); MS-MALDI (calcd. 1210.15): 1211.92; Elemental Analysis (calcd C, 63.48; H, 3.50; N, 9.25): C, 65.57; H, 4.72; N, 8.05.

Example 19

Preparation of N,N'-bis[(methylurazolyl)anthracene-9'-yl-propyl]-1,7-dicyanoperylene-3,4:9,10-bis(dicarboximide) 32 (PDI3A-MU—CN$_2$)

To a solution of N,N'-bis[(methylurazolyl)anthracene-9'-yl-propyl]-1,7-dibromoperylene-3,4:9,10-bis(dicarboximide) (0.15 g, 0.124 mmol, Example 18) in dry DMF (31 mL), CuCN (0.20 g, 2.23 mmol) was added at room temperature, and the mixture was heated to reflux for 12 hours. The solution was cooled to room temperature and poured into MeOH (200 mL). The resulting solid was filtered, washed with MeOH and dried in a vacuum oven. The product was further washed with hot DMSO to give N,N'-bis[(methylurazolyl)anthracene-9'-yl-propyl]-1,7-dicyanoperylene-3,4:9,10-bis(dicarboximide) as purple crystals (0.104 g, 96% yield). $^1$H NMR (C$_2$D$_2$Cl$_4$, 500 MHz) δ 9.74 (d, 2H, J=8.0 Hz), 9.04 (s, 2H), 8.99 (d, 2H, J=8.0 Hz), 8.43 (s, 2H), 8.42 (d, 4H, J=7.5 Hz), 8.10 (d, 4H, J=8.0 Hz), 7.67 (t, 4H, J=7.5, 8.0 Hz), 7.59 (t, 4H, J=8.0, 7.0 Hz), 4.62 (m, 4H), 3.89 (m, 4H), 2.42 (m, 4H); MS-MALDI (calcd. 876.27): 876.23.

Example 21

Converting Soluble Precursors to Semiconductor Materials

A solution of semiconductor precursor (1-10 mg/mL) in an organic solvent (CHCl$_3$, toluene, xylene, EtOH, AcOEt) was spin-coated on a Si substrate. The resulting film was heated at an elevated temperature (e.g., 120° C.-170° C.) for a predetermined period of time (e.g., 5-50 minutes). A change in the appearance of the film can be observed. MS-MALDI analysis confirms conversion to a semiconductor film.

Example 22

Optical and Electrochemical Properties of Compounds of the Present Teachings

The optical properties and HOMO-LUMO energy gaps ($E_{gap}$) of certain compounds of the present teachings were determined. The results are presented in Table 3.

TABLE 3

Optical properties and HOMO-LUMO energy gaps ($E_{gap}$) of compounds of the present teachings.

| Compound | $\lambda_{abs}$ (nm) | $\lambda_{em}$ (nm)[c] | $E_{gap}$ (eV)[d] |
|---|---|---|---|
| PDI3A-DMF-Br$_2$[a] | 519 | 542 | 2.27 |
| PDI3A-DMF-CN$_2$[a] | 522 | 534 | 2.11 |
| PDI3A-Br$_2$[a] | 520 | — | 2.28 |
| PDI3A-CN$_2$[b] | 524 | — | 2.20 |
| PDI-CN$_2$[a] | 530 | 547 | 2.40 |

[a] in THF,
[b] in CHCl$_3$,
[c] $\lambda_{ex}$ = 365 nm, and
[d] determined by absorption onsets.

The electrochemical properties of certain compounds of the present teachings were determined. The results are presented in Table 4.

TABLE 4

Electrochemical properties of compounds of the present teachings.

| Compound | $E^1_{red}$ (V) | $E^2_{red}$ (V) | $E^3_{red}$ (V) | $E^1_{ox}$ (V) |
|---|---|---|---|---|
| PDI3A-DMF-Br$_2$[a] | −0.46 | −0.76 | — | — |
| PDI3A-DMF-CN$_2$[a] | −0.20 | −0.58 | — | — |
| PDI3A-Br$_2$[b] | −0.52 | −0.75 | −1.75 | +1.30 |
| PDI3A-CN$_2$[c] | −0.15 | −0.57 | −1.17 | +1.59 |
| PDI-CN$_2$[a] | −0.07 | −0.40 | — | — |

[a] in THF,
[b] in CHCl$_3$, and
[c] In C$_2$H$_2$Cl$_4$.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A compound of formula I':

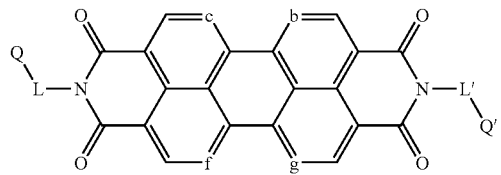

I' wherein:
b, c, f and g independently are CH or CR$^a$, provided that at least one of b, c, f and g is CR$^a$;
L and L' independently are a divalent C$_{1-20}$ alkyl group or a covalent bond; and
Q and Q' independently are an anthracenyl group optionally substituted with 1-10 R$^{a'}$ groups,
wherein:
R$^a$ and R$^{a'}$, at each occurrence, independently are a) halogen, b) —CN, c) —NO$_2$, d) —O—Y—R$^d$, e) —NR$^e$—Y—R$^f$, f) —N(O)R$^e$—Y—R$^f$, g) —S(O)$_m$R$^e$, h) —S(O)$_m$O—Y—R$^d$, i) —S(O)$_m$NR$^e$—Y—R$^f$, j) C(O)R$^e$, k) —C(O)O—Y—R$^d$, l) —C(O)NR$^e$—Y—R$^f$, m) —C(S)NR$^e$—Y—R$^f$, n) —Si(C$_{1-20}$ alkyl)$_3$, o) a C$_{1-20}$ alkyl group, p) a C$_{2-20}$ alkenyl group, q) a C$_{2-20}$ alkynyl group, r) a —Y—C$_{3-10}$ cycloalkyl group, s) a —Y—C$_{6-14}$ aryl group, t) a —Y-3-12 membered cycloheteroalkyl group, or u) a —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-4 R$^g$ groups;
R$^d$, at each occurrence, is a) H, b) —C(O)R$^e$, c) —C(O)NR$^e$R$^f$, d) —C(S)R$^e$, e) —C(S)NR$^e$R$^f$, f) a C$_{1-20}$ alkyl group, g) a C$_{2-20}$ alkenyl group, h) a C$_{2-20}$ alkynyl group, i) —Y—C$_{3-10}$ cycloalkyl group, j) —Y—C$_{6-14}$ aryl group, k) —Y-3-12 membered cycloheteroalkyl group, or l) —Y-5-14 membered heteroaryl group, wherein each of the C$_{1-20}$ alkyl group, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-4 R$^g$ groups;
R$^e$ and R$^f$, at each occurrence, independently are a) H, b) —OH, c) —SH, d) —S(O)$_2$OH, e) —C(O)OH, f) —C(O)NH$_2$, g) —C(S)NH$_2$, h) —O—C$_{1-20}$ alkyl, i) —O—Y—C$_{6-14}$ aryl, j) —C(O)—C$_{1-20}$ alkyl, k) —C(O)—OC$_{1-20}$ alkyl, l) —C(S)N(C$_{1-20}$ alkyl)$_2$, m) —C(S)NH—C$_{1-20}$ alkyl, n) —C(O)NH—C$_{1-20}$ alkyl, o) —C(O)N(C$_{1-20}$ alkyl)$_2$, p) —S(O)$_m$—C$_{1-20}$ alkyl, q) —S(O)$_m$—OC$_{1-20}$ alkyl, r) —C(O)—Y—C$_{6-14}$ aryl, s) —C(O)—O—Y—C$_{6-14}$ aryl, t) —C(S)N(—Y—C$_{6-14}$ aryl)$_2$, u) —C(S)N(C$_{1-20}$ alkyl) —Y—C$_{6-14}$ aryl, v) —C(S)NH—Y—C$_{6-14}$ aryl, w) —C(O)NH—Y—C$_{6-14}$ aryl, x) —C(O)N(C$_{1-20}$ alkyl) —Y—C$_{6-14}$ aryl, y) —C(O)N(Y—C$_{6-14}$ aryl)$_2$, z) —S(O)$_m$—Y—C$_{6-14}$ aryl, aa) —S(O)$_m$—O—Y—C$_{6-14}$ aryl, ab) a C$_{1-20}$ alkyl group, ac) a C$_{2-20}$ alkenyl group, ad) a C$_{2-20}$ alkynyl group, ae) —Y—C$_{3-10}$ cycloalkyl group, af) —Y—C$_{6-14}$ aryl group, ag) —Y-3-12 membered cycloheteroalkyl group, or ah) —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl groups, the 3-12 membered cycloheteroalkyl group, and the 5-14 membered heteroaryl group optionally is substituted with 1-4 R$^g$ groups;
R$^g$, at each occurrence, is a) halogen, b) —CN, c) —NO$_2$, d) oxo, e) —OH, f) —NH$_2$, g) —NH(C$_{1-20}$ alkyl), h) —N(C$_{1-20}$ alkyl)$_2$, i) —NH(C$_{1-6}$ alkyl-C$_{6-14}$ aryl), j) —N(C$_{1-20}$ alkyl)(C$_{1-6}$ alkyl-C$_{6-14}$ aryl), k) —N(C$_{1-6}$ alkyl-C$_{6-14}$ aryl)$_2$, l) —S(O)$_m$H, m) —S(O)$_m$C$_{1-20}$ alkyl, n) —S(O)$_2$OH, o) —S(O)$_m$—OC$_{1-20}$ alkyl, p) —CHO, q) —C(O)—C$_{1-20}$ alkyl, r) —C(O)OH, s) —C(O)—OC$_{1-20}$ alkyl, t) —C(O)NH$_2$, u) —C(O)NH—C$_{1-20}$ alkyl, v) —C(O)N(C$_{1-20}$ alkyl)$_2$, w) —C(O)NH(C$_{1-6}$ alkyl-C$_{6-14}$ aryl), x) —C(O)N(C$_{1-20}$ alkyl)(C$_{1-6}$ alkyl-C$_{6-14}$ aryl), y) —C(O)N(C$_{1-6}$ alkyl-C$_{6-14}$ aryl)$_2$, z) —C(S)NH$_2$, aa) —C(S)NH—C$_{1-20}$ alkyl, ab) —C(S)N(C$_{1-20}$ alkyl)$_2$, ac) —C(S)NH(C$_{1-6}$ alkyl-C$_{6-14}$ aryl), ad) —C(S)N(C$_{1-20}$ alkyl)(C$_{1-6}$ alkyl-C$_{6-14}$ aryl), ae) —C(S)N(C$_{1-6}$ alkyl-C$_{6-14}$ aryl)$_2$, af) —S(O)$_m$NH$_2$, ag) —S(O)$_m$NH(C$_{1-20}$ alkyl), ah) —S(O)$_m$N(C$_{1-20}$ alkyl)$_2$, ai) —S(O)$_m$NH(C$_{1-6}$ alkyl-C$_{6-14}$ aryl), aj) —S(O)$_m$N(C$_{1-20}$ alkyl)(C$_{1-6}$ alkyl-C$_{6-14}$ aryl), ak) —S(O)$_m$N(C$_{1-6}$ alkyl-C$_{6-14}$ aryl)$_2$, al) —Si(C$_{1-20}$ alkyl)$_3$, am) a C$_{1-20}$ alkyl group, an) a C$_{2-20}$ alkenyl group, ao) a C$_{2-10}$ alkynyl group, ap) a C$_{1-20}$ alkoxy group, aq) a C$_{1-20}$ alkylthio group, ar) a C$_{1-20}$ haloalkyl group, as) a C$_{3-10}$ cycloalkyl group, at) a $C_{6-14}$ aryl group, au) a 3-12 membered cycloheteroalkyl group, or av) a 5-14 membered heteroaryl group;

Y, at each occurrence, is a) a divalent $C_{1-20}$ alkyl group, b) a divalent $C_{1-20}$ haloalkyl group, or c) a covalent bond; and m, at each occurrence, is 0, 1 or 2.

2. The compound of claim 1, wherein Q and Q' are selected from:

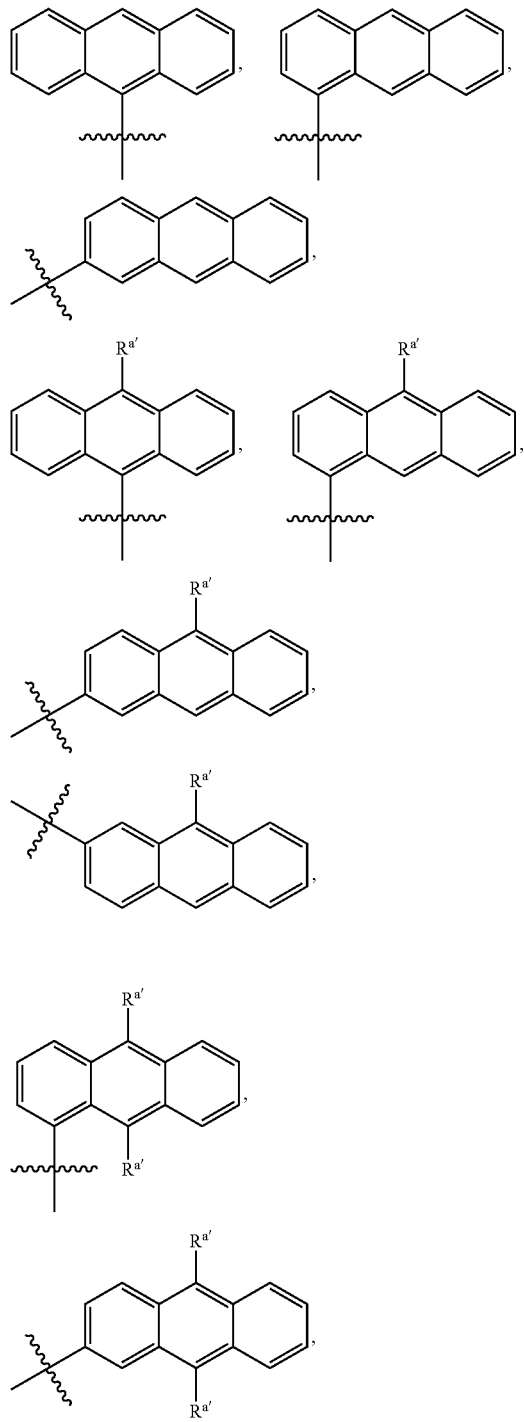

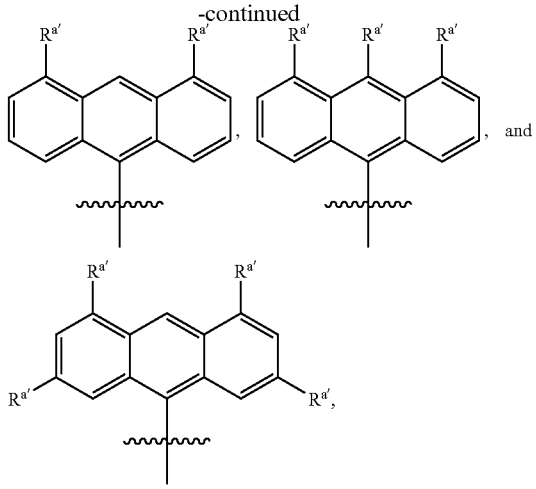

wherein $R^{a'}$, at each occurrence, is selected from F, —CN, —NH$_2$, —NH($C_{1-20}$ alkyl), —N($C_{1-20}$ alkyl)$_2$, —NH($C_{1-6}$ alkyl-$C_{6-14}$ aryl), —N($C_{1-20}$ alkyl)($C_{1-6}$ alkyl-$C_{6-14}$ aryl), —N($C_{1-6}$ alkyl-$C_{6-14}$ aryl)$_2$, —CHO, —C(O)—$C_{1-20}$ alkyl, —C(O)OH, —C(O)—O$C_{1-20}$ alkyl, a straight chain $C_{1-10}$ alkyl group, and a branched $C_{1-10}$ alkyl group.

3. The compound of claim 1 selected from:

N,N'-bis(9-anthracenyl)-1,7-dibromoperylene-3,4:9,10-bis(dicarboximide),
N,N'-bis(9-anthracenyl)-1,6-dibromoperylene-3,4:9,10-bis(dicarboximide),
N,N'-bis(9-anthracenyl)-1,7-dicyanoperylene-3,4:9,10-bis(dicarboximide),
N,N'-bis(9-anthracenyl)-1,6-dicyanoperylene-3,4:9,10-bis(dicarboximide),
N,N'-bis(anthracen-9-ylmethyl)-1,7-dibromoperylene-3,4:9,10-bis(dicarboximide),
N,N'-bis(anthracen-9-ylmethyl)-1,6-dibromoperylene-3,4:9,10-bis(dicarboximide),
N,N'-bis(anthracen-9-ylmethyl)-1,7-dicyanoperylene-3,4:9,10-bis(dicarboximide),
N,N'-bis(anthracen-9-ylmethyl)-1,6-dicyanoperylene-3,4:9,10-bis(dicarboximide),
N,N'-bis(2-(anthracen-9-yl)-ethyl)-1,7-dibromoperylene-3,4:9,10-bis(dicarboximide),
N,N'-bis(2-(anthracen-9-yl)-ethyl)-1,6-dibromoperylene-3,4:9,10-bis(dicarboximide),
N,N'-bis(2-(anthracen-9-yl)-ethyl)-1,7-dicyanoperylene-3,4:9,10-bis(dicarboximide),
N,N'-bis(2-(anthracen-9-yl)-ethyl)-1,6-dicyanoperylene-3,4:9,10-bis(dicarboximide),
N,N'-bis(3-(anthracen-9-yl)-propyl)-1,7-dibromoperylene-3,4:9,10-bis(dicarboximide),
N,N'-bis(3-(anthracen-9-yl)-propyl)-1,6-dibromoperylene-3,4:9,10-bis(dicarboximide),
N,N'-bis(3-(anthracen-9-yl)-propyl)-1,7-dicyanoperylene-3,4:9,10-bis(dicarboximide),
N,N'-bis(3-(anthracen-9-yl)-propyl)-1,6-dicyanoperylene-3,4:9,10-bis(dicarboximide),
N,N'-bis(2-(10-cyano-anthracen-9-yl)-ethyl)-1,7-dicyanoperylene-3,4:9,10-bis(dicarboximide),
N,N'-bis(2-(10-cyano-anthracen-9-yl)-ethyl)-1,6-dicyanoperylene-3,4:9,10-bis(dicarboximide),
N,N'-bis(2-(10-hexyl-anthracen-9-yl)-ethyl)-1,7-dicyanoperylene-3,4:9,10-bis(dicarboximide),
N,N'-bis(2-(10-hexyl-anthracen-9-yl)-ethyl)-1,6-dicyanoperylene-3,4:9,10-bis(dicarboximide), N,N'-bis(2-anthracenyl)-1,7-dicyanoperylene-3,4:9,10-bis(dicarboximide), N,N'-bis(2-anthracenyl)-1,6-dicyanoperylene-3,4:9,10-bis(dicarboximide), N,N'-bis(3-(anthracen-2-yl)-propyl)-1,7-dicyanoperylene-3,4:9,10-bis(dicarboximide), and N,N'-bis(3-(anthracen-2-yl)-propyl)-1,6-dicyanoperylene-3,4:9,10-bis(dicarboximide).

4. A thin film semiconductor material comprising the compound of claim 1.

5. A compound of formula II':

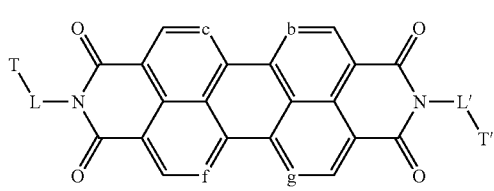

wherein:
b, c, f and g independently are CH or $CR^a$, provided that at least one of b, c, f and g is $CR^a$;

L and L' independently are a divalent $C_{1-20}$ alkyl group or a covalent bond; and T and T' independently are selected from:

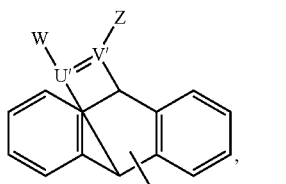,

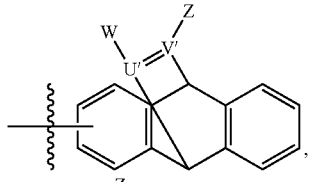,

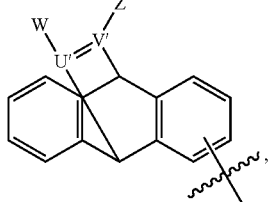,

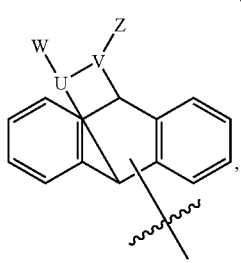,

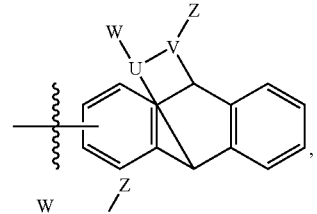,

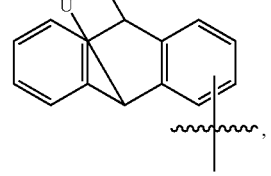,

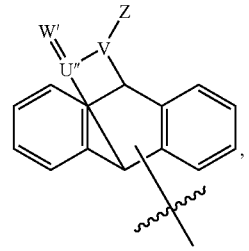,

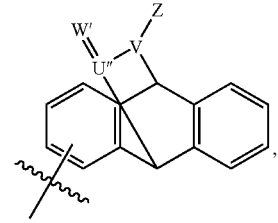,

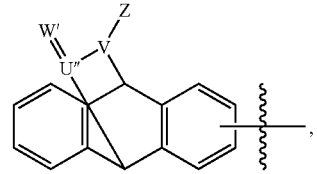,

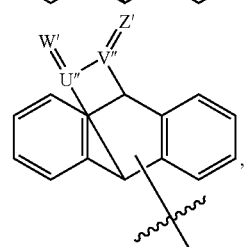,

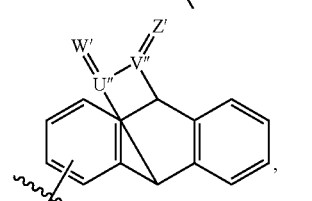,

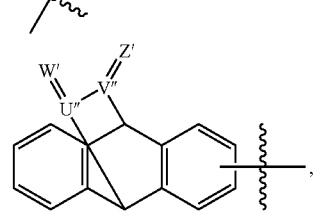,

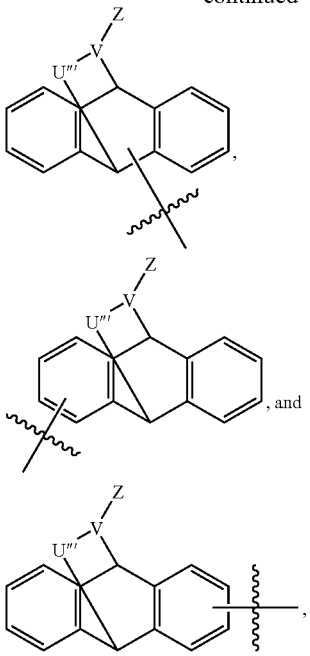

wherein each of these groups can be optionally substituted with 1-10 $R^{a'}$ groups, and U and V, at each occurrence, independently are CH, $CR^h$, $SiR^i$, N or P;

U', U'', V' and V''' independently are C or Si;

U'''' is O, $S(O)_m$, or Se;

W and Z, at each occurrence, independently are H or $R^{h'}$, or

W and Z, together with U and V, form a $C_{3-10}$ cycloalkyl group or a 3-12 membered cycloheteroalkyl group, wherein the $C_{3-10}$ cycloalkyl group and the 3-12 membered cycloheteroalkyl group optionally is substituted with 1-4 $R^n$ groups;

W' and Z', at each occurrence, independently are O, $CR^jR^{j'}$ or $NR^m$;

$R^a$ and $R^{a'}$, at each occurrence, independently are a) halogen, b) —CN, c) —$NO_2$, d) —O—Y—$R^d$, e) —$NR^e$—Y—$R^f$, f) —N(O)$R^e$—Y—$R^f$, g) —S(O)$_m R^e$, h) —S(O)$_m$ O—Y—$R^d$, i) —S(O)$_m NR^e$—Y—$R^f$, j) —C(O)$R^e$, k) —C(O)O—Y—$R^d$, l) —C(O)$NR^e$—Y—$R^f$, m) —C(S)$NR^e$—Y—$R^f$, n) —Si($C_{1-20}$ alkyl)$_3$, o) a $C_{1-20}$ alkyl group, p) a $C_{2-20}$ alkenyl group, q) a $C_{2-20}$ alkynyl group, r) a —Y—$C_{3-10}$ cycloalkyl group, s) a —Y—$C_{6-14}$ aryl group, t) a —Y-3-12 membered cycloheteroalkyl group, or u) a —Y-5-14 membered heteroaryl group, wherein each of the $C_{1-20}$ alkyl groups, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group optionally is substituted with 1-4 $R^g$ groups;

$R^d$, at each occurrence, is a) H, b) —C(O)$R^e$, c) —C(O)$NR^eR^f$, d) —C(S)$R^e$, e) —C(S)$NR^eR^f$, f) a $C_{1-20}$ alkyl group, g) a $C_{2-20}$ alkenyl group, h) a $C_{2-20}$ alkynyl group, i) —Y—$C_{3-10}$ cycloalkyl group, j) —Y—$C_{6-14}$ aryl group, k) —Y-3-12 membered cycloheteroalkyl group, or l) —Y-5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group optionally is substituted with 1-4 $R^g$ groups;

$R^e$ and $R^f$, at each occurrence, independently are a) H, b) —OH, c) —SH, d) —$S(O)_2OH$, e) —C(O)OH, f) —C(O)$NH_2$, g) —C(S)$NH_2$, h) —O—$C_{1-20}$ alkyl, i) —O—Y—$C_{6-14}$ aryl, j) —C(O)—$C_{1-20}$ alkyl, k) —C(O)—O$C_{1-20}$ alkyl, l) —C(S)N($C_{1-20}$ alkyl)$_2$, m) —C(S)NH—$C_{1-20}$ alkyl, n) —C(O)NH—$C_{1-20}$ alkyl, o) —C(O)N($C_{1-20}$ alkyl)$_2$, p) —S(O)$_m$—$C_{1-20}$ alkyl, q) —S(O)$_m$—O$C_{1-20}$ alkyl, r) —C(O)—Y—$C_{6-14}$ aryl, s) —C(O)—O—Y—$C_{6-14}$ aryl, t) —C(S)N(—Y—$C_{6-14}$ aryl)$_2$, u) —C(S)N($C_{1-20}$ alkyl) —Y—$C_{6-14}$ aryl, v) —C(S)NH—Y—$C_{6-14}$ aryl, w) —C(O)NH—Y—$C_{6-14}$ aryl, x) —C(O)N($C_{1-20}$ alkyl) —Y—$C_{6-14}$ aryl, y) —C(O)N(Y—$C_{6-14}$ aryl)$_2$, z) —S(O)$_m$—Y—$C_{6-14}$ aryl, aa) —S(O)$_m$—O—Y—$C_{6-14}$ aryl, ab) a $C_{1-20}$ alkyl group, ac) a $C_{2-20}$ alkenyl group, ad) a $C_{2-20}$ alkynyl group, ae) —Y—$C_{3-10}$ cycloalkyl group, af) —Y—$C_{6-14}$ aryl group, ag) —Y-3-12 membered cycloheteroalkyl group, or ah) —Y-5-14 membered heteroaryl group, wherein each of the $C_{1-20}$ alkyl groups, the $C_{2-20}$ alkenyl group, the $C_{2-20}$ alkynyl group, the $C_{3-10}$ cycloalkyl group, the $C_{6-14}$ aryl groups, the 3-12 membered cycloheteroalkyl group, and the 5-14 membered heteroaryl group optionally is substituted with 1-4 $R^g$ groups;

$R^g$, at each occurrence, is a) halogen, b) —CN, c) —$NO_2$, d) oxo, e) —OH, f) —$NH_2$, g) —NH($C_{1-20}$ alkyl), h) —N($C_{1-20}$ alkyl)$_2$, i) —NH($C_{1-6}$ alkyl-$C_{6-14}$ aryl), j) —N($C_{1-20}$ alkyl)($C_{1-6}$ alkyl-$C_{6-14}$ aryl), k) —N($C_{1-6}$ alkyl-$C_{6-14}$ aryl)$_2$, l) —$S(O)_m$H, m) —S(O)$_m$—$C_{1-20}$ alkyl, n) —$S(O)_2$ OH, o) —S(O)$_m$—O$C_{1-20}$ alkyl, p) —CHO, q) —C(O)—$C_{1-20}$ alkyl, r) —C(O)OH, s) —C(O)—O$C_{1-20}$ alkyl, t) —C(O)$NH_2$, u) —C(O)NH—$C_{1-20}$ alkyl, v) —C(O)N($C_{1-20}$ alkyl)$_2$, w) —C(O)NH ($C_{1-6}$ alkyl-$C_{6-14}$ aryl), x) —C(O)N($C_{1-20}$ alkyl)($C_{1-6}$ alkyl-$C_{6-14}$ aryl), y) —C(O)N($C_{1-6}$ alkyl-$C_{6-14}$ aryl)$_2$, z) —C(S)$NH_2$, aa) —C(S)NH—$C_{1-20}$ alkyl, ab) —C(S)N($C_{1-20}$ alkyl)$_2$, ac) —C(S)NH($C_{1-6}$ alkyl-$C_{6-14}$ aryl), ad) —C(S)N($C_{1-20}$ alkyl)($C_{1-6}$ alkyl-$C_{6-14}$ aryl), ae) —C(S)N($C_{1-6}$ alkyl-$C_{6-14}$ aryl)$_2$, af) —S(O)$_m NH_2$, ag) —S(O)$_m$ NH($C_{1-20}$ alkyl), ah) —S(O)$_m$N($C_{1-20}$ alkyl)$_2$, ai) —S(O)$_m$NH($C_{1-6}$ alkyl-$C_{6-14}$ aryl), aj) —S(O)$_m$N ($C_{1-20}$ alkyl)($C_{1-6}$ alkyl-$C_{6-14}$ aryl), ak) —S(O)$_m$N($C_{1-6}$ alkyl-$C_{6-14}$ aryl)$_2$, al) —Si($C_{1-20}$ alkyl)$_3$, am) a $C_{1-20}$ alkyl group, an) a $C_{2-10}$ alkenyl group, ao) a $C_{2-10}$ alkynyl group, ap) a $C_{1-20}$ alkoxy group, aq) a $C_{1-20}$ alkylthio group, ar) a $C_{1-20}$ haloalkyl group, as) a $C_{3-10}$ cycloalkyl group, at) a $C_{6-14}$ aryl group, au) a 3-12 membered cycloheteroalkyl group, or av) a 5-14 membered heteroaryl group;

$R^h$ and $R^{h'}$, at each occurrence, independently are a) halogen, b) —CN, c) —$NO_2$, d) —O—Y—$R^k$, e) —NR—Y—$R^m$, f) —N(O)R—Y—$R^m$, g) —S(O)$_m R^l$, h) —S(O)$_m$ O—Y—$R^k$, i) —S(O)$_m NR^l$—Y—$R^m$, j) —C(O)$R^l$, k) —C(O)O—Y—$R^k$, l) —C(O)$NR^l$—Y—$R^m$, m) —C(S)$NR^l$—Y—$R^m$, n) —Si($C_{1-20}$ alkyl)$_3$, o) a $C_{1-20}$ alkyl group, p) a $C_{2-20}$ alkenyl group, q) a $C_{2-20}$ alkynyl group, r) a —Y—$C_{3-10}$ cycloalkyl group, s) a —Y—$C_{6-14}$ aryl group, t) a —Y-3-12 membered cycloheteroalkyl group, or u) a —Y-5-14 membered heteroaryl group, wherein each of the $C_{1-20}$ alkyl groups, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group optionally is substituted with 1-4 $R^n$ groups;

$R^i$, at each occurrence, is a) H, b) a $C_{1-20}$ alkyl group, c) a —Y—$C_{6-14}$ aryl group, d) an —O—$C_{1-20}$ alkyl group, or e) an —O—Y—$C_{6-14}$ aryl group, wherein each of the $C_{1-20}$ alkyl groups and the $C_{6-14}$ aryl groups optionally is substituted with 1-4 $R^n$ groups;

$R^j$ and $R^{j'}$, at each occurrence, independently are a) H, b) halogen, c) —CN, d) CHO, e) —C(O)—O$C_{1-20}$ alkyl, f) a $C_{1-20}$ alkyl group, or g) a —Y—$C_{6-14}$ aryl group, wherein each of the $C_{1-20}$ alkyl groups and the $C_{6-14}$ aryl group optionally is substituted with 1-4 $R^n$ groups;

$R^k$, at each occurrence, is a) H, b) —C(O)$R^e$, c) —C(O)N$R^e R^f$, d) —C(S)$R^e$, e) —C(S)N$R^e R^f$, f) a $C_{1-20}$ alkyl group, g) a $C_{2-20}$ alkenyl group, h) a $C_{2-20}$ alkynyl group, i) —Y—$C_{3-10}$ cycloalkyl group, j) —Y—$C_{6-14}$ aryl group, k) —Y-3-12 membered cycloheteroalkyl group, or l) —Y-5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group optionally is substituted with 1-4 $R^n$ groups;

$R^l$ and $R^m$, at each occurrence, independently are a) H, b) —OH, c) —SH, d) —S(O)$_2$ OH, e) —C(O)OH, f) —C(O)NH$_2$, g) —C(S)NH$_2$, h) —O$C_{1-20}$ alkyl, i) —O—Y—$C_{6-14}$ aryl, j) —C(O)—$C_{1-20}$ alkyl, k) —C(O)—O$C_{1-20}$ alkyl, l) —C(S)N($C_{1-20}$ alkyl)$_2$, m) —C(S)NH—$C_{1-20}$ alkyl, n) —C(O)NH—$C_{1-20}$ alkyl, o) —C(O)N($C_{1-20}$ alkyl)$_2$, p) —S(O)$_m$—$C_{1-20}$ alkyl, q) —S(O)$_m$—O$C_{1-20}$ alkyl, r) —C(O)—Y—$C_{6-14}$ aryl, s) —C(O)—O—Y—$C_{6-14}$ aryl, t) —C(S)N(—Y—$C_{6-14}$ aryl)$_2$, u) —C(S)N($C_{1-20}$ alkyl) —Y—$C_{6-14}$ aryl, v) —C(S)NH—Y—$C_{6-14}$ aryl, w) —C(O)NH—Y—$C_{6-14}$ aryl, x) —C(O)N($C_{1-20}$ alkyl) —Y—$C_{6-14}$ aryl, y) —C(O)N(Y—$C_{6-14}$ aryl)$_2$, z) —S(O)$_m$—Y—$C_{6-14}$ aryl, aa) —S(O)$_m$—O—Y—$C_{6-14}$ aryl, ab) a $C_{1-20}$ alkyl group, ac) a $C_{2-20}$ alkenyl group, ad) a $C_{2-20}$ alkynyl group, ae) —Y—$C_{3-10}$ cycloalkyl group, af) —Y—$C_{6-14}$ aryl group, ag) —Y-3-12 membered cycloheteroalkyl group, or ah) —Y-5-14 membered heteroaryl group, wherein each of the $C_{1-20}$ alkyl groups, the $C_{2-20}$ alkenyl group, the $C_{2-20}$ alkynyl group, the $C_{3-10}$ cycloalkyl group, the $C_{6-14}$ aryl groups, the 3-12 membered cycloheteroalkyl group, and the 5-14 membered heteroaryl group optionally is substituted with 1-4 $R^n$ groups;

$R^n$, at each occurrence, is a) halogen, b) —CN, c) —NO$_2$, d) oxo, e) —OH, f) —NH$_2$, g) —NH($C_{1-20}$ alkyl), h) —N($C_{1-20}$ alkyl)$_2$, i) —NH($C_{1-6}$ alkyl-$C_{6-14}$ aryl), j) —N($C_{1-20}$ alkyl)($C_{1-6}$ alkyl-$C_{6-14}$ aryl), k) —N($C_{1-6}$ alkyl-$C_{6-14}$ aryl)$_2$, l) —S(O)$_m$H, m) —S(O)$_m$—$C_{1-20}$ alkyl, n) —S(O)$_2$ OH, o) —S(O)$_m$—O$C_{1-20}$ alkyl, p) —CHO, q) —C(O)—$C_{1-20}$ alkyl, r) —C(O)OH, s) —C(O)—O$C_{1-20}$ alkyl, t) —C(O)NH$_2$, u) —C(O)NH—$C_{1-20}$ alkyl, v) —C(O)N($C_{1-20}$ alkyl)$_2$, w) —C(O)NH ($C_{1-6}$ alkyl-$C_{6-14}$ aryl), x) —C(O)N($C_{1-20}$ alkyl)($C_{1-6}$ alkyl-$C_{6-14}$ aryl), y) —C(O)N($C_{1-6}$ alkyl-$C_{6-14}$ aryl)$_2$, z) —C(S)NH$_2$, aa) —C(S)NH—$C_{1-20}$ alkyl, ab) —C(S)N($C_{1-20}$ alkyl)$_2$, ac) —C(S)NH($C_{1-6}$ alkyl-$C_{6-14}$ aryl), ad) —C(S)N($C_{1-20}$ alkyl)($C_{1-6}$ alkyl-$C_{6-14}$ aryl), ae) —C(S)N($C_{1-6}$ alkyl-$C_{6-14}$ aryl)$_2$, af) —S(O)$_m$NH$_2$, ag) —S(O)$_m$ NH($C_{1-20}$ alkyl), ah) —S(O)$_m$N($C_{1-20}$ alkyl)$_2$, ai) —S(O)$_m$NH($C_{1-6}$ alkyl-$C_{6-14}$ aryl), aj) —S(O)$_m$N($C_{1-20}$ alkyl)($C_{1-6}$ alkyl-$C_{6-14}$ aryl), ak) —S(O)$_m$N($C_{1-6}$ alkyl-$C_{6-14}$ aryl)$_2$, al) —Si($C_{1-20}$ alkyl)$_3$, am) a $C_{1-20}$ alkyl group, an) a $C_{2-20}$ alkenyl group, ao) a $C_{2-10}$ alkynyl group, ap) a $C_{1-20}$ alkoxy group, aq) a $C_{1-20}$ alkylthio group, ar) a $C_{1-20}$ haloalkyl group, as) a $C_{3-10}$ cycloalkyl group, at) a $C_{6-14}$ aryl group, au) a 3-12 membered cycloheteroalkyl group, or av) a 5-14 membered heteroaryl group;

Y, at each occurrence, is a) a divalent $C_{1-20}$ alkyl group, b) a divalent $C_{1-20}$ haloalkyl group, or c) a covalent bond; and m, at each occurrence, is 0, 1 or 2.

6. The compound of claim 5, wherein U', U", V' and V" are C; U'" is O, S, or S(O); U and V independently are CH, C$R^h$, or N; and $R^h$, at each occurrence, is selected from —CN, —CHO, —C(O)—$C_{1-10}$ alkyl, —S(O)$_2$—O$C_{1-10}$ alkyl, a $C_{1-10}$ alkyl group, a $C_{1-10}$ haloalkyl group, and a $C_{6-14}$ aryl group.

7. The compound of claim 5, wherein W and Z independently are selected from H, —CN, —CHO, —C(O)—O$C_{1-10}$ alkyl, —S(O)$_2$—O$C_{1-10}$ alkyl, a $C_{1-10}$ alkyl group, a $C_{1-10}$ haloalkyl group, and a $C_{6-14}$ aryl group, and W' and Z' independently are selected from O, CH$_2$, CHF, CF$_2$, C(CN)$_2$, CH(CN), and C(CF$_3$)$_2$.

8. The compound of claim 5, wherein U and V, together with W and Z, form an optionally substituted $C_{3-10}$ cycloalkyl group or an optionally substituted 3-12 membered cycloheteroalkyl group, wherein the $C_{3-10}$ cycloalkyl group and the 3-12 membered cycloheteroalkyl group are selected from a cyclohexenyl group, a tetrahydrofuranyl group, a 1,3-dioxolanyl group, a pyrrolidinyl group, a pyrazolidinyl group, a triazolidinyl group, and a bicyclo[2.2.1]heptanyl group, and each of these groups optionally is substituted with 1-4 groups independently selected from an oxo group, a methyl group, and a phenyl group.

9. The compound of claim 5 selected from:

N,N'-bis[9',10'-dihydro-9',10'-(1",2"-dicarbomethoxy)-etheno-anthracene-9'-yl]-1,7-dibromoperylene-3,4:9,10-bis(dicarboximide), N,N'-bis[9',10'-dihydro-9',10'-(1",2"-dicarbomethoxy)-etheno-anthracene-9'-yl]-1,6-dibromoperylene-3,4:9,10-bis(dicarboximide), N,N'-bis[9',10'-dihydro-9',10'-(1",2"-dicarbomethoxy)-etheno-anthracene-9'-yl]-1,7-dicyanoperylene-3,4:9,10-bis(dicarboximide), N,N'-bis[9',10'-dihydro-9',10'-(1",2"-dicarbomethoxy)-etheno-anthracene-9'-yl]-1,6-dicyanoperylene-3,4:9,10-bis(dicarboximide), N,N'-bis[9',10'-dihydro-9',10'-(1",2"-dicarbomethoxy)-etheno-anthracene-9'-yl-methyl]-1,7-dibromoperylene-3,4:9,10-bis(dicarboximide), N,N'-bis[9',10'-dihydro-9',10'-(1",2"-dicarbomethoxy)-etheno-anthracene-9'-yl-methyl]-1,6-dibromoperylene-3,4:9,10-bis(dicarboximide), N,N'-bis[9',10'-dihydro-9',10'-(1",2"-dicarbomethoxy)-etheno-anthracene-9'-yl-methyl]-1,7-dicyanoperylene-3,4:9,10-bis(dicarboximide), N,N'-bis[9',10'-dihydro-9',10'-(1",2"-dicarbomethoxy)-etheno-anthracene-9'-yl-methyl]-1,6-dicyanoperylene-3,4:9,10-bis(dicarboximide), N,N'-bis{2-[9',10'-dihydro-9',10'-(1",2"-dicarbomethoxy)-etheno-anthracene-9'-yl]-ethyl}-1,7-dibromoperylene-3,4:9,10-bis(dicarboximide), N,N'-bis{2-[9',10'-dihydro-9',10'-(1",2"-dicarbomethoxy)-etheno-anthracene-9'-yl]-ethyl}-1,6-dibromoperylene-3,4:9,10-bis(dicarboximide), N,N'-bis{2-[9',10'-dihydro-9',10'-(1",2"-dicarbomethoxy)-etheno-anthracene-9'-yl]-ethyl}-1,7-dicyanoperylene-3,4:9,10-bis(dicarboximide), N,N'-bis{2-[9',10'-dihydro-9',10'-(1",2"-dicarbomethoxy)-etheno-anthracene-9'-yl]-ethyl}-1,6-dicyanoperylene-3,4:9,10-bis(dicarboximide), N,N'-bis{3-[9',10'-dihydro-9',10'-(1",2"-dicarbomethoxy)-etheno-anthracene-9'-yl]-propyl}-1,7-dibromoperylene-3,4:9,10-bis(dicarboximide), N,N'-bis{3-[9',10'-dihydro-9',10'-(1",2"-dicarbomethoxy)-etheno-anthracene-9'-yl]-propyl}-1,6-dibromoperylene-3,4:9,10-bis(dicarboximide), N,N'-bis{3-[9',10'-dihydro-9',10'-(1",2"-dicarbomethoxy)-etheno-anthracene-9'-yl]-propyl}-1,7-dicyanoperylene-3,4:9,10-bis(dicarboximide), N,N'-bis{3-[9',10'-dihydro-9',10'-(1",2"-dicarbomethoxy)-etheno-anthracene-9'-yl]-propyl}-1,6-dicyanoperylene-3,4:9,10-bis(dicarboximide), N,N'-bis{3-[9',10'-dihydro-9',10'-(1",2"-dicarbomethoxy)-ethano-anthracene-9'-yl]-propyl}-1,7-dibromoperylene-3,4:9,10-bis(dicarboximide), N,N'-bis{3-[9',10'-dihydro-9',10'-(1",2"-dicarbomethoxy)-ethano-anthracene-9'-yl]-propyl}-1,6-dibromoperylene-3,4:9,10-bis(dicarboximide), N,N'-bis{3-[9',10'-dihydro-9',10'-(1",2"-dicarbomethoxy)-ethano-anthracene-9'-yl]-propyl}-1,7-dicyanoperylene-3,4:9,10-bis(dicarboximide), N,N'-bis{3-[9',10'-dihydro-9',10'-(1",2"-dicarbomethoxy)-ethano-anthracene-9'-yl]-propyl}-1,6-dicyanoperylene-3,4:9,10-bis(dicarboximide), N,N'-bis{3-[9',10'-dihydro-9',10'-(1",2"-ditrifluoromethyl)-etheno-anthracene-9'-yl]-propyl}-1,7-dibromoperylene-3,4:9,10-bis(dicarboximide), N,N'-bis{3-[9',10'-dihydro-9',10'-(1",2"-ditrifluoromethyl)-etheno-anthracene-9'-yl]-propyl}-1,6-dibromoperylene-3,4:9,10-bis(dicarboximide), N,N'-bis{3-[9',10'-dihydro-9',10'-(1",2"-ditrifluoromethyl)-etheno-anthracene-9'-yl]-propyl}-1,7-dicyanoperylene-3,4:9,10-bis(dicarboximide), N,N'-bis{3-[9',10'-dihydro-9',10'-(1",2"-ditrifluoromethyl)-etheno-anthracene-9'-yl]-propyl}-1,6-dicyanoperylene-3,4:9,10-bis(dicarboximide), N,N'-bis{3-[9',10'-dihydro-9',10'-(2",5"-dioxo-tetrahydrofura-3",4"-no)-anthracene-9'-yl]-propyl}-1,7-dibromoperylene-3,4:9,10-bis(dicarboximide), N,N'-bis{3-[9',10'-dihydro-9',10'-(2",5"-dioxo-tetrahydrofura-3",4"-no)-anthracene-9'-yl]-propyl}-1,6-dibromoperylene-3,4:9,10-bis(dicarboximide), N,N'-bis{3-[9',10'-dihydro-9',10'-(2",5"-dioxo-tetrahydrofura-3",4"-no)-anthracene-9'-yl]-propyl}-1,7-dicyanoperylene-3,4:9,10-bis(dicarboximide), N,N'-bis{3-[9',10'-dihydro-9',10'-(2",5"-dioxo-tetrahydrofura-3",4"-no)-anthracene-9'-yl]-propyl}-1,6-dicyanoperylene-3,4:9,10-bis(dicarboximide), N,N'-bis{3-[9',10'-dihydro-9',10'-(1",3"-dioxolan-2"-one-4",5"-no)-anthracene-9'-yl]-propyl}-1,7-dibromoperylene-3,4:9,10-bis(dicarboximide), N,N'-bis{3-[9',10'-dihydro-9',10'-(1",3"-dioxolan-2"-one-4",5"-no)-anthracene-9'-yl]-propyl}-1,6-dibromoperylene-3,4:9,10-bis(dicarboximide), N,N'-bis{3-[9',10'-dihydro-9',10'-(1",3"-dioxolan-2"-one-4",5"-no)-anthracene-9'-yl]-propyl}-1,7-dicyanoperylene-3,4:9,10-bis(dicarboximide), N,N'-bis{3-[9',10'-dihydro-9',10'-(1",3"-dioxolan-2"-one-4",5"-no)-anthracene-9'-yl]-propyl}-1,6-dicyanoperylene-3,4:9,10-bis(dicarboximide), N,N'-bis{3-[9',10'-dihydro-9',10'-(4"-phenyl-1",2",4"-triazolidine-3,5-dione-1",2"-no)-anthracene-9'-yl]-propyl}-1,7-dibromoperylene-3,4:9,10-bis(dicarboximide), N,N'-bis{3-[9',10'-dihydro-9',10'-(4"-phenyl-1",2",4"-triazolidine-3,5-dione-1",2"-no)-anthracene-9'-yl]-propyl}-1,6-dibromoperylene-3,4:9,10-bis(dicarboximide), N,N'-bis({3-[9',10'-dihydro-9',10'-(4"-phenyl-1",2",4"-triazolidine-3,5-dione-1",2"-no)-anthracene-9'-yl]-propyl}-1,7-dicyanoperylene-3,4:9,10-bis(dicarboximide), N,N'-bis{3-[9',10'-dihydro-9',10'-(4"-phenyl-1",2",4"-triazolidine-3,5-dione-1",2"-no)-anthracene-9'-yl]-propyl}-1,6-dicyanoperylene-3,4:9,10-bis(dicarboximide), N,N'-bis[(methylurazolyl)anthracene-9'-yl-propyl]-1,7-dibromoperylene-3,4:9,10-bis(dicarboximide), N,N'-bis[(methylurazolyl)anthracene-9'-yl-propyl]-1,6-dibromoperylene-3,4:9,10-bis(dicarboximide), N,N'-bis[(methylurazolyl)anthracene-9'-yl-propyl]-1,7-dicyanoperylene-3,4:9,10-bis(dicarboximide), and N,N'-bis[(methylurazolyl)anthracene-9'-yl-propyl]-1,6-dicyanoperylene-3,4:9,10-bis(dicarboximide).

10. A composition comprising the compound of claim 5.

11. A method of preparing a thin film semiconductor material comprising the compound of claim 1, the method comprising:

preparing a precursor composition that comprises a compound of formula II':

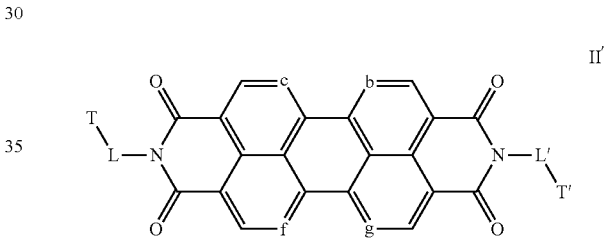

in one or more organic solvents;

wherein:

b, c, f and g independently are CH or $CR^a$, provided that at least one of b, c, f and g is $CR^a$;

L and L' independently are a divalent $C_{1-20}$ alkyl group or a covalent bond; and T and T' independently are selected from:

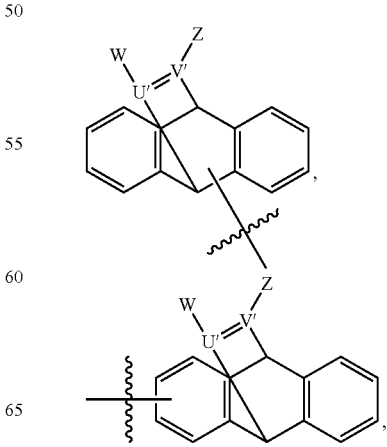

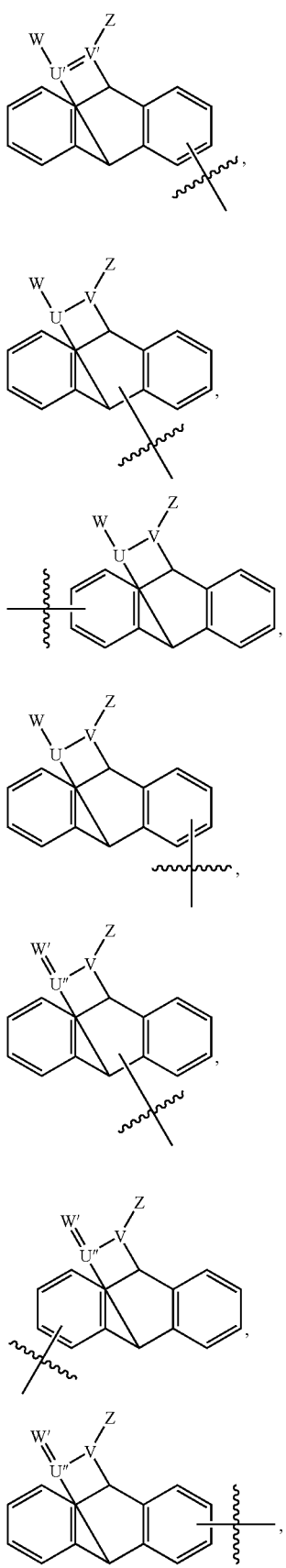

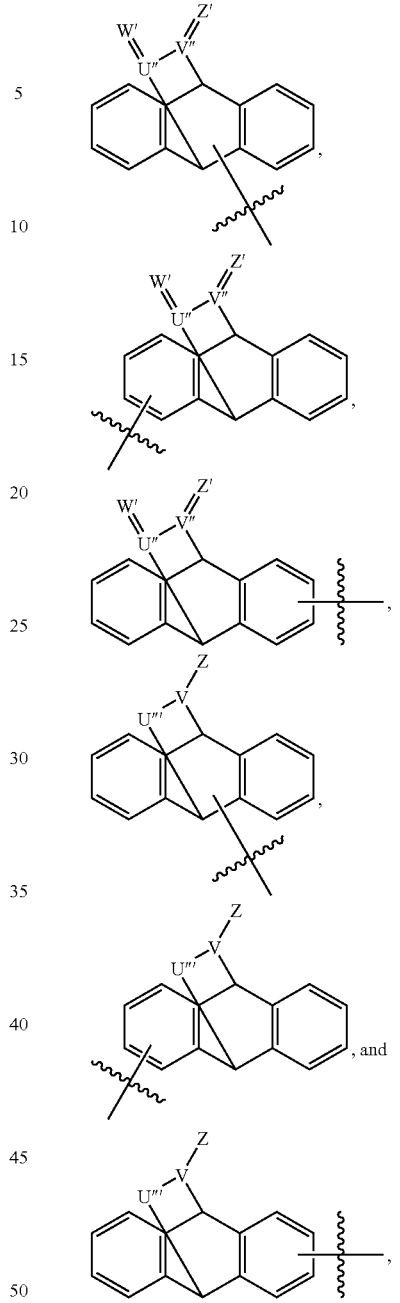

wherein each of these groups can be optionally substituted with 1-10 $R^{a'}$ groups, and U and V, at each occurrence, independently are CH, $CR^h$, $SiR^i$, N or P;

U', U'', V' and V'' independently are C or Si;

U''' is O, $S(O)_m$, or Se;

W and Z, at each occurrence, independently are H or $R^{h'}$, or W and Z, together with U and V, form a $C_{3-10}$ cycloalkyl group or a 3-12 membered cycloheteroalkyl group, wherein the $C_{3-10}$ cycloalkyl group and the 3-12 membered cycloheteroalkyl group optionally is substituted with 1-4 $R^n$ groups;

W' and Z', at each occurrence, independently are O, $CR^jR^{j'}$ or $NR^m$;

$R^a$ and $R^{a'}$, at each occurrence, independently are a) halogen, b) —CN, c) —$NO_2$, d) —O—Y—$R^d$, e) —$NR^e$—

Y—$R^f$, f) —N(O)$R^e$—Y—$R^f$, g) —S(O)$_m R^e$, h) —S(O)$_m$ O—Y—$R^d$, i) —S(O)$_m$N$R^e$—Y—$R^f$, j) —C(O)$R^e$, k) —C(O)O—Y—$R^d$, l) —C(O)N$R^e$—Y—$R^f$, m) —C(S)N$R^e$—Y—$R^f$, n) —Si(C$_{1-20}$ alkyl)$_3$, o) a C$_{1-20}$ alkyl group, p) a C$_{2-20}$ alkenyl group, q) a C$_{2-20}$ alkynyl group, r) a —Y—C$_{3-10}$ cycloalkyl group, s) a —Y—C$_{6-14}$ aryl group, t) a —Y-3-12 membered cycloheteroalkyl group, or u) a —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-4 $R^g$ groups;

$R^d$, at each occurrence, is a) H, b) —C(O)$R^e$, c) —C(O)NR$^e R^f$, d) —C(S)$R^e$, e) —C(S)NR$^e R^f$, f) a C$_{1-20}$ alkyl group, g) a C$_{2-20}$ alkenyl group, h) a C$_{2-20}$ alkynyl group, i) —Y—C$_{3-10}$ cycloalkyl group, j) —Y—C$_{6-14}$ aryl group, k) —Y-3-12 membered cycloheteroalkyl group, or l) —Y-5-14 membered heteroaryl group, wherein each of the C$_{1-20}$ alkyl group, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-4 $R^g$ groups;

$R^e$ and $R^f$, at each occurrence, independently are a) H, b) —OH, c) —SH, d) —S(O)$_2$OH, e) —C(O)OH, f) —C(O)NH$_2$, g) —C(S)NH$_2$, h) —OC$_{1-20}$ alkyl, i) —O—Y—C$_{6-14}$ aryl, j) —C(O)—C$_{1-20}$ alkyl, k) —C(O)—OC$_{1-20}$ alkyl, l) —C(S)N(C$_{1-20}$ alkyl)$_2$, m) —C(S)NH—C$_{1-20}$ alkyl, n) —C(O)NH—C$_{1-20}$ alkyl, o) —C(O)N(C$_{1-20}$ alkyl)$_2$, p) —S(O)$_m$—C$_{1-20}$ alkyl, q) —S(O)$_m$—OC$_{1-20}$ alkyl, r) —C(O)—Y—C$_{6-14}$ aryl, s) —C(O)—O—Y—C$_{6-14}$ aryl, t) —C(S)N(—Y—C$_{6-14}$ aryl)$_2$, u) —C(S)N(C$_{1-20}$ alkyl) —Y—C$_{6-14}$ aryl, v) —C(S)NH—Y—C$_{6-14}$ aryl, w) —C(O)NH—Y—C$_{6-14}$ aryl, x) —C(O)N(C$_{1-20}$ alkyl) —Y—C$_{6-14}$ aryl, y) —C(O)N(Y—C$_{6-14}$ aryl)$_2$, z) —S(O)$_m$—Y—C$_{6-14}$ aryl, aa) —S(O)$_m$—O—Y—C$_{6-14}$ aryl, ab) a C$_{1-20}$ alkyl group, ac) a C$_{2-20}$ alkenyl group, ad) a C$_{2-20}$ alkynyl group, ae) —Y—C$_{3-10}$ cycloalkyl group, af) —Y—C$_{6-14}$ aryl group, ag) —Y-3-12 membered cycloheteroalkyl group, or ah) —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl groups, the 3-12 membered cycloheteroalkyl group, and the 5-14 membered heteroaryl group optionally is substituted with 1-4 $R^g$ groups;

$R^g$, at each occurrence, is a) halogen, b) —CN, c) —NO$_2$, d) oxo, e) —OH, f) —NH$_2$, g) —NH(C$_{1-20}$ alkyl), h) —N(C$_{1-20}$ alkyl)$_2$, i) —NH(C$_{1-6}$ alkyl-C$_{6-14}$ aryl), j) —N(C$_{1-20}$ alkyl)(C$_{1-6}$ alkyl-C$_{6-14}$ aryl), k) —N(C$_{1-6}$ alkyl-C$_{6-14}$ aryl)$_2$, l) —S(O)$_m$H, m) —S(O)$_m$—C$_{1-20}$ alkyl, n) —S(O)$_2$OH, o) —S(O)$_m$—OC$_{1-20}$ alkyl, p) —CHO, q) —C(O)—C$_{1-20}$ alkyl, r) —C(O)OH, s) —C(O)—OC$_{1-20}$ alkyl, t) —C(O)NH$_2$, u) —C(O)NH—C$_{1-20}$ alkyl, v) —C(O)N(C$_{1-20}$ alkyl)$_2$, w) —C(O)NH(C$_{1-6}$ alkyl-C$_{6-14}$ aryl), x) —C(O)N(C$_{1-20}$ alkyl)(C$_{1-6}$ alkyl-C$_{6-14}$ aryl), y) —C(O)N(C$_{1-6}$ alkyl-C$_{6-14}$ aryl)$_2$, z) —C(S)NH$_2$, aa) —C(S)NH—C$_{1-20}$ alkyl, ab) —C(S)N(C$_{1-20}$ alkyl)$_2$, ac) —C(S)NH(C$_{1-6}$ alkyl-C$_{6-14}$ aryl), ad) —C(S)N(C$_{1-20}$ alkyl)(C$_{1-6}$ alkyl-C$_{6-14}$ aryl), ae) —C(S)N(C$_{1-6}$ alkyl-C$_{6-14}$ aryl)$_2$, af) —S(O)$_m$NH$_2$, ag) —S(O)$_m$NH(C$_{1-20}$ alkyl), ah) —S(O)$_m$N(C$_{1-20}$ alkyl)$_2$, ai) —S(O)$_m$NH(C$_{1-6}$ alkyl-C$_{6-14}$ aryl), aj) —S(O)$_m$N(C$_{1-20}$ alkyl)(C$_{1-6}$ alkyl-C$_{6-14}$ aryl), ak) —S(O)$_m$N(C$_{1-6}$ alkyl-C$_{6-14}$ aryl)$_2$, al) —Si(C$_{1-20}$ alkyl)$_3$, am) a C$_{1-20}$ alkyl group, an) a C$_{2-20}$ alkenyl group, ao) a C$_{2-10}$ alkynyl group, ap) a C$_{1-20}$ alkoxy group, aq) a C$_{1-20}$ alkylthio group, ar) a C$_{1-20}$ haloalkyl group, as) a C$_{3-10}$ cycloalkyl group, at) a C$_{6-14}$ aryl group, au) a 3-12 membered cycloheteroalkyl group, or av) a 5-14 membered heteroaryl group;

$R^h$ and $R^{h'}$, at each occurrence, independently are a) halogen, b) —CN, c) —NO$_2$, d) —O—Y—$R^k$, e) —NR—Y—$R^m$, f) —N(O)R—Y—$R^m$, g) —S(O)$_m R^l$, h) —S(O)$_m$ O—Y—$R^k$, i) —S(O)$_m$N$R^l$—Y—$R^m$, j) —C(O)$R^l$, k) —C(O)O—Y—$R^k$, l) —C(O)N$R^l$—Y—$R^m$, m) —C(S)N$R^l$—Y—$R^m$, n) —Si(C$_{1-20}$ alkyl)$_3$, o) a C$_{1-20}$ alkyl group, p) a C$_{2-20}$ alkenyl group, q) a C$_{2-20}$ alkynyl group, r) a —Y—C$_{3-10}$ cycloalkyl group, s) a —Y—C$_{6-14}$ aryl group, t) a —Y-3-12 membered cycloheteroalkyl group, or u) a —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-4 $R^n$ groups;

$R^i$, at each occurrence, is a) H, b) a C$_{1-20}$ alkyl group, c) a —Y—C$_{6-14}$ aryl group, d) an —O—C$_{1-20}$ alkyl group, or e) an —O—Y—C$_{6-14}$ aryl group, wherein each of the C$_{1-20}$ alkyl groups and the C$_{6-14}$ aryl groups optionally is substituted with 1-4 $R^n$ groups;

$R^j$ and $R^{j'}$, at each occurrence, independently are a) H, b) halogen, c) —CN, d) CHO, e) —C(O)—OC$_{1-20}$ alkyl, f) a C$_{1-20}$ alkyl group, or g) a —Y—C$_{6-14}$ aryl group, wherein each of the C$_{1-20}$ alkyl groups and the C$_{6-14}$ aryl group optionally is substituted with 1-4 $R^n$ groups;

$R^k$, at each occurrence, is a) H, b) —C(O)$R^e$, c) —C(O)NR$^e R^f$, d) —C(S)$R^e$, e) —C(S)NR$^e R^f$, f) a C$_{1-20}$ alkyl group, g) a C$_{2-20}$ alkenyl group, h) a C$_{2-20}$ alkynyl group, i) —Y—C$_{3-10}$ cycloalkyl group, j) —Y—C$_{6-14}$ aryl group, k) —Y-3-12 membered cycloheteroalkyl group, or l) —Y-5-14 membered heteroaryl group, wherein each of the C$_{1-20}$ alkyl group, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-4 $R^n$ groups;

$R^l$ and $R^m$, at each occurrence, independently are a) H, b) —OH, c) —SH, d) —S(O)$_2$ OH, e) —C(O)OH, f) —C(O)NH$_2$, g) —C(S)NH$_2$, h) —OC$_{1-20}$ alkyl, i) —O—Y—C$_{6-14}$ aryl, j) —C(O)—C$_{1-20}$ alkyl, k) —C(O)—OC$_{1-20}$ alkyl, l) —C(S)N(C$_{1-20}$ alkyl)$_2$, m) —C(S)NH—C$_{1-20}$ alkyl, n) —C(O)NH—C$_{1-20}$ alkyl, o) —C(O)N(C$_{1-20}$ alkyl)$_2$, p) —S(O)$_m$—C$_{1-20}$ alkyl, q) —S(O)$_m$—OC$_{1-20}$ alkyl, r) —C(O)—Y—C$_{6-14}$ aryl, s) —C(O)—O—Y—C$_{6-14}$ aryl, t) —C(S)N(—Y—C$_{6-14}$ aryl)$_2$, u) —C(S)N(C$_{1-20}$ alkyl) —Y—C$_{6-14}$ aryl, v) —C(S)NH—Y—C$_{6-14}$ aryl, w) —C(O)NH—Y—C$_{6-14}$ aryl, x) —C(O)N(C$_{1-20}$ alkyl) —Y—C$_{6-14}$ aryl, y) —C(O)N(Y—C$_{6-14}$ aryl)$_2$, z) —S(O)$_m$—Y—C$_{6-14}$ aryl, aa) —S(O)$_m$—O—Y—C$_{6-14}$ aryl, ab) a C$_{1-20}$ alkyl group, ac) a C$_{2-20}$ alkenyl group, ad) a C$_{2-20}$ alkynyl group, ae) —Y—C$_{3-10}$ cycloalkyl group, af) —Y—C$_{6-14}$ aryl group, ag) —Y-3-12 membered cycloheteroalkyl group, or ah) —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl groups, the 3-12 membered cycloheteroalkyl group, and the 5-14 membered heteroaryl group optionally is substituted with 1-4 R″ groups;

R″, at each occurrence, is a) halogen, b) —CN, c) —NO$_2$, d) oxo, e) —OH, f) —NH$_2$, g) —NH(C$_{1-20}$ alkyl), h) —N(C$_{1-20}$ alkyl)$_2$, i) —NH(C$_{1-6}$ alkyl-C$_{6-14}$ aryl), j) —N(C$_{1-20}$ alkyl)(C$_{1-6}$ alkyl-C$_{6-14}$ aryl), k) —N(C$_{1-6}$ alkyl-C$_{6-14}$ aryl)$_2$, l) —S(O)$_m$H, m) —S(O)$_m$—C$_{1-20}$ alkyl, n) —S(O)$_2$OH, o) —S(O)$_m$—OC$_{1-20}$ alkyl, p) —CHO, q) —C(O)—C$_{1-20}$ alkyl, r) —C(O)OH, s) —C(O)—OC$_{1-20}$ alkyl, t) —C(O)NH$_2$, u) —C(O)NH—C$_{1-20}$ alkyl, v) —C(O)N(C$_{1-20}$ alkyl)$_2$, w) —C(O)NH(C$_{1-6}$ alkyl-C$_{6-14}$ aryl), x) —C(O)N(C$_{1-20}$ alkyl)(C$_{1-6}$ alkyl-C$_{6-14}$ aryl), y) —C(O)N(C$_{1-6}$ alkyl-C$_{6-14}$ aryl)$_2$, z) —C(S)NH$_2$, aa) —C(S)NH—C$_{1-20}$ alkyl, ab) —C(S)N(C$_{1-20}$ alkyl)$_2$, ac) —C(S)NH(C$_{1-6}$ alkyl-C$_{6-14}$ aryl), ad) —C(S)N(C$_{1-20}$ alkyl)(C$_{1-6}$ alkyl-C$_{6-14}$ aryl), ae) —C(S)N(C$_{1-6}$ alkyl-C$_{6-14}$ aryl)$_2$, af) —S(O)$_m$NH$_2$, ag) —S(O)$_m$NH(C$_{1-20}$ alkyl), ah) —S(O)$_m$N(C$_{1-20}$ alkyl)$_2$, ai) —S(O)$_m$NH(C$_{1-6}$ alkyl-C$_{6-14}$ aryl), aj) —S(O)$_m$N(C$_{1-20}$ alkyl)(C$_{1-6}$ alkyl-C$_{6-14}$ aryl), ak) —S(O)$_m$N(C$_{1-6}$ alkyl-C$_{6-14}$ aryl)$_2$, al) —Si(C$_{1-20}$ alkyl)$_3$, am) a C$_{1-20}$ alkyl group, an) a C$_{2-20}$ alkenyl group, ao) a C$_{2-10}$ alkynyl group, ap) a C$_{1-20}$ alkoxy group, aq) a C$_{1-20}$ alkylthio group, ar) a C$_{1-20}$ haloalkyl group, as) a C$_{3-10}$ cycloalkyl group, at) a C$_{6-14}$ aryl group, au) a 3-12 membered cycloheteroalkyl group, or av) a 5-14 membered heteroaryl group;

Y, at each occurrence, is a) a divalent C$_{1-20}$ alkyl group, b) a divalent C$_{1-20}$ haloalkyl group, or c) a covalent bond; and m, at each occurrence, is 0, 1 or 2;

depositing the precursor composition on a substrate to provide a thin film semiconductor precursor; and treating the thin film semiconductor precursor to provide a thin film semiconductor material that comprises the compound of claim 1.

12. The compound of claim 1, wherein c and g are CH, and b and f independently are C(Br) or C(CN); or wherein b and g are CH, and c and f independently are C(Br) or C(CN).

13. A composite comprising a substrate and the thin film semiconductor material of claim 4 deposited on the substrate.

14. An organic field effect transistor (OFET) device comprising the composite of claim 13.

15. An organic photovoltaic device comprising the composite of claim 13.

16. An organic photodetector an organic light-emitting device comprising the composite of claim 13.

17. The method of claim 11, wherein depositing comprises inkjet printing, screen-printing, gravure printing, pad printing, offset printing, microcontact printing, spin coating, drop-casting, dip coating, or blade coating.

18. The method of claim 11, wherein the thin film semiconductor precursor is converted to the thin film semiconductor material by heating only.

19. The method of claim 11, wherein the thin film semiconductor precursor is converted to the thin film semiconductor material by exposure to one or more of infrared light, ultraviolet light, ionizing radiation, and chemical reagents.

20. The method of claim 11, wherein the thin film semiconductor precursor is converted to the thin film semiconductor material by heating and exposure to one or more of infrared light, ultraviolet light, ionizing radiation, and chemical reagents.

* * * * *